United States Patent
Blanchard et al.

(10) Patent No.: US 8,415,338 B2
(45) Date of Patent: Apr. 9, 2013

(54) OXYGEN LINKED PYRIMIDINE DERIVATIVES

(75) Inventors: Stephanie Blanchard, Singapore (SG); Cheng Hsia Angeline Lee, Singapore (SG); Harish Kumar Mysore Nagaraj, Singapore (SG); Anders Poulsen, Singapore (SG); Eric T. Sun, Singapore (SG); Yee Ling Evelyn Tan, Singapore (SG); Anthony Deodaunia William, Singapore (SG)

(73) Assignee: Cell Therapeutics, Inc., Seattle, WA (US)

( * ) Notice: Subject to any disclaimer, the term of this patent is extended or adjusted under 35 U.S.C. 154(b) by 0 days.

(21) Appl. No.: 13/438,989

(22) Filed: Apr. 4, 2012

(65) Prior Publication Data

US 2012/0196855 A1    Aug. 2, 2012

Related U.S. Application Data

(62) Division of application No. 12/093,867, filed as application No. PCT/SG2006/000352 on Nov. 15, 2006, now Pat. No. 8,153,632.

(60) Provisional application No. 60/736,838, filed on Nov. 16, 2005, provisional application No. 60/817,339, filed on Jun. 30, 2006, provisional application No. 60/851,283, filed on Oct. 13, 2006.

(51) Int. Cl.
*A61K 31/33* (2006.01)
*C07D 273/00* (2006.01)

(52) U.S. Cl.
USPC .......................................... 514/183; 540/469

(58) Field of Classification Search ........................ None
See application file for complete search history.

(56) References Cited

U.S. PATENT DOCUMENTS

2004/0209895 A1    10/2004  Luecking et al.
2005/0215556 A1     9/2005  Lin et al.

FOREIGN PATENT DOCUMENTS

| WO | WO-2004/026881 A1 | 4/2004 |
| WO | WO-2004/039809 A1 | 5/2004 |
| WO | WO-2004/078682 A2 | 9/2004 |
| WO | WO-2004078682     | 9/2004 |
| WO | WO-2005/047294 A1 | 5/2005 |
| WO | WO-2005/058318 A1 | 6/2005 |

OTHER PUBLICATIONS

Japanese Office Action, Japanese Application No. 2008-541128, dated Jun. 19, 2012.
International Search Report for PCT/SG2006/00352.
Jantzen and Robinson. Modern Pharmaceutics, 1996, p. 596.
Pearson. Expert Reviews on Anticancer Therapy, 2004, 4(6), 1113-1124.
Dancey. Nature Reviews: Drug Discovery, 2003, 2, 296-313.
"Prostate Cancer Prevention", https://www.cancer.gov/cancertopics/pdg/prevention/prostate/patient, accessed Apr. 9, 2010.

*Primary Examiner* — Noble Jarrell
(74) *Attorney, Agent, or Firm* — Novak Druce Connolly Bove + Quigg LLP

(57) ABSTRACT

The present invention relates to pyrimidine compounds that are useful as anti-proliferative agents. More particularly, the present invention relates to oxygen linked and substituted pyrimidine compounds, methods for their preparation, pharmaceutical compositions containing these compounds and uses of these compounds in the treatment of proliferative disorders. These compounds may be useful as medicaments for the treatment of a number of proliferative disorders including tumors and cancers as well as other disorders or conditions related to or associated with kinases.

28 Claims, No Drawings

OXYGEN LINKED PYRIMIDINE DERIVATIVES

CROSS REFERENCE TO RELATED APPLICATIONS

This application is a Divisional of application Ser. No. 12/093,867 filed on Oct. 21, 2008, which is a National Phase filing under 35 U.S.C. §371 of PCT/SG2006/000352 filed Nov. 15, 2006, and claims priority to Provisional Patent Application No. 60/736,838, filed in the United States on Nov. 16, 2005, Provisional Patent Application No. 60/817,339, filed in the United States on Jun. 30, 2006, and Provisional Patent Application No. 60/851,283, filed in the United States on Oct. 13, 2006. The entire contents of each of the above-applications are incorporated herein by reference.

FIELD OF THE INVENTION

The present invention relates to pyrimidine compounds that may be useful as anti-proliferative agents. More particularly, the present invention relates to oxygen linked and substituted pyrimidine compounds, methods for their preparation, pharmaceutical compositions containing these compounds and uses of these compounds in the treatment of proliferative disorders. These compounds may be useful as medicaments for the treatment of a number of proliferative disorders including tumours and cancers as well as other conditions or disorders associated with kinases.

BACKGROUND OF THE INVENTION

Proliferative disorders such as cancer are characterised by the uncontrolled growth of cells within the body. As such proliferative disorders generally involve an abnormality in the control of cell growth and/or division leading to the formation of tumour and ultimately death. Without wishing to be bound by theory it is thought that this is caused by the pathways that regulate cell growth and division being altered in cancer cells. The alteration is such that the effects of these normal regulatory mechanisms in controlling cell growth and division either fails or is bypassed.

The uncontrolled cell growth and/or division ultimately proves fatal for the patient as successive rounds of mutations on the part of the cell then typically lead to the cancer cells having a selective advantage over normal healthy cells in the body of the patient leading to the cancer cells predominating in the cell mass of the patient. The cancer cells then typically metastasize to colonize other tissues or parts of the body other than the part of origin of the cancer cell leading to secondary tumours which eventually lead to organ failure and the death of the patient. It is the difficulty in controlling the rapid cell growth and division that is characteristic of cancer cells that make it hard to come up with effective chemotherapeutic strategies.

A number of traditional treatments for proliferative disorders such as cancer seek to take advantage of their higher proliferative capacity and thus their higher sensitivity to DNA damage. Treatments that have been utilised include ionizing radiation (γ-rays, X-rays and the like) as well as cytotoxic agents such as bleomycin, cis-platin, vinblastine, cyclophosphamide, 5'-fluorouracil and methotrexate. These treatments all rely on causing damage to DNA and destabilisation of the chromosomal structure eventually leading to death of the cancer cells.

The problem with many of these approaches is that they are non-selective for cancer cells and healthy cells can and often will be adversely affected by the treatment. This is hardly surprising given that the cellular mechanisms targeted by these strategies occur in healthy cells as well as in cancer cells (although typically at slower rates) and merely serves to highlight the difficulty in achieving successful treatment of the cancer in the patient without causing irreparable harm to the healthy cells. As such with many of these treatments there can be devastating side effects which can not only significantly reduce the short term quality of life of the patient but may also have long term detriments on the health of the patient should they survive the cancer attack.

Whilst some of the above problems have substantially been overcome by the development of selective anti-cancer agents (such as tamoxifen) the effectiveness of all chemotherapeutic agents is subject to the development of drug resistance by the cancer cells in the patient. The development of drug resistance in the cancer cells of a patient tends to be class specific and therefore if the cancer cells of a patient develop drug resistance to a class of anti-cancer drugs then all compounds within that class are typically rendered ineffective in the further treatment of that patient. As such in improving clinical outcomes for patients the identification of alternative chemotherapeutic agents is essential in providing the oncologist with an arsenal of drugs that may be used in any given situation.

The development of different classes of therapeutic agents is therefore important as it can help avoid the development of drug resistance and can also be used in combination therapies. Such combination therapies typically involve the use of anti-cancer drugs with different properties and cellular targets which in turn tends to increase the overall effectiveness of any chosen chemotherapy regime and limits the possibility of drug resistance developing in the patient.

One of the major advances in cancer research has been the clinical validation of molecularly targeted drugs that inhibit the activity of protein kinases. Small-molecule kinase inhibitors that are now approved for oncology indications include imatinib, gefitinib, erlotinib, sorafenib, sunitinib and dasatinib [Baselga J., *Science*, 2006, 312, 1175-1178]. A number of kinases such as JAK2, FLT3 and CDK2 are promising kinase targets for pharmacological intervention in solid tumours, hematological malignancies, myeloproliferative disorders and non-malignant proliferative disorders like keloids.

The Janus kinases (JAK) are a family of cytoplasmic tyrosine kinases consisting of JAK1, JAK2, JAK3 and Tyk2. They play a pivotal role in the signaling pathways of numerous cytokines, hormones and growth factors [Rawlings J S et al, *J. Cell Sci.*, 2004, 117, 1281-1283]. Their intracellular substrates include the family of proteins called Signal Transducer and Activator of Transcription (STAT). The JAK-STAT pathways, through the proper actions of the ligands, regulate important physiological processes such as immune response to viruses, erythropoiesis, lactation, lipid homeostasis, etc. However, dysfunctional signaling caused by a myriad of factors result in pathophysiological conditions such as allergies, asthma, rheumatoid arthritis, severe combined immune deficiency, hematological malignancies, etc. In particular, mutations in JAK2 have been associated with myeloproliferative disorders (including polycythemia vera, essential thrombocythemia and idiopathic myelofibrosis) and a wide range of leukemias and lymphomas [Percy M J et al, *Hematol. Oncol.*, 2005, 23, 91-93]. Importantly, the myeloproliferative disorders belong to an area of unmet medical need where some treatment modalities have not been updated over the past few decades [Schafer A I, *Blood*, 2006, 107, 4214-4222].

The myeloproliferative disorders (MPDs) belong to a group of hematological malignancies arising from clonal expansion of mutated progenitor stem cells in the bone marrow. The association of one MPD, chronic myeloid leukemia, with the Philadelphia chromosome has been well documented. The Philadelphia negative MPDs include Essential Thrombocythemia (ET), Polycythemia Vera (PV) and Chronic Idiopathic Myelofibrosis (MF). No effective treatment is currently available. The recent discovery that a single acquired somatic mutation in JAK2 appears responsible for many of the features of these MPDs promises to impact the diagnosis and treatment of patients with these disorders and to spur additional research into the origins of dysregulated cell growth and function. Until recently, most MPDs have been considered to be rare or orphan diseases but studies underway suggest a much higher prevalence.

Essential Thrombocythemia is a chronic MPD characterized by an increased number of circulating platelets, profound marrow megakaryocyte hyperplasia, splenomegaly and a clinical course punctuated by hemorrhagic or thrombotic episodes or both. Current treatment options include low dose aspirin, or platelet lowering agents such as anagrelide, interferon or hydroxyurea. These treatments have severe side effects that compromise the quality of life of patients.

Polycythemia Vera is a chronic progressive MPD characterized by an elevated hematocrit, an increase in the red cell mass, and usually by an elevated leukocyte count, an elevated platelet count and an enlarged spleen. The most common cause of morbidity and mortality is the predisposition of PV patients to develop life threatening arterial and venous thromboses. Treatment options include: phlebotomy with low dose aspirin or myelosuppressive therapy options such as hydroxyurea, interferon or anagrelide. Again, these treatments are not ideal due to severe side effects.

Chronic Idiopathic Myelofibrosis (MF) is a chronic malignant hematological disorder characterized by an enlarged spleen, varying degrees of anemia and low platelet counts, red cells in the peripheral blood that resemble tear drops, the appearance of small numbers of immature nucleated red cells and white cells in the blood, varying degrees of fibrosis of the marrow cavity (myelofibrosis) and the presence of marrow cells outside the marrow cavity (extramedullary hematopoiesis or myeloid metaplasia). Current treatment is directed at alleviation of constitutional symptoms, anemia and symptomatic splenomegaly. Treatment options include hydroxyurea, interferon, thalidomide with prednisone, and allogeneic stem cell transplant. MF has the worst prognosis among the Philadelphia negative MPD and represents an area of greatest unmet medical need.

In addition, due to its role in the angiotensin II signaling pathway, JAK2 is also implicated in the etiology of cardiovascular diseases like congestive heart failure and pulmonary hypertension [Berk B C et al, *Circ. Res*, 1997, 80, 607-616]. Furthermore, a putative role for JAK2 has been demonstrated in keloid pathogenesis and may constitute a new approach for keloid management [Lim C P et al, *Oncogene*, 2006, 25, 5416-5425]. Yet another potential application for JAK2 inhibitors lies in the treatment of retinal diseases as JAK2 inhibition was found to offer protective effects on photoreceptors in a mouse model of retinal degeneration [Samardzija M et al, *FASEB J.*, 2006, 10, 1096].

A family of Class III receptor tyrosine kinases (RTK), including c-Fms, c-Kit, fms-like receptor tyrosine kinase 3 (FLT3), and platelet-derived growth factor receptors (PDGFRα and β), play an important role in the maintenance, growth and development of hematopoietic and non-hematopoietic cells. Overexpression and activating mutations of these RTKs are known to be involved in the pathophysiology of diverse human cancers from both solid and hematological origins [Hannah A L, *Curr. Mol. Med.*, 2005, 5, 625-642]. FLT3 mutations were first reported as internal tandem duplication (FLT3/ITD) of the juxtamembrane domain-coding sequence; subsequently, point mutations, deletions, and insertions surrounding the D835 coding sequence have been found [Parcells B W et al, *Stem Cells*, 2006, 24, 1174-1184]. FLT3 mutations are the most frequent genetic alterations reported in acute myeloid leukemia (AML) and are involved in the signaling pathway of autonomous proliferation and differentiation block in leukemia cells [Tickenbrock L et al, *Expert Opin. Emerging Drugs*, 2006, 11, 1-13]. Several clinical studies have confirmed that FLT3/ITD is strongly associated with a poor prognosis. Because high-dose chemotherapy and stem cell transplantation cannot overcome the adverse effects of FLT3 mutations, the development of FLT3 kinase inhibitors could produce a more efficacious therapeutic strategy for leukemia therapy.

Cyclin-dependent kinases (CDKs) are serine-threonine kinases that play important roles in cell cycle control (CDK1, 2, 4 and 6), transcription initiation (CDK7 and 9), and neuronal function (CDK5) [Knockaert M et al, *Trends Pharmacol. Sci.*, 2002, 23, 417-425]. Aberrations in the cell cycle CDKs and their cyclin partners have been observed in various tumour types, including those of the breast, colon, liver and brain [Shapiro G I, *J. Clin. Oncol.*, 2006, 24, 1770-1783]. It is believed that the pharmacological inhibition of CDK1, 2, 4, 6 and/or 9 may provide a new therapeutic option for diverse cancer patients. In particular, the simultaneous inhibition of CDK1, 2 and 9 has recently been shown to result in enhanced apoptotic killing of lung cancer (H1299) and osteosarcoma cells (U205), compared with inhibition of single CDK alone [Cai D et al, *Cancer Res*, 2006, 66, 9270-9280].

Accordingly, compounds that are kinase inhibitors have the potential to meet the need to provide further biologically active compounds that would be expected to have useful, improved pharmaceutical properties in the treatment of kinase related conditions or disorders such as cancer and other proliferative disorders.

SUMMARY OF THE INVENTION

In one aspect the present invention provides a compound of formula (I):

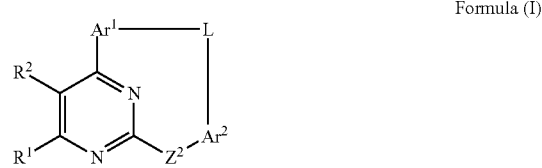

Formula (I)

wherein:
$R^1$ and $R^2$ are each independently selected from the group consisting of: H, halogen, alkyl, alkenyl, alkynyl, haloalkyl, haloalkenyl, heteroalkyl, cycloalkyl, cycloalkenyl, heterocycloalkyl, heterocycloalkenyl, aryl, heteroaryl, cycloalkylalkyl, heterocycloalkylalkyl, arylalkyl, heteroarylalkyl, arylalkenyl, cycloalkylheteroalkyl, heterocycloalkylheteroalkyl, heteroarylheteroalkyl, arylheteroalkyl, hydroxy, hydroxyalkyl, alkoxy, alkoxyalkyl, alkoxyaryl, alkenyloxy, alkynyloxy, cycloalkyloxy, heterocycloalkyloxy, aryloxy, arylalkyloxy, phenoxy, benzyloxy, heteroaryloxy, amino, alkylamino, aminoalkyl, acylamino, arylamino, sulfonylamino, sulfinylamino, —COOH, —COR³, —COOR³, —CONHR³, —NHCOR³, —NHCOOR³, —NHCONHR³, alkoxycarbonyl, alkylaminocarbonyl, sulfonyl, alkylsulfonyl, alkylsulfonyl, arylsulfonyl, arylsulfinyl, aminosulfonyl, —SR³, R⁴S(O)R⁶—, R⁴S(O)₂R⁶—, R⁴C(O)N(R⁵)R⁶—, R⁴SO₂N(R⁵)R⁶—, R⁴N(R⁵)C(O)R⁶—, R⁴N(R⁵)SO₂R⁶—, R⁴N(R⁵)C(O)N(R⁵)R⁶— and acyl, each of which may be optionally substituted;

each R³, R⁴, and R⁵ is independently selected from the group consisting of H, alkyl, alkenyl, alkynyl, haloalkyl, heteroalkyl, cycloalkyl, heterocycloalkyl, aryl, heteroaryl, cycloalkylalkyl, heterocycloalkylalkyl, arylalkyl, heteroarylalkyl and acyl, each of which may be optionally substituted;

each R⁶ is independently selected from the group consisting of a bond, alkyl, alkenyl, alkynyl, haloalkyl, heteroalkyl, cycloalkyl, heterocycloalkyl, aryl, heteroaryl, cycloalkylalkyl, heterocycloalkylalkyl, arylalkyl, heteroarylalkyl and acyl, each of which may be optionally substituted;

Z² is independently selected from the group consisting of a bond, O, S, —N(R⁷)—, —N(R⁷)C₁₋₂alkyl-, and —C₁₋₂alkylN(R⁷)—;

each R⁷ is independently selected from the group consisting of H, alkyl, alkenyl, alkynyl, haloalkyl, heteroalkyl, cycloalkyl, heterocycloalkyl, aryl, heteroaryl, cycloalkylalkyl, heterocycloalkylalkyl, arylalkyl, heteroarylalkyl and acyl, each of which may be optionally substituted;

Ar¹ and Ar² are each independently selected from the group consisting of aryl and heteroaryl, each of which may be optionally substituted;

L is a group of formula:

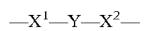

wherein X¹ is attached to Ar¹ and X² is attached to Ar², and wherein X¹, X² and Y are selected such that the group L has between 5 and 15 atoms in the normal chain, X¹ and X² are each independently a heteroalkyl group containing at least one oxygen atom in the normal chain, Y is a group of formula —CR$^a$=CR$^b$— or an optionally substituted cycloalkyl group, wherein R$^a$ and R$^b$ are each independently selected from the group consisting of H, alkyl, alkenyl, alkynyl, haloalkyl, heteroalkyl, cycloalkyl, heterocycloalkyl, aryl, heteroaryl, cycloalkylalkyl, heterocycloalkylalkyl, arylalkyl, heteroarylalkyl and acyl, each of which may be optionally substituted, or R$^a$ and R$^b$ may be joined such that when taken together with the carbon atoms to which they are attached they form a cycloalkenyl or cycloheteroalkenyl group;

or a pharmaceutically acceptable, salt, N-oxide, or prodrug thereof.

As with any group of structurally related compounds which possess a particular utility, certain embodiments of variables of the compounds of the Formula (I), are particularly useful in their end use application.

In certain embodiments Z² is selected from the group consisting of a bond, —N(R⁷)— and —S—. In one specific embodiment Z² is —N(R⁷)—. In an even more specific embodiment Z² is —N(H)—.

Ar¹ and Ar² are each independently selected from the group consisting of aryl and heteroaryl and may be monocyclic, bicyclic or polycyclic moieties. In certain embodiments each of Ar¹ and Ar² is a monocyclic or bicyclic moiety. In certain embodiments each of Ar¹ and Ar² are a monocyclic moiety.

In certain embodiments Ar¹ is selected from the group consisting of:

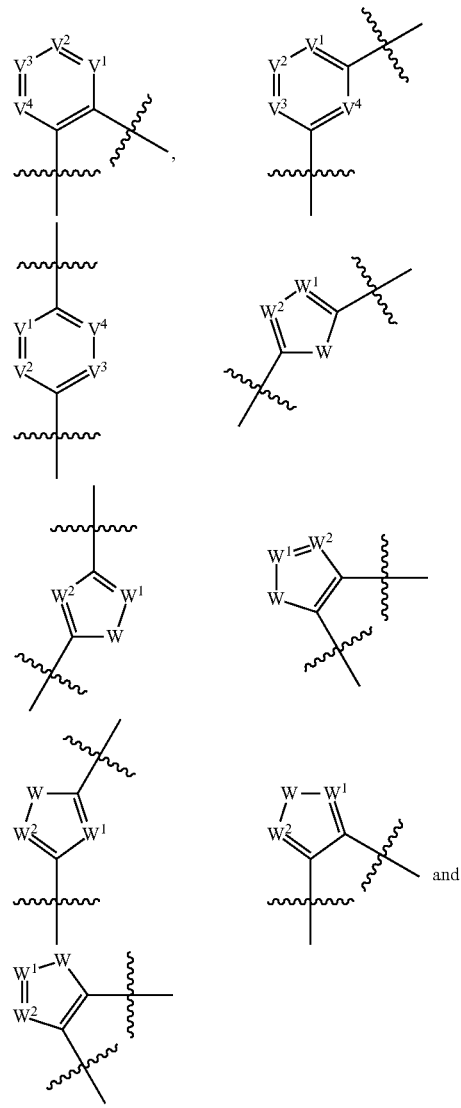

wherein V¹, V², V³ and V⁴ are each independently selected from the group consisting of N, and C(R¹⁰);

W is selected from the group consisting of O, S and NR¹⁰;

W¹ and W² are each independently selected from the group consisting of N and CR¹⁰;

wherein each R¹⁰ is independently selected from the group consisting of: H, halogen, alkyl, alkenyl, alkynyl, haloalkyl, haloalkenyl, heteroalkyl, cycloalkyl, cycloalkenyl, heterocycloalkyl, heterocycloalkenyl, aryl, heteroaryl, cycloalkylalkyl, heterocycloalkylalkyl, arylalkyl, heteroarylalkyl, arylalkenyl, cycloalkylheteroalkyl, heterocycloalkylheteroalkyl, heteroarylheteroalkyl, arylheteroalkyl, hydroxy, hydroxyalkyl, alkoxy, alkoxyalkyl, alkoxyaryl, alkenyloxy, alkynyloxy, cycloalkyloxy, heterocycloalkyloxy, aryloxy, arylalkyloxy, phenoxy, benzyloxy, heteroaryloxy, amino, alkylamino, aminoalkyl, acylamino, arylamino, sulfonylamino, sulfinylamino, —COOH, —COR³, —COOR³, —CONHR³, —NHCOR³, —NHCOOR³, —NHCONHR³, alkoxycarbonyl, alkylaminocarbonyl, sulfonyl, alkylsulfonyl, alkylsulfinyl, arylsulfonyl, arylsulfinyl, aminosulfonyl, —SR$^3$, R$^4$S(O)R$^6$—, R$^4$S(O)$_2$R$^6$—, R$^4$C(O)N(R$^5$)R$^6$—, R$^4$SO$_2$N(R$^5$)R$^6$—, R$^4$N(R$^5$)C(O)R$^6$—, R$^4$N(R$^5$)SO$_2$R$^6$—, R$^4$N(R$^5$)C(O)N(R$^5$)R$^6$— and acyl, each of which may be optionally substituted, wherein R$^3$, R$^4$, R$^5$ and R$^6$ are as defined above.

In certain embodiments Ar$^1$ is selected from the group consisting of:

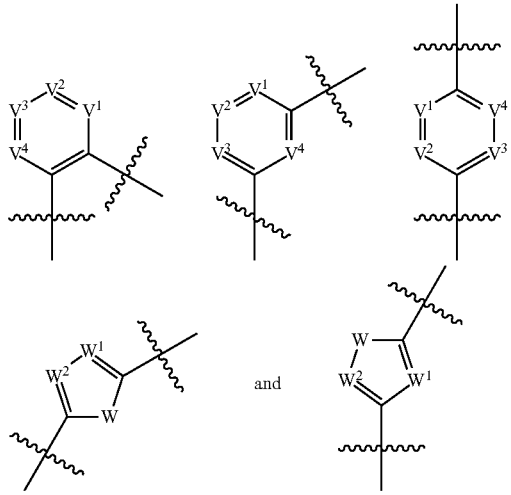

wherein V$^1$, V$^2$, V$^3$, V$^4$, W, W$^1$, W$^2$, R$^3$, R$^4$, R$^5$ and R$^6$ are as defined above.

In certain embodiments Ar$^1$ is selected from the group consisting of:

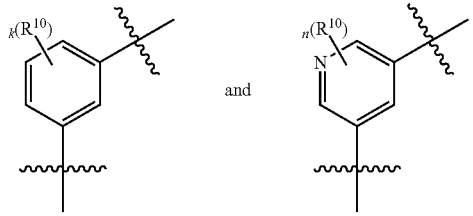

wherein each R$^{10}$ is independently as defined above, k is an integer selected from the group consisting of 0, 1, 2, 3, and 4; and n is an integer selected from the group consisting of 0, 1, and 2.

In yet an even further embodiment Ar$^1$ is selected from the group consisting of:

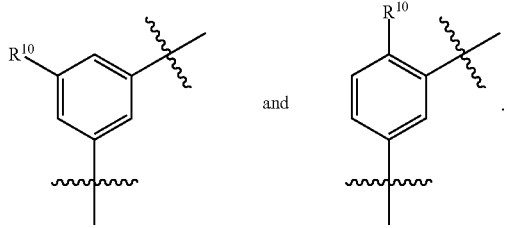

wherein R$^{10}$ is as defined above.

In certain embodiments Ar$^1$ is selected from the group consisting of:

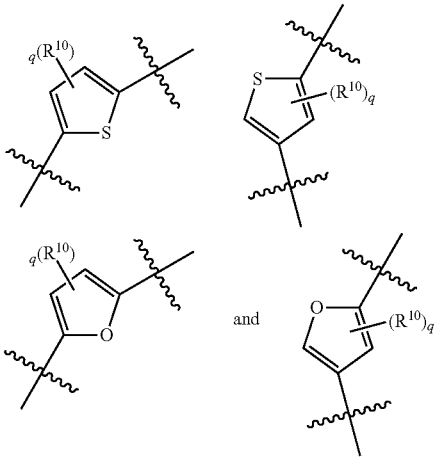

wherein each R$^{10}$ is independently as defined above, and q is an integer selected from the group consisting of 0, 1 and 2.

In certain embodiments Ar$^1$ is selected from the group consisting of:

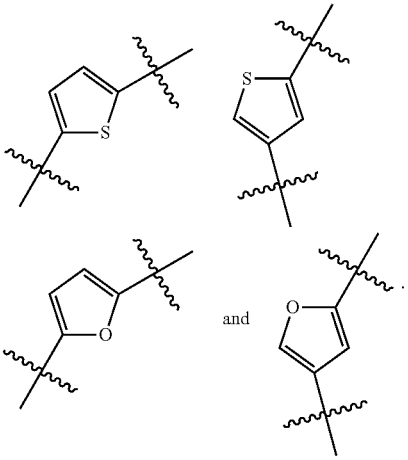

In certain embodiments Ar$^1$ is selected from the group consisting of:

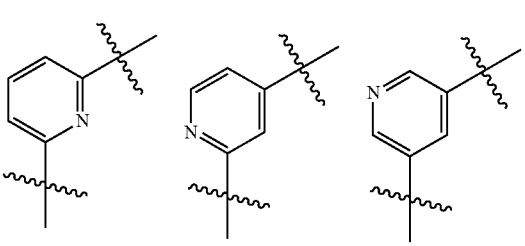

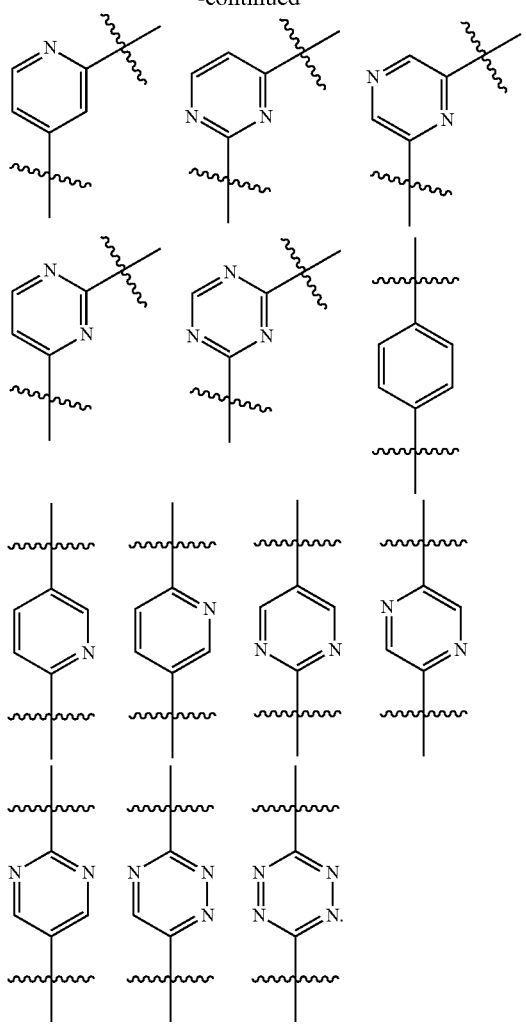

lkenyl, cycloalkylheteroalkyl, heterocycloalkylheteroalkyl, heteroarylheteroalkyl, arylheteroalkyl, hydroxy, hydroxyalkyl, alkoxy, alkoxyalkyl, alkoxyaryl, alkenyloxy, alkynyloxy, cycloalkylkoxy, heterocycloalkyloxy, aryloxy, arylalkyloxy, phenoxy, benzyloxy, heteroaryloxy, amino, alkylamino, aminoalkyl, acylamino, arylamino, sulfonylamino, sulfinylamino, —COOH, —COR³, —COOR³, —CONHR³, —NHCOR³, —NHCOOR³, —NHCONHR³, alkoxycarbonyl, alkylaminocarbonyl, sulfonyl, alkylsulfonyl, alkylsulfinyl, arylsulfonyl, arylsulfinyl, aminosulfonyl, —SR³, R⁴S(O)R⁶—, R⁴S(O)₂R⁶—, R⁴C(O)N(R⁵)R⁶—, R⁴SO₂N(R⁵)R⁶—, R⁴N(R⁵)C(O)R⁶—, R⁴N(R⁵)SO₂R⁶—, R⁴N(R⁵)C(O)N(R⁵)R⁶— and acyl, each of which may be optionally substituted.

In certain embodiments Ar² is selected from the group consisting of:

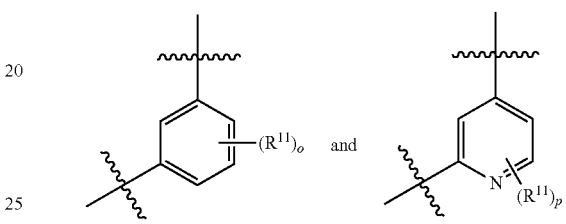

wherein each R¹¹ is independently as defined above
o is an integer selected from the group consisting of 0, 1, 2, 3, and 4; and
p is an integer selected from the group consisting of 0, 1, 2, and 3.

In certain embodiments Ar² is selected from the group consisting of:

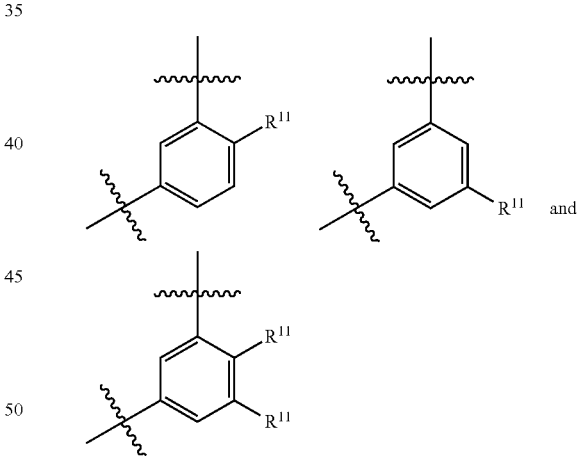

wherein each R¹¹ is as defined above.

In an even further embodiment Ar² is selected from the group consisting of:

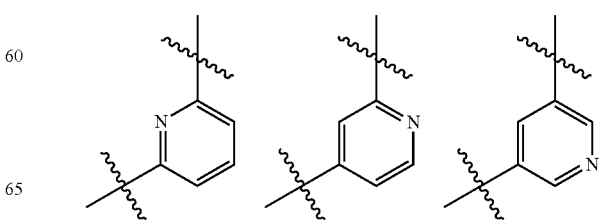

In certain embodiments Ar² is selected from the group consisting of:

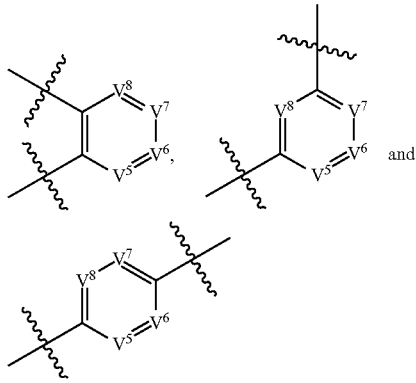

wherein V⁵, V⁶, V⁷ and V⁸ are independently selected from the group consisting of N, and C(R¹¹);
wherein each R¹¹ is independently selected from the group consisting of: H, halogen, alkyl, alkenyl, alkynyl, haloalkyl, haloalkenyl, heteroalkyl, cycloalkyl, cycloalkenyl, heterocycloalkyl, heterocycloalkenyl, aryl, heteroaryl, cycloalkylalkyl, heterocycloalkylalkyl, arylalkyl, heteroarylalkyl, aryla- -continued

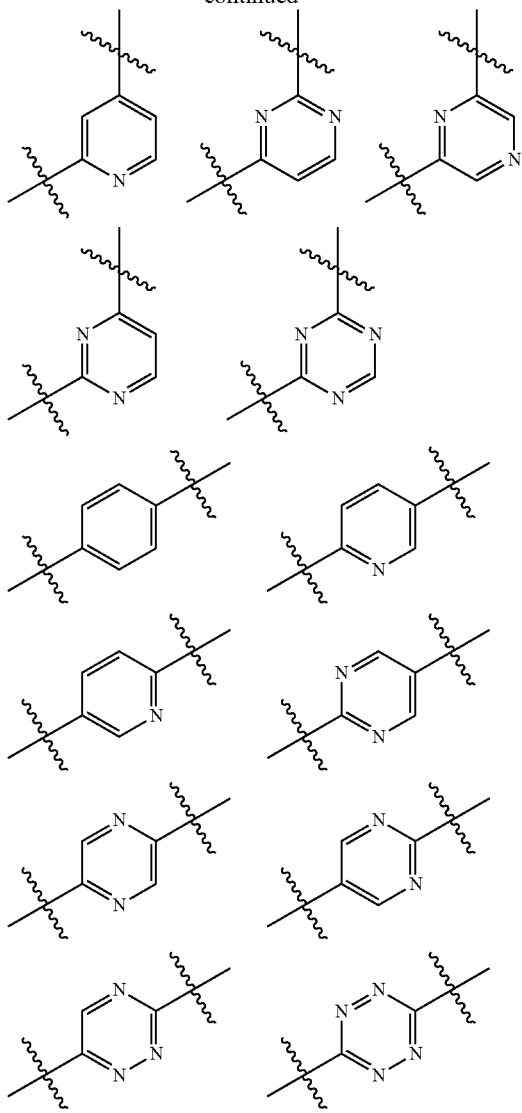

In one embodiment of the invention the compound is of the formula (II):

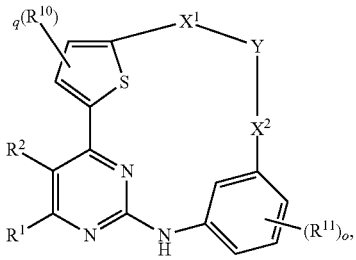

Formula (II)

or a pharmaceutically acceptable salt or prodrug thereof
wherein $R^1$, $R^2$, $R^{10}$, $R^{11}$ $X^1$, $X^2$, Y, k and o are as defined above.

In one embodiment of the invention the compound is of the formula (III):

Formula (III)

or a pharmaceutically acceptable salt or prodrug thereof
wherein $R^1$, $R^2$, $R^{10}$, $R^{11}$, $X^1$, $X^2$, Y, q and o are as defined above.

In one embodiment of the invention the compound is of the formula (IV):

Formula (IV)

or a pharmaceutically acceptable salt or prodrug thereof
wherein $R^1$, $R^2$, $R^{10}$, $R^{11}$, $X^1$, $X^2$, Y, q and o are as defined above.

In one embodiment of the invention the compound is of the formula (V):

Formula (V)

or a pharmaceutically acceptable salt or prodrug thereof
wherein $R^1$, $R^2$, $R^{10}$, $R^{11}$, $X^1$, $X^2$, Y, q and o are as defined above.

In one embodiment of the invention the compound is of the formula (VI):

Formula (VI)

or a pharmaceutically acceptable salt or prodrug thereof wherein $R^1$, $R^2$, $R^{10}$, $R^{11}$, $X^1$, $X^2$, Y, q and o are as defined above.

In one embodiment of the invention the compound is of the formula (VII):

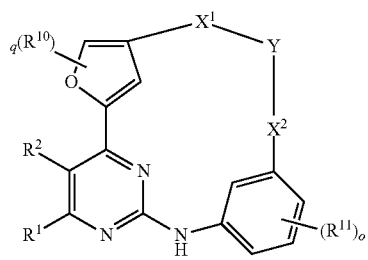

Formula (VII)

or a pharmaceutically acceptable salt or prodrug thereof
wherein $R^1$, $R^2$, $R^{10}$, $R^{11}$, $X^1$, $X^2$, Y, q and o are as defined above.

In the compounds of the invention $X^1$, $X^2$ and Y are chosen such that there are between 5 and 15 atoms in the normal chain. In one embodiment of the compounds of the invention $X^1$, $X^2$ and Y are chosen such that there are between 6 and 15 atoms in the normal chain. In one specific embodiment of the compounds of the invention $X^1$, $X^2$ and Y are chosen such that there are 7 atoms in the normal chain. In another specific embodiment of the compounds of the invention $X^1$, $X^2$ and Y are chosen such that there are 8 atoms in the normal chain.

In the compounds of the invention $X^1$ and $X^2$ are each independently a heteroalkyl group containing at least one oxygen atom in the normal chain.

In certain embodiments $X^1$ is selected from the group consisting of:
(a) —$OC_{1-5}$alkyl-,
(b) —$C_{1-5}$alkylO—, and
(c) —$C_{1-5}$alkylO$C_{1-5}$alkyl.

In certain embodiments $X^1$ is selected from the group consisting of:
(a) —OCH$_2$—
(b) —CH$_2$O—,
(c) —OCH$_2$CH$_2$—,
(d) —CH$_2$CH$_2$O—,
(e) —CH$_2$OCH$_2$—, and
(f) —CH$_2$CH$_2$OCH$_2$—.

In one specific embodiment $X^1$ is —OCH$_2$—. In another specific embodiment $X^1$ is —CH$_2$O—. In another specific embodiment $X^1$ is —OCH$_2$CH$_2$—. In another specific embodiment $X^1$ is —CH$_2$CH$_2$O—. In another specific embodiment $X^1$ is —CH$_2$OCH$_2$—. In another specific embodiment $X^1$ is —CH$_2$CH$_2$OCH$_2$—.

In certain embodiments $X^2$ is selected from the group consisting of:
(a) —$OC_{1-5}$alkyl-,
(b) —$C_{1-5}$alkylO—, and
(c) —$C_{1-5}$alkylO$C_{1-5}$alkyl.

In certain embodiments $X^2$ is selected from the group consisting of:
(a) —OCH$_2$—
(b) —CH$_2$O—,
(c) —OCH$_2$CH$_2$—,
(d) —CH$_2$CH$_2$O—,
(e) —CH$_2$OCH$_2$—, and
(f) —CH$_2$CH$_2$OCH$_2$—.

In one specific embodiment $X^2$ is —OCH$_2$—. In another specific embodiment $X^1$ is —CH$_2$O—. In another specific embodiment $X^2$ is —OCH$_2$CH$_2$—. In another specific embodiment $X^2$ is —CH$_2$CH$_2$O—. In another specific embodiment $X^2$ is —CH$_2$OCH$_2$—. In another specific embodiment $X^2$ is —CH$_2$CH$_2$OCH$_2$—.

A particularly useful subset of compounds of the invention are selected from the group consisting of:

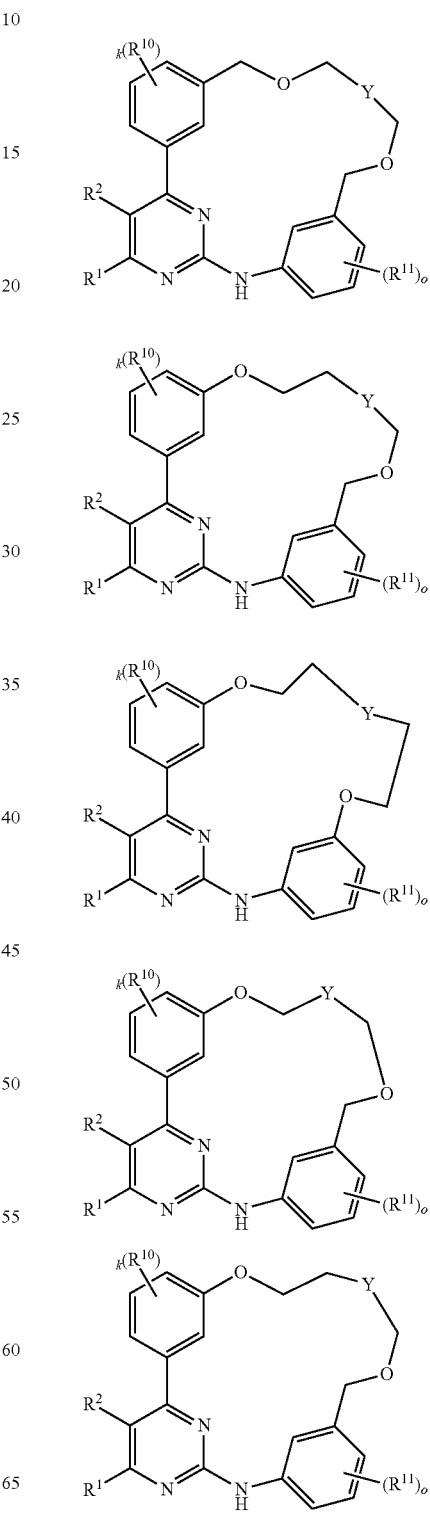

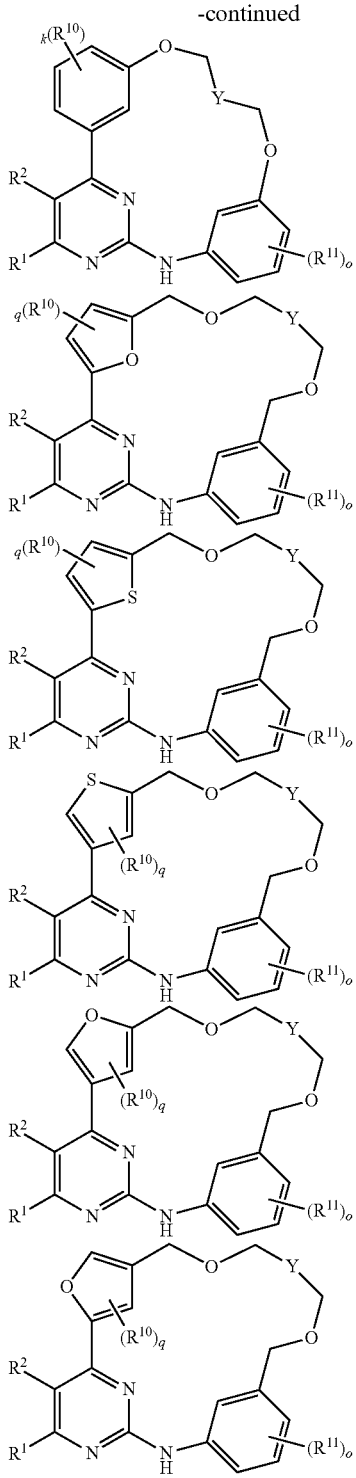

or a pharmaceutically acceptable salt thereof;
wherein $R^1$, $R^2$, $R^{10}$, k, Y, q and o are as defined above.

In certain embodiments $R^1$ is selected from the group consisting of H, halogen, alkyl, heteroalkyl, cycloalkyl, heterocycloalkyl, aryl, heteroaryl, cycloalkylalkyl, heterocycloalkylalkyl, arylalkyl, heteroarylalkyl, cycloalkylheteroalkyl, heterocycloalkylheteroalkyl, heteroarylheteroalkyl, arylheteroalkyl, hydroxy, hydroxyalkyl, alkoxy, alkoxyalky, cycloalkylkoxy, heterocycloalkyloxy, aryloxy, arylalkyloxy, phenoxy, benzyloxy, heteroaryloxy, amino, alkylamino, arylamino, sulfonylamino, sulfinylamino, COOH, $COR^3$, $COOR^3$, $CONHR^3$, $NHCOR^3$, $NHCOOR^3$, $NHCONHR^3$, alkoxycarbonyl, alkylaminocarbonyl, sulfonyl, alkylsulfonyl, alkylsulfinyl, arylsulfonyl, arylsulfinyl, aminosulfonyl, and acyl, each of which may be optionally substituted.

In certain embodiments of the invention $R^1$ is selected from the group consisting of H, chloro, bromo, iodo, methyl, ethyl, propyl, butyl, pentyl, hexyl, cyclopropyl, cyclobutyl, phenyl, hydroxy, methoxy, ethoxy, phenoxy, benzyloxy, amino, methylamino, ethylamino, propylamino, butylamino, pentylamino and hexylamino, each of which may be optionally substituted.

In certain embodiments $R^1$ is selected from the group consisting of H, chloro, bromo, iodo, amino, methylamino, ethylamino, propylamino, butylamino, pentylamino and hexylamino, each of which may be optionally substituted.

In a specific embodiment $R^1$ is H.

In certain embodiments $R^2$ is selected from the group consisting of H, halogen, alkyl, heteroalkyl, cycloalkyl, heterocycloalkyl, aryl, heteroaryl, cycloalkylalkyl, heterocycloalkylalkyl, arylalkyl, heteroarylalkyl, cycloalkylheteroalkyl, heterocycloalkylheteroalkyl, heteroarylheteroalkyl, arylheteroalkyl, hydroxy, hydroxyalkyl, alkoxy, alkoxyalky, cycloalkylkoxy, heterocycloalkyloxy, aryloxy, arylalkyloxy, phenoxy, benzyloxy, heteroaryloxy, amino, alkylamino, arylamino, sulfonylamino, sulfinylamino, COOH, $COR^3$, $COOR^3$, $CONHR^3$, $NHCOR^3$, $NHCOOR^3$, $NHCONHR^3$, alkoxycarbonyl, alkylaminocarbonyl, sulfonyl, alkylsulfonyl, alkylsulfinyl, arylsulfonyl, arylsulfinyl, aminosulfonyl, and acyl, each of which may be optionally substituted.

In certain embodiments $R^2$ is selected from the group consisting of H, chloro, bromo, iodo, methyl, ethyl, propyl, butyl, pentyl, hexyl, cyclopropyl, cyclobutyl, phenyl, hydroxy, methoxy, ethoxy, phenoxy, benzyloxy, amino, methylamino, ethylamino, propylamino, butylamino, pentylamino and hexylamino, each of which may be optionally substituted.

In certain embodiments $R^2$ is selected from the group consisting of H, chloro, bromo, iodo, amino, methylamino, ethylamino, propylamino, butylamino, pentylamino and hexylamino, each of which may be optionally substituted.

In one specific embodiment $R^2$ is selected from the group consisting of H and alkyl.

In another specific embodiment $R^2$ is H or methyl.

In certain embodiments $R^3$ is selected from the group consisting of H, $C_1$-$C_6$ alkyl and acyl. In another embodiment $R^3$ is selected from the group consisting of H and $C_1$-$C_4$ alkyl. In a specific embodiment $R^3$ is $C_1$-$C_4$ alkyl.

In certain embodiments $R^4$ is selected from the group consisting of H and $C_1$-$C_4$ alkyl. In a specific embodiment $R^4$ is $C_1$-$C_4$ alkyl.

In certain embodiments $R^5$ is selected from the group consisting of $C_1$-$C_4$ alkyl, heteroalkyl and acyl. In a specific embodiment $R^5$ is $C_1$-$C_4$ alkyl.

In certain embodiments $R^6$ is selected from the group consisting of a bond, $C_1$-$C_4$ alkyl, heteroalkyl and acyl. In specific embodiment $R^6$ is $C_1$-$C_4$ alkyl or a bond.

In certain embodiments $R^7$ is selected from the group consisting of H and $C_1$-$C_4$ alkyl. In a specific embodiment $R^7$ is H.

In certain embodiments of the compounds of the invention each $R^{10}$ is independently selected from the group consisting of H, halogen, amino, alkyl, haloalkyl, haloalkenyl, heterocycloalkyl, aryl, cycloalkylalkyl, heterocycloalkylalkyl, arylalkyl, heteroarylalkyl, cycloalkylheteroalkyl, heterocycloalkylheteroalkyl, heteroarylheteroalkyl, arylheteroalkyl, hydroxy, hydroxyalkyl, alkoxy, and alkoxyalkyl, each of which may be optionally substituted.

In certain embodiments each $R^{10}$ is independently selected from the group consisting of H, hydroxyl, fluoro, amino, methoxy, methyl, ethyl, propyl, butyl, pentyl, hexyl, phenyl, and 2-morpholino-ethoxy, each of which may be optionally substituted.

In certain embodiments each $R^{11}$ is independently selected from the group consisting of H, halogen, alkyl, amino, $NR^3R^4$, alkylsulfonyl, haloalkyl, heteroalkyl, haloalkenyl, heterocycloalkyl, aryl, cycloalkylalkyl, heterocycloalkylalkyl, arylalkyl, heteroarylalkyl, cycloalkylheteroalkyl, heterocycloalkylheteroalkyl, heteroarylheteroalkyl, arylsulfonyloxy, arylheteroalkyl, hydroxy, hydroxyalkyl, alkoxy, and alkoxyalkyl, each of which may be optionally substituted.

In certain embodiments each $R^{11}$ is independently selected from the group consisting of H, hydroxyl, methoxy, methyl, ethyl, propyl, butyl, pentyl, hexyl, phenyl, and 2-morpholino-ethoxy, each of which may be optionally substituted.

In certain embodiments of the invention each $R^{11}$ is independently selected from the group consisting of H, alkoxy, heteroalkyl, heterocycloalkyl, heterocycloalkylheteroalkyl and arylsulfonyloxy, each of which may be optionally substituted.

In certain embodiments of the invention k is 0 or 1. In one embodiment k is 0. In another embodiment k is 1.

In certain embodiments of the invention q is 0 or 1. In one embodiment q is 0. In another embodiment q is 1.

In certain embodiments of the invention o is 0, 1, or 2. In one embodiment o is one. In another embodiment o is 1. In another embodiment o is 2.

In certain embodiments of the invention each $R^{11}$ is independently selected from the group consisting of:

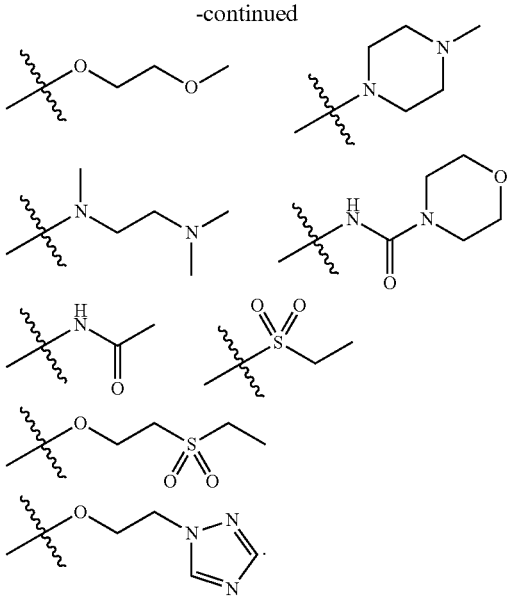

In one embodiment Y is selected from the group consisting of:

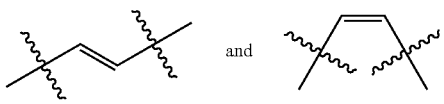

In a specific embodiment Y is

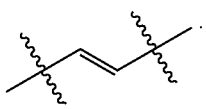 [SMILES: */C=C/*]

In another specific embodiment Y is

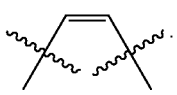

In another specific embodiment Y is a cyclopropyl group.

Many if not all of the variables discussed above may be optionally substituted. If the variable is optionally substituted then in certain embodiments the optional substituent is selected from the group consisting of: halogen, =O, =S, —CN, —NO$_2$, —CF$_3$, —OCF$_3$, alkyl, alkenyl, alkynyl, haloalkyl, haloalkenyl, haloalkynyl, heteroalkyl, cycloalkyl, cycloalkenyl, heterocycloalkyl, heterocycloalkenyl, aryl, heteroaryl, hydroxy, hydroxyalkyl, alkoxy, alkoxyalkyl, alkoxyaryl, alkoxyheteroaryl, alkenyloxy, alkynyloxy, cycloalkyloxy, cycloalkenyloxy, heterocycloalkyloxy, heterocycloalkenyloxy, aryloxy, heteroaryloxy, arylalkyl, heteroarylalkyl, arylalkyloxy, -amino, alkylamino, acylamino, aminoalkyl, arylamino, sulfonyl, alkylsulfonyl, arylsulfonyl, aminosulfonyl, aminoalkyl, alkoxyalky, —COOH, —COR$^5$, —C(O)OR$^5$, —SH, —SR$^5$, —OR$^6$, and acyl.

In certain embodiments the substituents are selected from the group consisting of: halogen, =O, =S, —CN, —NO$_2$, alkyl, alkenyl, heteroalkyl, haloalkyl, alkynyl, aryl, cycloalkyl, heterocycloalkyl, heteroaryl, hydroxy, hydroxyalkyl, alkoxy, alkylamino, aminoalkyl, acylamino, phenoxy, alkoxyalkyl, benzyloxy, alkylsulfonyl, arylsulfonyl, aminosulfonyl, —C(O)OR$^5$, COOH, SH, and acyl.

In addition to compounds of Formula I, the embodiments disclosed are also directed to pharmaceutically acceptable salts, pharmaceutically acceptable N-oxides, pharmaceutically acceptable prodrugs, and pharmaceutically active metabolites of such compounds, and pharmaceutically acceptable salts of such metabolites.

The invention also relates to pharmaceutical compositions including a compound of the invention with a pharmaceutically acceptable carrier, diluent or excipient.

In a further aspect the invention provides a method of inhibiting one or more protein kinase(s) including exposing the one or more protein kinase(s) and/or co-factor(s) thereof to an effective amount of a compound of the invention. In one embodiment the compound is a compound of formula (I), (II), (III), (IV), (V), (VI) or (VII).

The compounds disclosed herein may act directly and solely on the kinase molecule to inhibit biological activity. However, it is understood that the compounds may also act at least partially on co-factors that are involved in the phosphorylation process. For example, where the kinase is cyclin-dependent, a co-factor such as cyclinA is involved in the transfer of phosphate from ATP (also considered a co-factor in itself) to the substrate molecule. Other kinase co-factors include ionic species (such as zinc and calcium), lipids (such as phosphatidylserine), and diacylglycerols.

In one embodiment of the method the one or more protein kinase(s) is a cyclin-dependent protein kinase. In a specific embodiment the cyclin-dependent kinase is a Group I CMCG kinase. In one embodiment the Group I CMCG kinase is selected from the group consisting of CDC2Hs, CDK2, CDK3, CDK4, CDK5, CDK6, CDK9, PCTAIRE1, PCTAIRE2, PCTAIRE3, CAK/MO15, Dm2, Dm2c, Ddcdc2, DdPRK, LmmCRK1, PfC2R, EhC2R, CfCdc2R, cdc2+, CDC28, PHO85, KIN28, FpCdc2, MsCdc2B, and OsC2R or a functional equivalent thereof. In a specific embodiment the Group I CMCG kinase is CDK2 or a functional equivalent thereof.

In another embodiment of the method the one or more protein kinase(s) is a protein tyrosine kinase. In one form of this embodiment the protein tyrosine kinase is a Group VII protein tyrosine kinase. In one embodiment the Group VII protein tyrosine kinase is selected from the group consisting of TYK2, JAK1, JAK2 and HOP or a functional equivalent thereof. In a specific embodiment the Group VII protein tyrosine kinase is JAK2 or a functional equivalent thereof. In one form of the method, the JAK2 includes a recurrent unique acquired clonal mutation. This mutation is observed in a majority of polycythemia vera (PV) patients and a significant proportion of patients with other myeloproliferative disorders, including, essential thrombocythemia (ET) and chronic idiopathic myelofibrosis (IMF). In one form of the method the mutation is a valine to phenylalanine substitution at position 617 (V617F). The incidence of this mutation in PV patients is very high (around 78% of patients).

The JAK2 mutation is somatic and occurs at the level of a hematopoietic stem cell. Studies have demonstrated that the mutated JAK2 was found in myeloid cells, i.e., bone marrow cells, granulocytes, platelets and erythroblasts derived from CD34+ cells, but not in T cells. In addition, mutant JAK2 was found in hematopoietic colonies derived from hematopoietic progenitor cells. Applicant has demonstrated that kinase inhibitors described herein are capable of inhibiting the activity of wild type and mutant JAK2.

In another embodiment of the method the protein tyrosine kinase is a Group XIV protein tyrosine kinase. In one form of this embodiment the Group XIV protein tyrosine kinase is selected from the group consisting of PDGFR-b, PDGFR-a, CSF1R, c-kit, Flk2, FLT1, FLT2, FLT3 and FLT4 or a functional equivalent thereof. In one specific embodiment the Group XIV protein tyrosine kinase is FLT3 or a functional equivalent thereof. In another form of the method, the FLT3 kinase includes a mutation. There is substantial experimental and clinical evidence to support the hypothesis that FLT3 mutations are important in the initiation or maintenance of AML in some patients. Activating mutations of FLT3 result in constitutive activation of FLT3 tyrosine kinase activity and can transform factor-dependent hematopoietic cells as evidenced by conversion to factor-independent growth and formation of tumours in immunodeficient mice. In addition, retroviral transduction of primary murine bone marrow with an AML patient-derived FLT3 ITD (internal tandem duplication) cDNA results in a lethal myeloproliferative syndrome. Furthermore, retroviral transduction of bone marrow derived from promyelocytic leukemia/retinoic acid receptor (PML-RAR) transgenic mice with FLT3 ITD results in a marked increase in the incidence of acute progranulocytic (APL)-like leukemia in such mice when compared with mice that received a transplant of mock-transduced bone marrow. Applicants have demonstrated that kinase inhibitors described herein are capable of inhibiting FLT3 including an ITD where there is a duplication of amino acids VDFREYEYDH at amino acid position 592-601. In an even more specific embodiment of the method the FLT3 includes an internal tandem duplication. In an even more specific embodiment the internal tandem duplication is a duplication of amino acids VDFREYEYDH at position 592-601.

In one embodiment of the method exposing the one or more protein kinase(s) to the compound includes administering the compound to a mammal containing the one or more protein kinase(s).

In one embodiment the one or more protein kinase(s) include at least two kinases selected from the group consisting of CDK2, FLT3 and JAK2 or functional equivalents thereof. In one form of this embodiment the one or more protein kinase(s) include all three of CDK2, FLT3 and JAK2 or functional equivalents thereof.

In an even further aspect the invention provides the use of a compound of the invention to inhibit one or more protein kinase(s). In one embodiment the compound is a compound of formula (I), (II), (III), (IV), (V), (VI) or (VII).

In one embodiment the one or more protein kinase(s) is a cyclin-dependent protein kinase. In a specific embodiment the cyclin-dependent kinase is a Group I CMCG kinase. In one embodiment the Group I CMCG kinase is selected from the group consisting of CDC2Hs, CDK2, CDK3, CDK4, CDK5, CDK6, CDK9, PCTAIRE1, PCTAIRE2, PCTAIRE3, CAK/MO15, Dm2, Dm2c, Ddcdc2, DdPRK, LmmCRK1, PfC2R, EhC2R, CfCdc2R, cdc2+, CDC28, PHO85, KIN28, FpCdc2, MsCdc2B, and OsC2R and functional equivalents thereof. In a specific embodiment the Group I CMCG kinase is CDK2 or a functional equivalent thereof.

In another embodiment the one or more protein kinase(s) is a protein tyrosine kinase. In one form of this embodiment the protein tyrosine kinase is a Group VII protein tyrosine kinase. In one embodiment the Group VII protein tyrosine kinase is selected from the group consisting of TYK2, JAK1, JAK2 and HOP or a functional equivalent thereof. In a specific embodiment the Group VII protein tyrosine kinase is JAK2 or a functional equivalent thereof. In a more specific embodiment the JAK2 includes a V to F mutation at position 617.

In another embodiment the protein tyrosine kinase is a Group XIV protein tyrosine kinase. In one form of this embodiment the Group XIV protein tyrosine kinase is selected from the group consisting of PDGFR-b, PDGFR-a, CSF1R, c-kit, Flk2, FLT1, FLT2, FLT3 and FLT4 or a functional equivalent thereof. In one specific embodiment the Group XIV protein tyrosine kinase is FLT3 or a functional equivalent thereof. In an even more specific embodiment FLT3 includes an internal tandem duplication. In an even more specific embodiment the internal tandem duplication is a duplication of amino acids VDFREYEYDH at position 592-601.

In one embodiment the one or more protein kinase(s) include at least two kinases selected from the group consisting of CDK2, FLT3 and JAK2 or functional equivalents thereof. In one form of this embodiment the one or more protein kinase(s) include all three of CDK2, FLT3 and JAK2 or functional equivalents thereof.

In an even further aspect the invention provides a method of treating or preventing a condition in a mammal in which inhibition of one or more protein kinase(s) and/or co-factor(s) thereof prevents, inhibits or ameliorates a pathology or a symptomology of the condition, the method including administration of a therapeutically effective amount of a compound of the invention. In one embodiment the compound is a compound of formula (I), (II), (III), (IV), (V), (VI) or (VII).

In one embodiment of the method the one or more protein kinase(s) is a cyclin-dependent protein kinase. In a specific embodiment the cyclin-dependent kinase is a Group I CMCG kinase. In one embodiment the Group I CMCG kinase is selected from the group consisting of CDC2Hs, CDK2, CDK3, CDK4, CDK5, CDK6, CDK9, PCTAIRE1, PCTAIRE2, PCTAIRE3, CAK/MO15, Dm2, Dm2c, Ddcdc2, DdPRK, LmmCRK1, PfC2R, EhC2R, CfCdc2R, cdc2+, CDC28, PHO85, KIN28, FpCdc2, MsCdc2B, and OsC2R or a functional equivalent thereof. In a specific embodiment the Group I CMCG kinase is CDK2 or a functional equivalent thereof. In one embodiment the condition is selected from the group consisting of prostate cancer, retinoblastoma, malignant neoplasm of breast, malignant tumour of colon, endometrial hyperplasia, osteosarcoma, squamous cell carcinoma, non-small cell lung cancer, melanoma, liver cell carcinoma, malignant neoplasm of pancreas, myeloid leukemia, cervical carcinoma, fibroid tumour, adenocarcinoma of the colon, T-cell leukemia, glioma, glioblastoma, oligodendroglioma, lymphoma, ovarian cancer, restenosis, astrocytoma, bladder neoplasms, musculoskeletal neoplasms and Alzheimer's Disease.

In another embodiment of the method the one or more protein kinase(s) is a protein tyrosine kinase. In one form of this embodiment the protein tyrosine kinase is a Group VII protein tyrosine kinase. In one embodiment the Group VII protein tyrosine kinase is selected from the group consisting of TYK2, JAK1, JAK2 and HOP or a functional equivalent thereof. In a specific embodiment the Group VII protein tyrosine kinase is JAK2 or a functional equivalent thereof. In a more specific embodiment the JAK2 includes a V to F mutation at position 617. In one embodiment the condition is selected from the group consisting of Myeloproliferative disorders (chronic idiopathic myelofibrosis, polycythemia vera, essential thrombocythemia, chronic myeloid leukemia), myeloid metaplasia, chronic myelomonocytic leukemia, acute lymphocytic leukemia, acute erythroblastic leukemia, Hodgkin's disease, B-cell lymphoma, acute T-cell leukemia, breast carcinoma, ovarian cancer, colon carcinoma, prostate cancer, melanoma, myelodysplastic syndromes, keloids, congestive heart failure, ischemia, thrombosis, cardiac hypertrophy, pulmonary hypertension, and retinal degeneration.

In another embodiment of the method the protein tyrosine kinase is a Group XIV protein tyrosine kinase. In one form of this embodiment the Group XIV protein tyrosine kinase is selected from the group consisting of PDGFR-b, PDGFR-a, CSF1R, c-kit, Flk2, FLT1, FLT2, FLT3 and FLT4 or a functional equivalent thereof. In one specific embodiment the Group XIV protein tyrosine kinase is FLT3 or a functional equivalent thereof. In an even more specific embodiment FLT3 includes an internal tandem duplication. In an even more specific embodiment the internal tandem duplication is a duplication of amino acids VDFREYEYDH at position 592-601. In one embodiment the condition is selected from the group consisting of acute myeloid leukemia, acute promyelocytic leukemia, acute lymphocytic leukemia, myelodysplastic syndromes, leukocytosis, juvenile myelomonocytic leukemia, acute B-cell leukemia, chronic myeloid leukemia, acute T-cell leukemia, myeloproliferative disorders, and chronic myelomonocytic leukemia.

In one embodiment the one or more protein kinase(s) include at least two kinases selected from the group consisting of CDK2, FLT3 and JAK2 or functional equivalents thereof. In one form of this embodiment the one or more protein kinase(s) include all three of CDK2, FLT3 and JAK2 or functional equivalents thereof.

In an even further aspect the invention provides the use of a compound of the invention in the preparation of a medicament for treating a condition in an animal in which inhibition of one or more protein kinase(s) can prevent, inhibit or ameliorate the pathology or symptomology of the condition. In one embodiment the compound is a compound of formula (I), (II), (III), (IV), (V), (VI) or (VII).

In one embodiment the one or more protein kinase(s) is a cyclin-dependent protein kinase. In a specific embodiment the cyclin-dependent kinase is a Group I CMCG kinase. In one embodiment the Group I CMCG kinase is selected from the group consisting of CDC2Hs, CDK2, CDK3, CDK4, CDK5, CDK6, CDK9, PCTAIRE1, PCTAIRE2, PCTAIRE3, CAK/MO15, Dm2, Dm2c, Ddcdc2, DdPRK, LmmCRK1, PfC2R, EhC2R, CfCdc2R, cdc2+, CDC28, PHO85, KIN28, FpCdc2, MsCdc2B, and OsC2R or a functional equivalent thereof. In a specific embodiment the Group I CMCG kinase is CDK2 or a functional equivalent thereof. In one embodiment the condition is selected from the group consisting of prostate cancer, retinoblastoma, malignant neoplasm of breast, malignant tumour of colon, endometrial hyperplasia, osteosarcoma, squamous cell carcinoma, non-small cell lung cancer, melanoma, liver cell carcinoma, malignant neoplasm of pancreas, myeloid leukemia, cervical carcinoma, fibroid tumour, adenocarcinoma of the colon, T-cell leukemia, glioma, glioblastoma, oligodendroglioma, lymphoma, ovarian cancer, restenosis, astrocytoma, bladder neoplasms, musculoskeletal neoplasms and Alzheimer's Disease.

In another embodiment the one or more protein kinase(s) is a protein tyrosine kinase. In one form of this embodiment the protein tyrosine kinase is a Group VII protein tyrosine kinase. In one embodiment the Group VII protein tyrosine kinase is selected from the group consisting of TYK2, JAK1, JAK2 and HOP or a functional equivalent thereof. In a specific embodiment the Group VII protein tyrosine kinase is JAK2 or a functional equivalent thereof. In a more specific embodiment the JAK2 includes a V to F mutation at position 617. In one embodiment the condition is selected from the group consisting of Myeloproliferative disorders (chronic idiopathic myelofibrosis, polycythemia vera, essential thrombocythemia, chronic myeloid leukemia), myeloid metaplasia, chronic myelomonocytic leukemia, acute lymphocytic leukemia, acute erythroblastic leukemia, Hodgkin's disease, B-cell lymphoma, acute T-cell leukemia, breast carcinoma, ovarian cancer, colon carcinoma, prostate cancer, melanoma, myelodysplastic syndromes, keloids, congestive heart failure, ischemia, thrombosis, cardiac hypertrophy, pulmonary hypertension, and retinal degeneration.

In another embodiment the protein tyrosine kinase is a Group XIV protein tyrosine kinase. In one form of this embodiment the Group XIV protein tyrosine kinase is selected from the group consisting of PDGFR-b, PDGFR-a, CSF1R, c-kit, Flk2, FLT1, FLT2, FLT3 and FLT4 or a functional equivalent thereof. In one specific embodiment the Group XIV protein tyrosine kinase is FLT3 or a functional equivalent thereof. In an even more specific embodiment FLT3 includes an internal tandem duplication. In an even more specific embodiment the internal tandem duplication is a duplication of amino acids VDFREYEYDH at position 592-601. In one embodiment the condition is selected from the group consisting of acute myeloid leukemia, acute promyelocytic leukemia, acute lymphocytic leukemia, myelodysplastic syndromes, leukocytosis, juvenile myelomonocytic leukemia, acute B-cell leukemia, chronic myeloid leukemia, acute T-cell leukemia, myeloproliferative disorders, and chronic myelomonocytic leukemia.

In one embodiment the one or more protein kinase(s) include at least two kinases selected from the group consisting of CDK2, FLT3 and JAK2 or functional equivalents thereof. In one form of this embodiment the one or more protein kinase(s) include all three of CDK2, FLT3 and JAK2 or functional equivalents thereof.

In an even further aspect the invention provides the use of a compound of the invention in the preparation of a medicament for the treatment or prevention of a kinase-related disorder. In one embodiment the compound is a compound of formula (I), (II), (III), (IV), (V), (VI) or (VII).

In one embodiment the kinase-related disorder is a proliferative disorder. In a specific embodiment the proliferative disorder is elected from the group consisting of myeloproliferative disorders (chronic idiopathic myelofibrosis, polycythemia vera, essential thrombocythemia, chronic myeloid leukemia), myeloid metaplasia, chronic myelomonocytic leukemia, acute myeloid leukemia, juvenile myelomonocytic leukemia, acute promyelocytic leukemia, acute lymphocytic leukemia, acute erythroblastic leukemia, acute B-cell leukemia, leukocytosis, Hodgkin's disease, B-cell lymphoma, acute T-cell leukemia, breast carcinoma, ovarian cancer, colon carcinoma, prostate cancer, melanoma, myelodysplastic syndromes, keloids, retinoblastoma, malignant neoplasm of breast, malignant tumour of colon, endometrial hyperplasia, osteosarcoma, squamous cell carcinoma, non-small cell lung cancer, melanoma, liver cell carcinoma, malignant neoplasm of pancreas, myeloid leukemia, cervical carcinoma, fibroid tumour, adenocarcinoma of the colon, glioma, glioblastoma, oligodendroglioma, lymphoma, ovarian cancer, restenosis, astrocytoma, bladder neoplasms, and musculoskeletal neoplasms.

In one embodiment the proliferative disorder is a myeloproliferative disorder. In a specific embodiment the myeloproliferative disorder is selected from the group consisting of polycythemia vera, essential thrombocythemia and idiopathic myelofibrosis.

In another embodiment the proliferative disorder is cancer. In one embodiment the cancer is a solid tumour. In one embodiment the solid tumour is a tumour present in or metastasized from an organ or tissue selected from the group consisting of breast, ovary, colon, prostate, endometrium, bone, skin, lung, liver, pancreas, cervix, brain, neural tissue, lymphatic tissue, blood vessel, bladder and muscle.

In one embodiment the cancer is a hematological cancer. In a specific embodiment the hematological cancer is selected from the group consisting of acute myeloid leukemia, acute promyelocytic leukemia, acute lymphocytic leukemia, myelodysplastic syndrome, leukocytosis, juvenile myelomonocytic leukemia, acute B-cell leukemia, chronic myeloid leukemia, acute T-cell leukemia, chronic myelomonocytic leukemia, myeloid metaplasia, chronic myelomonocytic leukemia, acute erythroblastic leukemia, Hodgkin's disease, and B-cell lymphoma.

In another embodiment, the kinase-related disorder is a cardiovascular disorder. In one embodiment the cardiovascular disorder is selected from the group consisting of congestive heart failure, ischemia, thrombosis, cardiac hypertrophy and restenosis.

In one embodiment the kinase-related disorder is a neurodegenerative disorder. In a specific embodiment the neurodegenerative disorder is Alzheimer's disease.

In an even further aspect the invention provides a method of treating or preventing a kinase-related disorder including administration of a therapeutically effective amount of a compound of the invention to a patient in need thereof. In one embodiment the compound is a compound of formula (I), (II), (III), (IV), (V), (VI) or (VII).

In one embodiment the kinase-related disorder is a proliferative disorder. In a specific embodiment the proliferative disorder is elected from the group consisting of myeloproliferative disorders (chronic idiopathic myelofibrosis, polycythemia vera, essential thrombocythemia, chronic myeloid leukemia), myeloid metaplasia, chronic myelomonocytic leukemia, acute myeloid leukemia, juvenile myelomonocytic leukemia, acute promyelocytic leukemia, acute lymphocytic leukemia, acute erythroblastic leukemia, acute B-cell leukemia, leukocytosis, Hodgkin's disease, B-cell lymphoma, acute T-cell leukemia, breast carcinoma, ovarian cancer, colon carcinoma, prostate cancer, melanoma, myelodysplastic syndromes, keloids, retinoblastoma, malignant neoplasm of breast, malignant tumour of colon, endometrial hyperplasia, osteosarcoma, squamous cell carcinoma, non-small cell lung cancer, melanoma, liver cell carcinoma, malignant neoplasm of pancreas, myeloid leukemia, cervical carcinoma, fibroid tumour, adenocarcinoma of the colon, glioma, glioblastoma, oligodendroglioma, lymphoma, ovarian cancer, restenosis, astrocytoma, bladder neoplasms, and musculoskeletal neoplasms.

In one embodiment the proliferative disorder is a myeloproliferative disorder. In a specific embodiment the myeloproliferative disorder is selected from the group consisting of polycythemia vera, essential thrombocythemia and idiopathic myelofibrosis.

In another embodiment the proliferative disorder is cancer. In one embodiment the cancer is a solid tumour. In one embodiment the solid tumour is a tumour present in or metastasized from an organ or tissue selected from the group consisting of breast, ovary, colon, prostate, endometrium, bone, skin, lung, liver, pancreas, cervix, brain, neural tissue, lymphatic tissue, blood vessel, bladder and muscle.

In one embodiment the cancer is a hematological cancer. In a specific embodiment the hematological cancer is selected from the group consisting of acute myeloid leukemia, acute promyelocytic leukemia, acute lymphocytic leukemia, myelodysplastic syndrome, leukocytosis, juvenile myelomonocytic leukemia, acute B-cell leukemia, chronic myeloid leukemia, acute T-cell leukemia, chronic myelomonocytic leukemia, myeloid metaplasia, chronic myelomonocytic leukemia, acute erythroblastic leukemia, Hodgkin's disease, and B-cell lymphoma.

In another embodiment, the kinase-related disorder is a cardiovascular disorder. In one embodiment the cardiovascular disorder is selected from the group consisting of congestive heart failure, ischemia, thrombosis, cardiac hypertrophy and restenosis.

In one embodiment the kinase-related disorder is a neurodegenerative disorder. In a specific embodiment the neurodegenerative disorder is Alzheimer's disease.

The invention also provides a method for inhibiting cell proliferation including administration of an effective amount of a compound according to formula (I). In one embodiment the compound is a compound of formula (II), (III), (IV), (V), (VI) or (VII).

In an even further aspect the invention provides a method of synthesis of a compound of formula (I) the method including the steps of:

(a) providing a compound of the formula

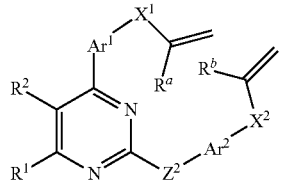

wherein $R^1$, $R^2$, $R^a$, $R^b$, $Z^2$, $Ar^1$, $Ar^2$, $X^1$ and $X^2$ are as defined above;

(b) subjecting the compound to ring closing metathesis;

(c) optionally reacting the double bond thus formed to form a cycloalkyl group.

DETAILED DESCRIPTION OF THE INVENTION

In this specification a number of terms are used which are well known to a skilled addressee. Nevertheless for the purposes of clarity a number of terms will be defined.

As used herein, the term unsubstituted means that there is no substituent or that the only substituents are hydrogen.

The term "optionally substituted" as used throughout the specification denotes that the group may or may not be further substituted or fused (so as to form a condensed polycyclic system), with one or more non-hydrogen substituent groups. In certain embodiments the substituent groups are one or more groups independently selected from the group consisting of halogen, =O, =S, —CN, —$NO_2$, —$CF_3$, —$OCF_3$, alkyl, alkenyl, alkynyl, haloalkyl, haloalkenyl, haloalkynyl, heteroalkyl, cycloalkyl, cycloalkenyl, heterocycloalkyl, heterocycloalkenyl, aryl, heteroaryl, cycloalkylalkyl, heterocycloalkylalkyl, heteroarylalkyl, arylalkyl, cycloalkylalkenyl, heterocycloalkylalkenyl, arylalkenyl, heteroarylalkenyl, cycloalkylheteroalkyl, heterocycloalkylheteroalkyl, arylheteroalkyl, heteroarylheteroalkyl, hydroxy, hydroxyalkyl, alkoxy, alkoxyalkyl, alkoxycycloalkyl, alkoxyheterocycloalkyl, alkoxyaryl, alkoxyheteroaryl, alkoxycarbonyl, alkylaminocarbonyl, alkenyloxy, alkynyloxy, cycloalkyloxy, cycloalkenyloxy, heterocycloalkyloxy, heterocycloalkenyloxy, aryloxy, phenoxy, benzyloxy, heteroaryloxy, arylalkyloxy, arylalkyl, heteroarylalkyl, cycloalkylalkyl, heterocycloalkylalkyl, arylalkyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, alkylsulfinyl, arylsulfinyl, aminosulfinylaminoalkyl, —COOH, —$COR^5$, —$C(O)OR^5$, $CONHR^5$, $NHCOR^5$, $NHCOOR^5$, $NHCONHR^5$, $C(=NOH)R^5$, —SH, —$SR^5$, —$OR^5$, and acyl.

"Alkyl" as a group or part of a group refers to a straight or branched aliphatic hydrocarbon group, preferably a $C_1$-$C_{14}$ alkyl, more preferably $C_1$-$C_{10}$ alkyl, most preferably $C_1$-$C_6$ unless otherwise noted. Examples of suitable straight and branched $C_1$-$C_6$ alkyl substituents include methyl, ethyl, n-propyl, 2-propyl, n-butyl, sec-butyl, t-butyl, hexyl, and the like. The group may be a terminal group or a bridging group.

"Alkylamino" includes both mono-alkylamino and dialkylamino, unless specified. "Mono-alkylamino" means a —NH-Alkyl group, in which alkyl is as defined above. "Dialkylamino" means a —N(alkyl)$_2$ group, in which each alkyl may be the same or different and are each as defined herein for alkyl. The alkyl group is preferably a $C_1$-$C_6$ alkyl group. The group may be a terminal group or a bridging group.

"Arylamino" includes both mono-arylamino and di-arylamino unless specified. Mono-arylamino means a group of formula arylNH—, in which aryl is as defined herein. di-arylamino means a group of formula (aryl)$_2$N— where each aryl may be the same or different and are each as defined herein for aryl. The group may be a terminal group or a bridging group.

"Acyl" means an alkyl-CO— group in which the alkyl group is as described herein. Examples of acyl include acetyl and benzoyl. The alkyl group is preferably a $C_1$-$C_6$ alkyl group. The group may be a terminal group or a bridging group.

"Alkenyl" as a group or part of a group denotes an aliphatic hydrocarbon group containing at least one carbon-carbon double bond and which may be straight or branched preferably having 2-14 carbon atoms, more preferably 2-12 carbon atoms, most preferably 2-6 carbon atoms, in the normal chain. The group may contain a plurality of double bonds in the normal chain and the orientation about each is independently E or Z. Exemplary alkenyl groups include, but are not limited to, ethenyl, propenyl, butenyl, pentenyl, hexenyl, heptenyl, octenyl and nonenyl. The group may be a terminal group or a bridging group.

"Alkoxy" refers to an —O-alkyl group in which alkyl is defined herein. Preferably the alkoxy is a $C_1$-$C_6$alkoxy. Examples include, but are not limited to, methoxy and ethoxy. The group may be a terminal group or a bridging group.

"Alkenyloxy" refers to an —O— alkenyl group in which alkenyl is as defined herein. Preferred alkenyloxy groups are $C_1$-$C_6$ alkenyloxy groups. The group may be a terminal group or a bridging group.

"Alkynyloxy" refers to an —O-alkynyl group in which alkynyl is as defined herein. Preferred alkynyloxy groups are $C_1$-$C_6$ alkynyloxy groups. The group may be a terminal group or a bridging group.

"Alkoxycarbonyl" refers to an —C(O)—O-alkyl group in which alkyl is as defined herein. The alkyl group is preferably a $C_1$-$C_6$ alkyl group. Examples include, but not limited to, methoxycarbonyl and ethoxycarbonyl. The group may be a terminal group or a bridging group.

"Alkylsulfinyl" means a —S(O)-alkyl group in which alkyl is as defined above. The alkyl group is preferably a $C_1$-$C_6$ alkyl group. Exemplary alkylsulfinyl groups include, but not limited to, methylsulfinyl and ethylsulfinyl. The group may be a terminal group or a bridging group.

"Alkylsulfonyl" refers to a —S(O)$_2$-alkyl group in which alkyl is as defined above. The alkyl group is preferably a $C_1$-$C_6$ alkyl group. Examples include, but not limited to methylsulfonyl and ethylsulfonyl. The group may be a terminal group or a bridging group.

"Alkynyl" as a group or part of a group means an aliphatic hydrocarbon group containing a carbon-carbon triple bond and which may be straight or branched preferably having from 2-14 carbon atoms, more preferably 2-12 carbon atoms, more preferably 2-6 carbon atoms in the normal chain. Exemplary structures include, but are not limited to, ethynyl and propynyl. The group may be a terminal group or a bridging group.

"Alkylaminocarbonyl" refers to an alkylamino-carbonyl group in which alkylamino is as defined above. The group may be a terminal group or a bridging group.

"Cycloalkyl" refers to a saturated or partially saturated, monocyclic or fused or spiro polycyclic, carbocycle preferably containing from 3 to 9 carbons per ring, such as cyclopropyl, cyclobutyl, cyclopentyl, cyclohexyl and the like, unless otherwise specified. It includes monocyclic systems such as cyclopropyl and cyclohexyl, bicyclic systems such as decalin, and polycyclic systems such as adamantane. The group may be a terminal group or a bridging group.

"Cycloalkenyl" means a non-aromatic monocyclic or multicyclic ring system containing at least one carbon-carbon double bond and preferably having from 5-10 carbon atoms per ring. Exemplary monocyclic cycloalkenyl rings include cyclopentenyl, cyclohexenyl or cycloheptenyl. The cycloalkenyl group may be substituted by one or more substituent groups. The group may be a terminal group or a bridging group.

The above discussion of alkyl and cycloalkyl substituents also applies to the alkyl portions of other substituents, such as without limitation, alkoxy, alkyl amines, alkyl ketones, arylalkyl, heteroarylalkyl, alkylsulfonyl and alkyl ester substituents and the like.

"Cycloalkylalkyl" means a cycloalkyl-alkyl-group in which the cycloalkyl and alkyl moieties are as previously described. Exemplary monocycloalkylalkyl groups include cyclopropylmethyl, cyclopentylmethyl, cyclohexylmethyl and cycloheptylmethyl. The group may be a terminal group or a bridging group.

"Halogen" represents chlorine, fluorine, bromine or iodine.

"Heterocycloalkyl" refers to a saturated or partially saturated monocyclic, bicyclic, or polycyclic ring containing at least one heteroatom selected from nitrogen, sulfur, oxygen, preferably from 1 to 3 heteroatoms in at least one ring. Each ring is preferably from 3 to 10 membered, more preferably 4 to 7 membered. Examples of suitable heterocycloalkyl substituents include pyrrolidyl, tetrahydrofuryl, tetrahydrothiofuranyl, piperidyl, piperazyl, tetrahydropyranyl, morphilino, 1,3-diazapane, 1,4-diazapane, 1,4-oxazepane, and 1,4-oxathiapane. The group may be a terminal group or a bridging group.

"Heterocycloalkenyl" refers to a heterocycloalkyl as described above but containing at least one double bond. The group may be a terminal group or a bridging group.

"Heterocycloalkylalkyl" refers to a heterocycloalkyl-alkyl group in which the heterocycloalkyl and alkyl moieties are as previously described. Exemplary heterocycloalkylalkyl groups include (2-tetrahydrofuryl)methyl, (2-tetrahydrothiofuranyl)methyl. The group may be a terminal group or a bridging group.

"Heteroalkyl" refers to a straight- or branched-chain alkyl group preferably having from 2 to 14 carbons, more preferably 2 to 10 carbons in the chain, one or more of which has been replaced by a heteroatom selected from S, O, P and N. Exemplary heteroalkyls include alkyl ethers, secondary and tertiary alkyl amines, amides, alkyl sulfides, and the like. The group may be a terminal group or a bridging group. As used herein reference to the normal chain when used in the context of a bridging group refers to the direct chain of atoms linking the two terminal positions of the bridging group.

"Aryl" as a group or part of a group denotes (i) an optionally substituted monocyclic, or fused polycyclic, aromatic carbocycle (ring structure having ring atoms that are all carbon) preferably having from 5 to 12 atoms per ring. Examples of aryl groups include phenyl, naphthyl, and the like; (ii) an optionally substituted partially saturated bicyclic aromatic carbocyclic moiety in which a phenyl and a $C_{5-7}$ cycloalkyl or $C_{5-7}$ cycloalkenyl group are fused together to form a cyclic structure, such as tetrahydronaphthyl, indenyl or indanyl. The group may be a terminal group or a bridging group.

"Arylalkenyl" means an aryl-alkenyl-group in which the aryl and alkenyl are as previously described. Exemplary arylalkenyl groups include phenylallyl. The group may be a terminal group or a bridging group.

"Arylalkyl" means an aryl-alkyl-group in which the aryl and alkyl moieties are as previously described. Preferred arylalkyl groups contain a $C_{1-5}$ alkyl moiety. Exemplary arylalkyl groups include benzyl, phenethyl and naphthelenemethyl. The group may be a terminal group or a bridging group.

"Heteroaryl" either alone or part of a group refers to groups containing an aromatic ring (preferably a 5 or 6 membered aromatic ring) having one or more heteroatoms as ring atoms in the aromatic ring with the remainder of the ring atoms being carbon atoms. Suitable heteroatoms include nitrogen, oxygen and sulphur. Examples of heteroaryl include thiophene, benzothiophene, benzofuran, benzimidazole, benzoxazole, benzothiazole, benzisothiazole, naphtho[2,3-b]thiophene, furan, isoindolizine, xantholene, phenoxatine, pyrrole, imidazole, pyrazole, pyridine, pyrazine, pyrimidine, pyridazine, indole, isoindole, 1H-indazole, purine, quinoline, isoquinoline, phthalazine, naphthyridine, quinoxaline, cinnoline, carbazole, phenanthridine, acridine, phenazine, thiazole, isothiazole, phenothiazine, oxazole, isooxazole, furazane, phenoxazine, 2-, 3- or 4-pyridyl, 2-, 3-, 4-, 5-, or 8-quinolyl, 1-, 3-, 4-, or 5-isoquinolinyl 1-, 2-, or 3-indolyl, and 2-, or 3-thienyl. The group may be a terminal group or a bridging group.

"Heteroarylalkyl" means a heteroaryl-alkyl group in which the heteroaryl and alkyl moieties are as previously described. Preferred heteroarylalkyl groups contain a lower alkyl moiety. Exemplary heteroarylalkyl groups include pyridylmethyl. The group may be a terminal group or a bridging group.

"Lower alkyl" as a group means unless otherwise specified, an aliphatic hydrocarbon group which may be straight or branched having 1 to 6 carbon atoms in the chain, more preferably 1 to 4 carbons such as methyl, ethyl, propyl (n-propyl or isopropyl) or butyl (n-butyl, isobutyl or tertiary-butyl). The group may be a terminal group or a bridging group.

It is understood that included in the family of compounds of Formula (I) are isomeric forms including diastereoisomers, enantiomers, tautomers, and geometrical isomers in "E" or "Z" configurational isomer or a mixture of E and Z isomers. It is also understood that some isomeric forms such as diastereomers, enantiomers, and geometrical isomers can be separated by physical and/or chemical methods and by those skilled in the art.

Some of the compounds of the disclosed embodiments may exist as single stereoisomers, racemates, and/or mixtures of enantiomers and/or diastereomers. All such single stereoisomers, racemates and mixtures thereof, are intended to be within the scope of the subject matter described and claimed.

Additionally, Formula (I) is intended to cover, where applicable, solvated as well as unsolvated forms of the compounds. Thus, each formula includes compounds having the indicated structure, including the hydrated as well as the non-hydrated forms.

In addition to compounds of the Formula (I), the compounds of the various embodiments include pharmaceutically acceptable salts, prodrugs, N-oxides and active metabolites of such compounds, and pharmaceutically acceptable salts of such metabolites.

The term "pharmaceutically acceptable salts" refers to salts that retain the desired biological activity of the above-identified compounds, and include pharmaceutically acceptable acid addition salts and base addition salts. Suitable pharmaceutically acceptable acid addition salts of compounds of Formula (I) may be prepared from an inorganic acid or from an organic acid. Examples of such inorganic acids are hydrochloric, sulfuric, and phosphoric acid. Appropriate organic acids may be selected from aliphatic, cycloaliphatic, aromatic, heterocyclic carboxylic and sulfonic classes of organic acids, examples of which are formic, acetic, propionic, succinic, glycolic, gluconic, lactic, malic, tartaric, citric, fumaric, maleic, alkyl sulfonic, arylsulfonic. Suitable pharmaceutically acceptable base addition salts of compounds of Formula (I) include metallic salts made from lithium, sodium, potassium, magnesium, calcium, aluminium, and zinc, and organic salts made from organic bases such as choline, diethanolamine, morpholine. Other examples of organic salts are: ammonium salts, quaternary salts such as tetramethylammonium salt; amino acid addition salts such as salts with glycine and arginine. Additional information on pharmaceutically acceptable salts can be found in Remington's Pharmaceutical Sciences, 19th Edition, Mack Publishing Co., Easton, Pa. 1995. In the case of agents that are solids, it is understood by those skilled in the art that the inventive compounds, agents and salts may exist in different crystalline or polymorphic forms, all of which are intended to be within the scope of the present invention and specified formulae.

"Prodrug" means a compound which is convertible in vivo by metabolic means (e.g. by hydrolysis, reduction or oxidation) to a compound of formula (I). For example an ester prodrug of a compound of formula (I) containing a hydroxyl group may be convertible by hydrolysis in vivo to the parent molecule. Suitable esters of compounds of formula (I) containing a hydroxyl group, are for example acetates, citrates, lactates, tartrates, malonates, oxalates, salicylates, propionates, succinates, fumarates, maleates, methylene-bis-β-hydroxynaphthoates, gestisates, isethionates, di-p-toluoyltartrates, methanesulphonates, ethanesulphonates, benzenesulphonates, p-toluenesulphonates, cyclohexylsulphamates and quinates. As another example an ester prodrug of a compound of formula (I) containing a carboxy group may be convertible by hydrolysis in vivo to the parent molecule. (Examples of ester prodrugs are those described by F. J. Leinweber, Drug Metab. Res., 18:379, 1987).

The term "therapeutically effective amount" or "effective amount" is an amount sufficient to effect beneficial or desired clinical results. An effective amount can be administered in one or more administrations. An effective amount is typically sufficient to palliate, ameliorate, stabilize, reverse, slow or delay the progression of the disease state.

The term "normal chain" refers to the direct chain joining the two ends of a linking moiety. In reference to the present compounds an alkoxyalkyl group is a heteroalkyl group containing a heteroatom in the normal chain (in this case an oxygen atom). An amide group is also a heteroalkyl group but it does not contain an oxygen atom in the normal chain (it has a nitrogen atom in the normal chain).

The term "functional equivalent" is intended to include variants of the specific protein kinase species described herein. It will be understood that kinases may have isoforms, such that while the primary, secondary, tertiary or quaternary structure of a given kinase isoform is different to the protoypical kinase, the molecule maintains biological activity as a protein kinase. Isoforms may arise from normal allelic variation within a population and include mutations such as amino acid substitution, deletion, addition, truncation, or duplication. Also included within the term "functional equivalent" are variants generated at the level of transcription. Many kinases (including JAK2 and CDK2) have isoforms that arise from transcript variation. It is also known that FLT3 has an isoform that is the result of exon-skipping. Other functional equivalents include kinases having altered post-translational modification such as glycosylation.

Specific compounds of the invention include the following:

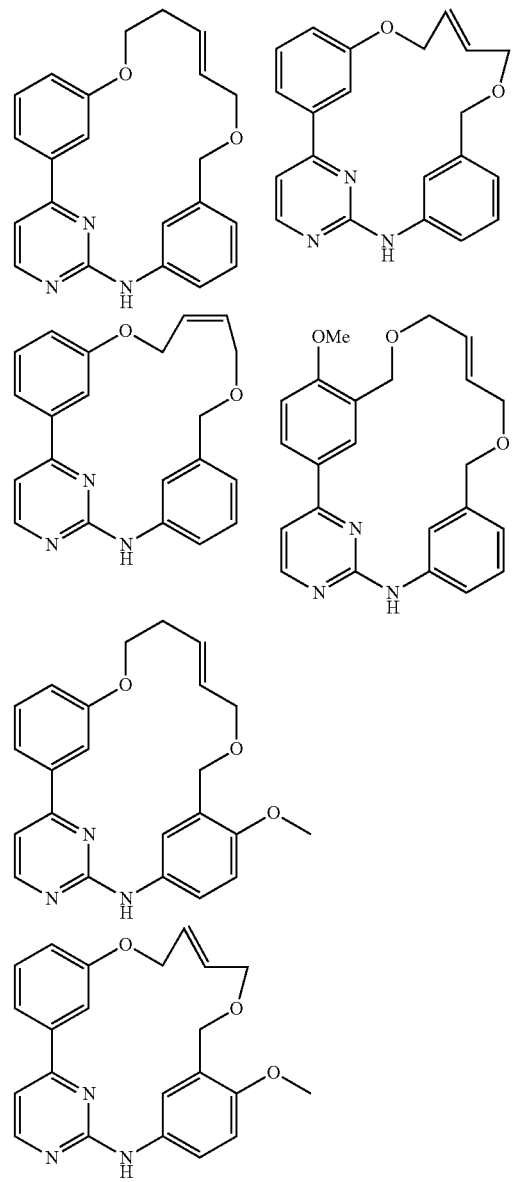

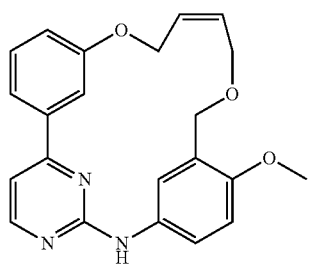
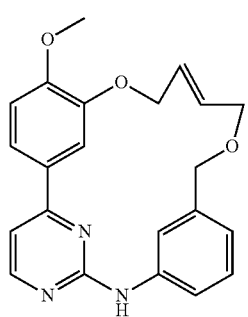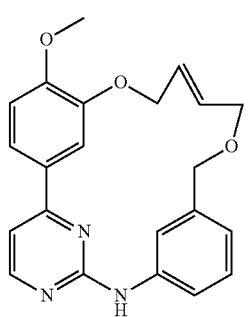
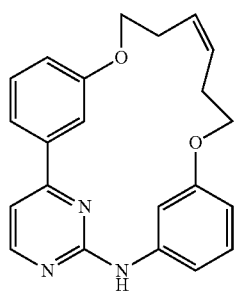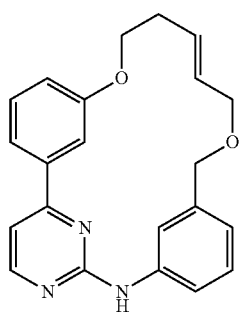
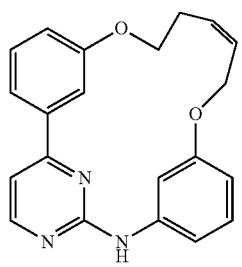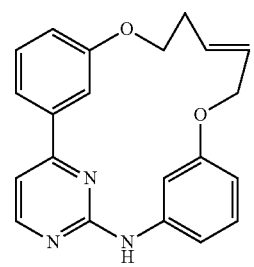
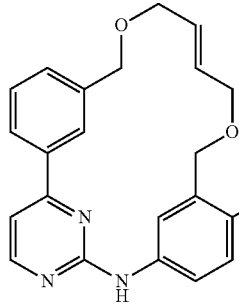
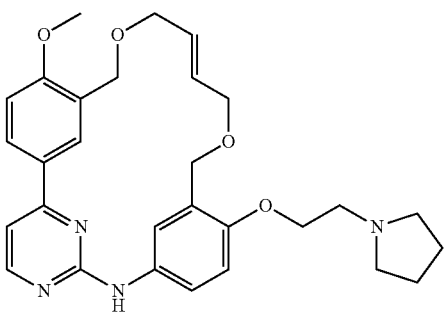
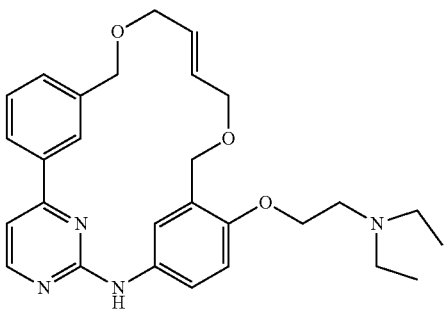
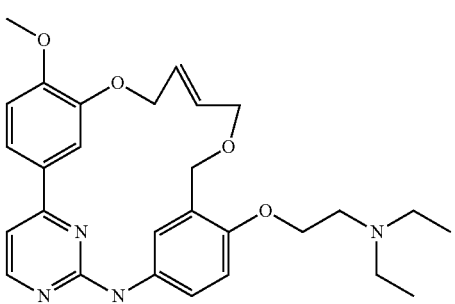
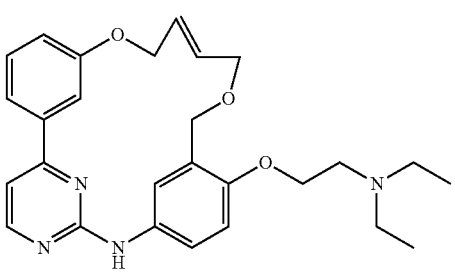
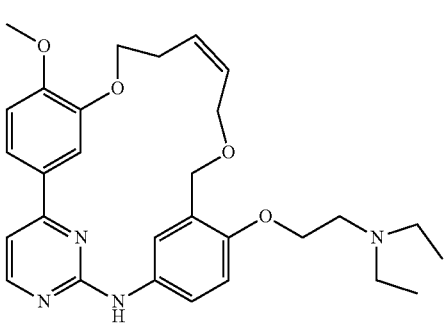

33
-continued
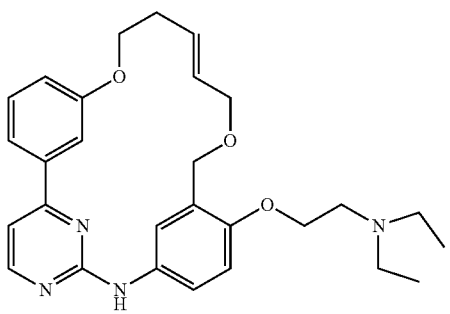
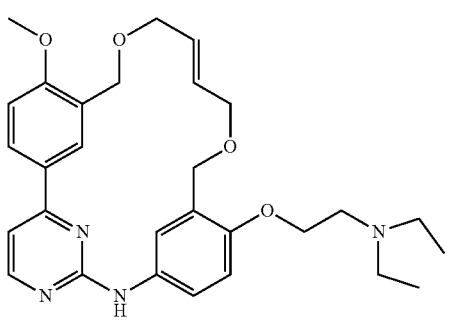
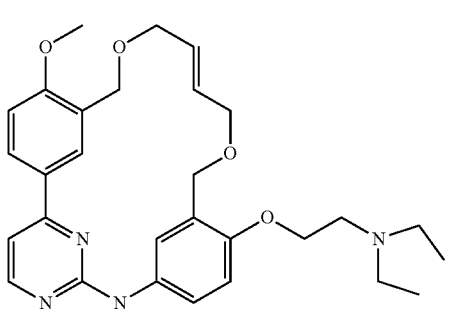
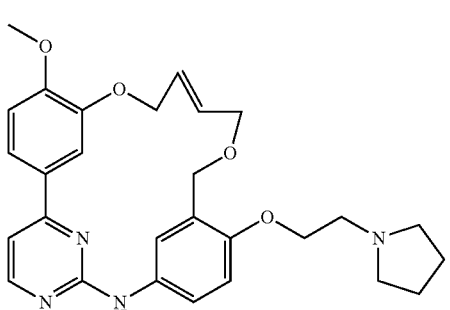
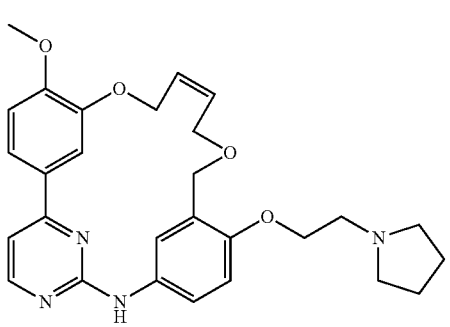
34
-continued
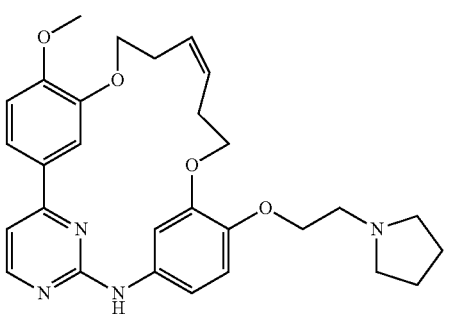
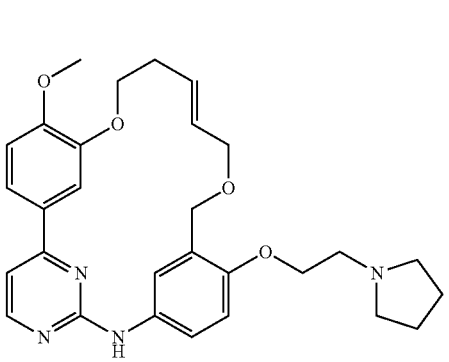
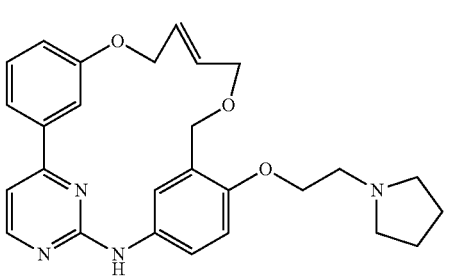
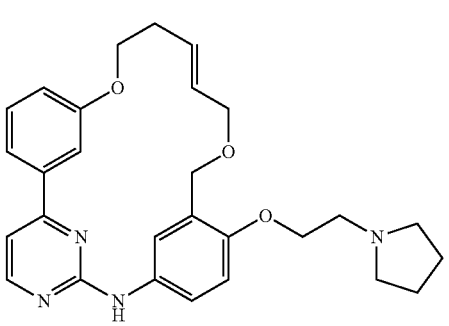
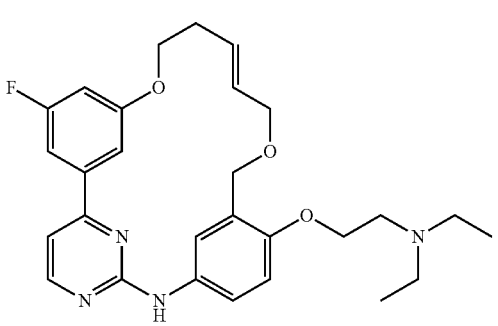

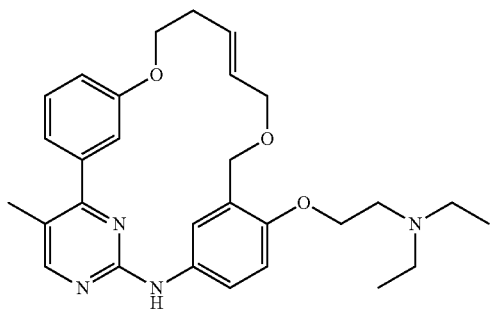
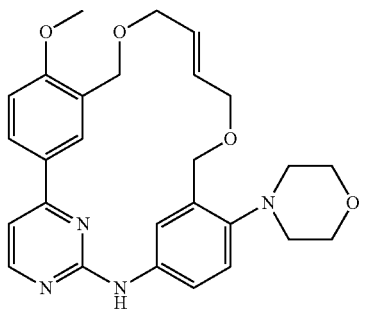
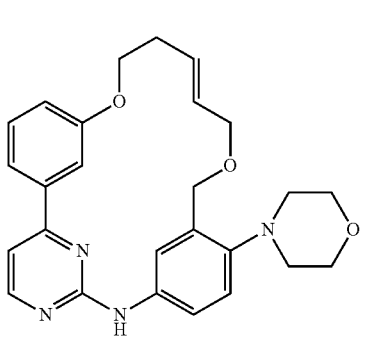
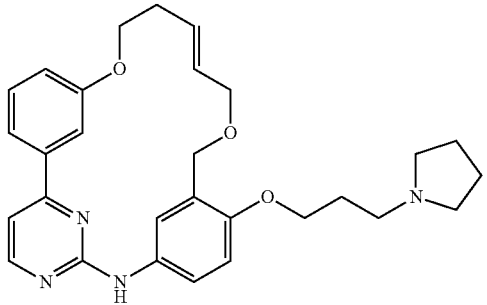
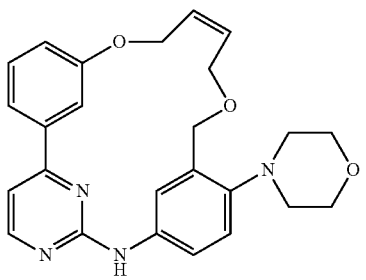
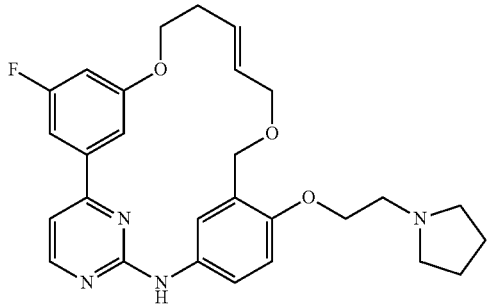
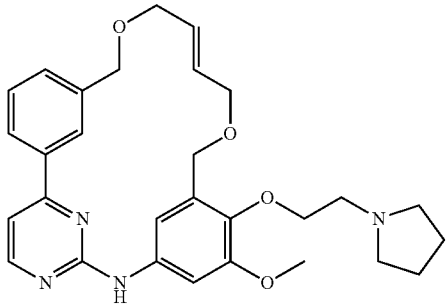
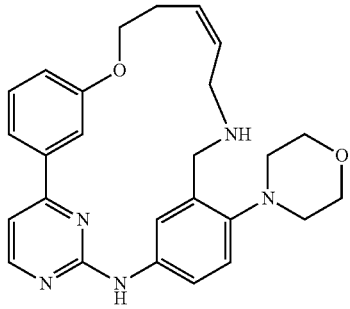
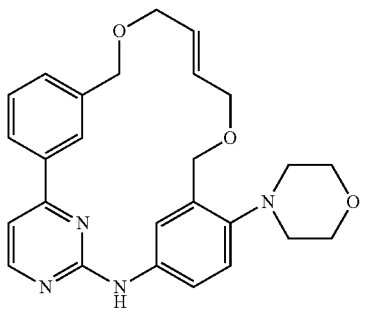
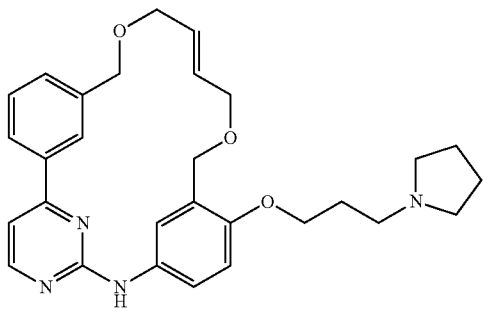

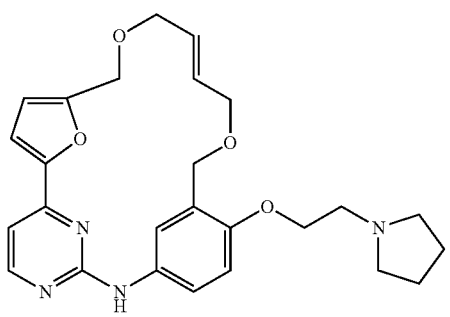
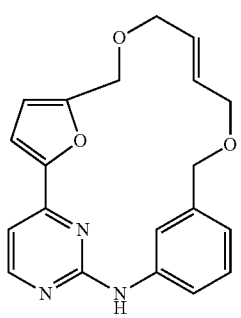
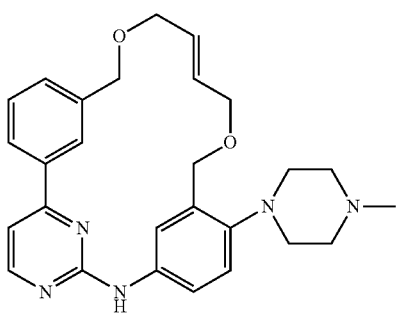
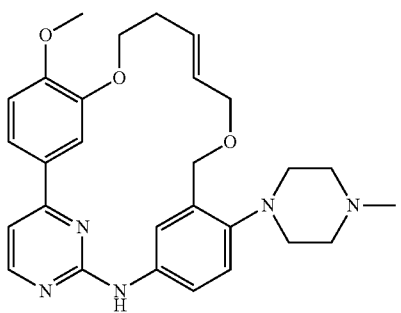
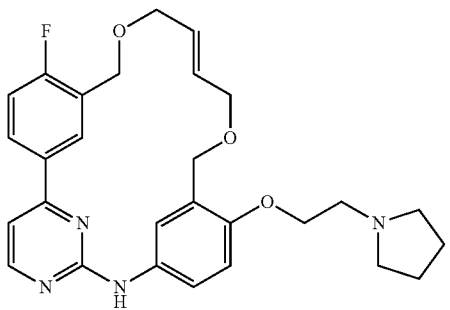
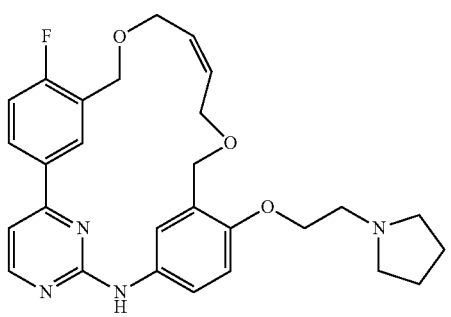
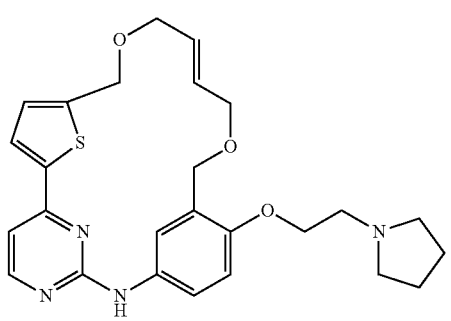
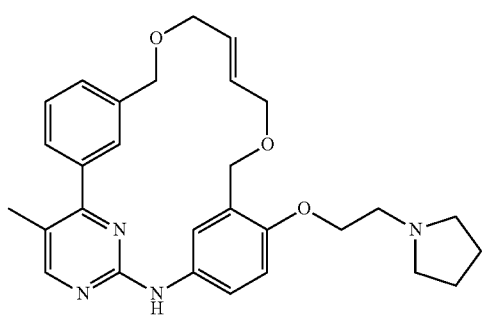
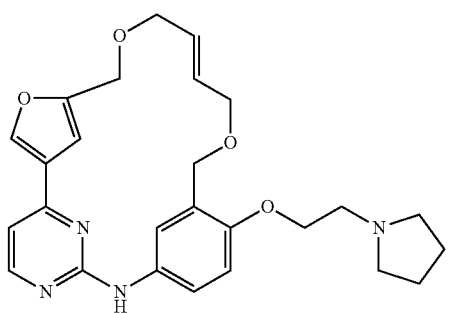
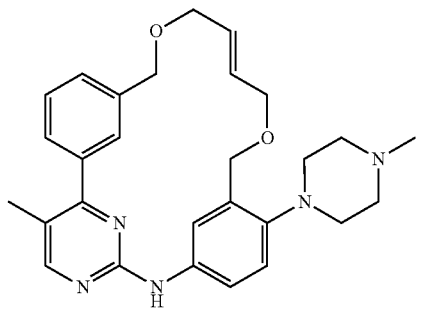

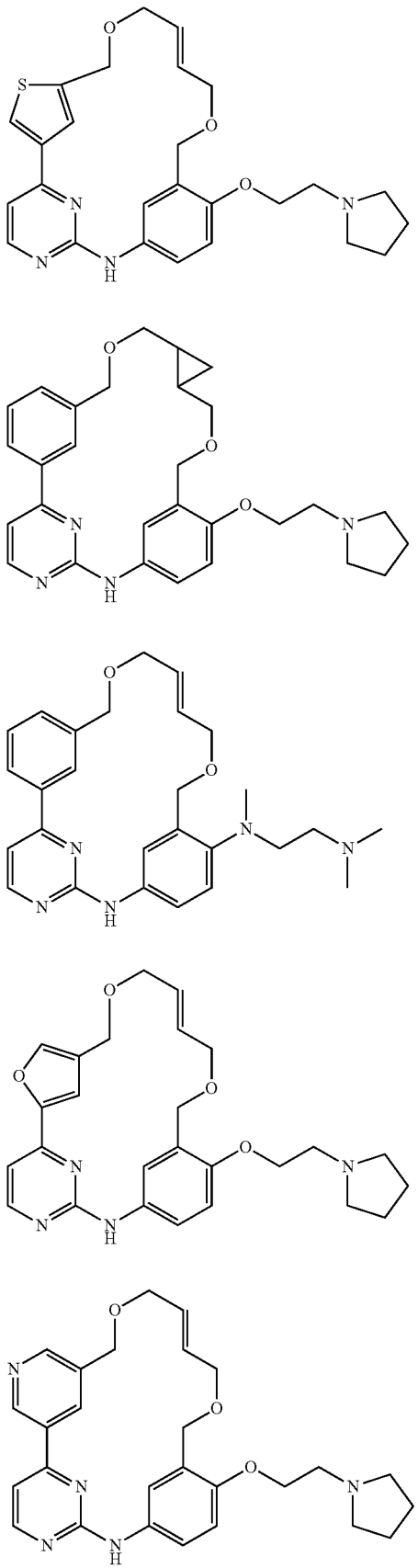
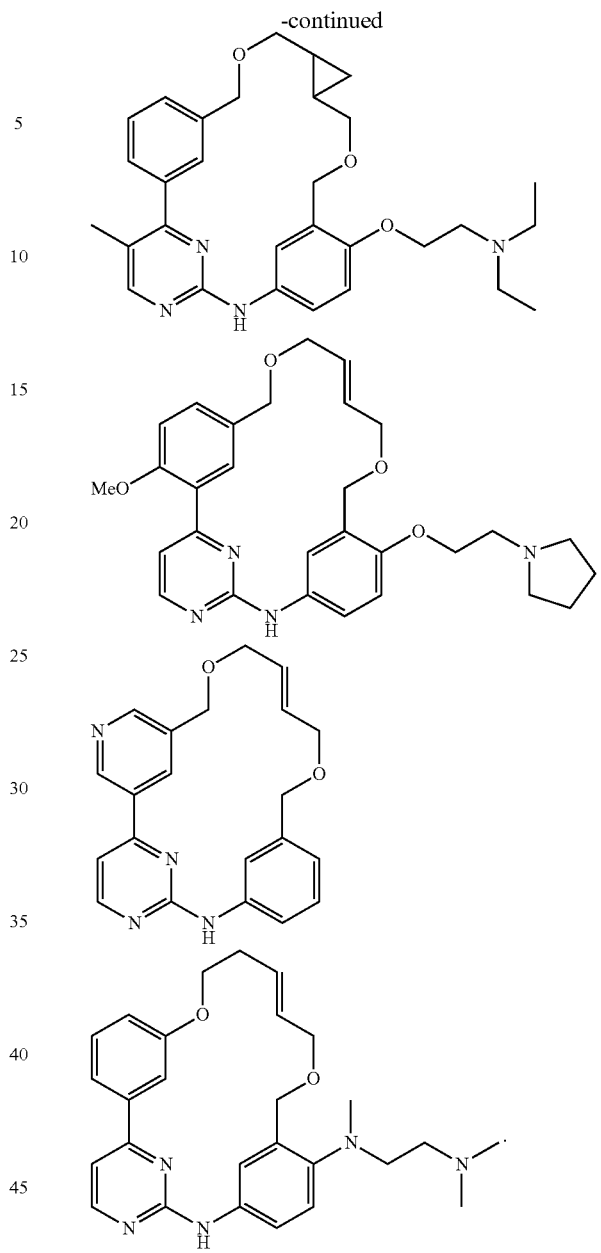

The compounds of the invention have the ability to inhibit the activity of certain protein kinases. The ability to inhibit kinase activity may be a result of the compounds of the invention acting directly and solely on the kinase molecule to inhibit biological activity. However, it is understood that the compounds may also act at least partially on co-factors of the kinase in question that are involved in the phosphorylation process. For example, where the kinase is cyclin-dependent, a co-factor such as cyclinA is involved in the transfer of phosphate from ATP (also considered a co-factor in itself) to the substrate molecule. Other kinase co-factors include ionic species (such as zinc and calcium), lipids (such as phosphatidylserine), and diacylglycerols.

The compounds may have activity against a wide range of protein kinases. One suitable family of protein kinases are the cyclin-dependent protein kinases. An example of the cyclin-dependent kinases is the Group I CMCG kinases. Examples of Group I CMCG kinases include CDC2Hs, CDK2, CDK3, CDK4, CDK5, CDK6, CDK9, PCTAIRE1, PCTAIRE2, PCTAIRE3, CAK/MO15, Dm2, Dm2c, Ddcdc2, DdPRK, LmmCRK1, PfC2R, EhC2R, CfCdc2R, cdc2+, CDC28, PHO85, KIN28, FpCdc2, MsCdc2B, and OsC2R. A Group I CMCG kinase of particular interest is CDK2.

Another family of protein kinases are protein tyrosine kinases. An example of protein tyrosine kinases is a Group VII protein tyrosine kinase. Examples of Group VII protein tyrosine kinase include TYK2, JAK1, JAK2 and HOP. A protein kinase of particular interest is the Group VII protein tyrosine kinase is JAK2. The JAK2 protein kinase may include a recurrent unique acquired clonal mutation. As stated previously this mutation is observed in a majority of polycythemia vera (PV) patients and a significant proportion of patients with other myeloproliferative disorders, including, essential thrombocythemia (ET) and chronic idiopathic myelofibrosis (IMF). A typical mutation is a valine to phenylalanine substitution at position 617 (V617F). The incidence of this mutation in PV patients is very high (around 78% of patients).

Another example of protein tyrosine kinases is the Group XIV protein tyrosine kinases. Examples of the Group XIV protein tyrosine kinase include PDGFR-b, PDGFR-a, CSF1R, c-kit, Flk2, FLT1, FLT2, FLT3 and FLT4. A Group XIV protein tyrosine kinase of particular interest is FLT3. The FLT3 kinase may include a mutation. There is substantial experimental and clinical evidence to support the hypothesis that FLT3 mutations are important in the initiation or maintenance of AML in some patients. Activating mutations of FLT3 result in constitutive activation of FLT3 tyrosine kinase activity and can transform factor-dependent hematopoietic cells as evidenced by conversion to factor-independent growth and formation of tumours in immunodeficient mice. In addition, retroviral transduction of primary murine bone marrow with an AML patient-derived FLT3 ITD (internal tandem duplication) cDNA results in a lethal myeloproliferative syndrome. Furthermore, retroviral transduction of bone marrow derived from promyelocytic leukemia/retinoic acid receptor (PML-RAR) transgenic mice with FLT3 ITD results in a marked increase in the incidence of acute progranulocytic (APL)-like leukemia in such mice when compared with mice that received a transplant of mock-transduced bone marrow. Applicants have demonstrated that kinase inhibitors described herein are capable of inhibiting FLT3 including an ITD where there is a duplication of amino acids VDFREYEYDH at amino acid position 592-601. In an even more specific embodiment of the method the FLT3 includes an internal tandem duplication. In an even more specific embodiment the internal tandem duplication is a duplication of amino acids VDFREYEYDH at position 592-601.

The inhibition of the protein kinase may be carried out in any of a number of well known ways in the art. For example if inhibition of the protein kinase in vitro is desired an appropriate amount of the compound of the invention may be added to a solution containing the kinase. In circumstances where it is desired to inhibit the activity of the kinase in a mammal the inhibition of the kinase typically involves administering the compound to a mammal containing the kinase.

Accordingly the compounds of the invention may find a multiple number of applications in which their ability to inhibit protein kinases of the type mentioned above can be utilised. For example the compounds may be used to inhibit protein kinases. The compounds may also be used in treating or preventing a condition in a mammal in which inhibition of a protein kinase and/or co-factor thereof prevents, inhibits or ameliorates a pathology or a symptomology of the condition.

Examples of conditions that may be treated by inhibition of protein kinases include prostate cancer, retinoblastoma, malignant neoplasm of breast, malignant tumour of colon, endometrial hyperplasia, osteosarcoma, squamous cell carcinoma, non-small cell lung cancer, melanoma, liver cell carcinoma, malignant neoplasm of pancreas, myeloid leukemia, cervical carcinoma, fibroid tumour, adenocarcinoma of the colon, T-cell leukemia, glioma, glioblastoma, oligodendroglioma, lymphoma, ovarian cancer, restenosis, astrocytoma, bladder neoplasms, musculoskeletal neoplasms and Alzheimer's Disease.

Other conditions that may be treated by inhibition of protein kinases include conditions such as Myeloproliferative disorders (chronic idiopathic myelofibrosis, polycythemia vera, essential thrombocythemia, chronic myeloid leukemia), myeloid metaplasia, chronic myelomonocytic leukemia, acute lymphocytic leukemia, acute erythroblastic leukemia, Hodgkin's disease, B-cell lymphoma, acute T-cell leukemia, breast carcinoma, ovarian cancer, colon carcinoma, prostate cancer, melanoma, myelodysplastic syndromes, keloids, congestive heart failure, ischemia, thrombosis, cardiac hypertrophy, pulmonary hypertension, and retinal degeneration.

Other conditions that may be treated by inhibition of protein kinases include acute myeloid leukemia, acute promyelocytic leukemia, acute lymphocytic leukemia, myelodysplastic syndromes, leukocytosis, juvenile myelomonocytic leukemia, acute B-cell leukemia, chronic myeloid leukemia, acute T-cell leukemia, myeloproliferative disorders, and chronic myelomonocytic leukemia.

The compounds of the invention may also be used the preparation of a medicament for treating a condition in an animal in which inhibition of a protein kinase can prevent, inhibit or ameliorate the pathology or symptomology of the condition. The compounds of the invention may also be used in the preparation of a medicament for the treatment or prevention of a kinase-related disorder.

One example of a kinase-related disorder is a proliferative disorder. In a specific embodiment the proliferative disorder is elected from the group consisting of myeloproliferative disorders (chronic idiopathic myelofibrosis, polycythemia vera, essential thrombocythemia, chronic myeloid leukemia), myeloid metaplasia, chronic myelomonocytic leukemia, acute myeloid leukemia, juvenile myelomonocytic leukemia, acute promyelocytic leukemia, acute lymphocytic leukemia, acute erythroblastic leukemia, acute B-cell leukemia, leukocytosis, Hodgkin's disease, B-cell lymphoma, acute T-cell leukemia, breast carcinoma, ovarian cancer, colon carcinoma, prostate cancer, melanoma, myelodysplastic syndromes, keloids, retinoblastoma, malignant neoplasm of breast, malignant tumour of colon, endometrial hyperplasia, osteosarcoma, squamous cell carcinoma, non-small cell lung cancer, melanoma, liver cell carcinoma, malignant neoplasm of pancreas, myeloid leukemia, cervical carcinoma, fibroid tumour, adenocarcinoma of the colon, glioma, glioblastoma, oligodendroglioma, lymphoma, ovarian cancer, restenosis, astrocytoma, bladder neoplasms, and musculoskeletal neoplasms.

One example of a proliferative disorder is cancer. The cancer may be a solid tumour. The solid tumour may be a tumour present in or metastasized from an organ or tissue selected from the group consisting of breast, ovary, colon, prostate, endometrium, bone, skin, lung, liver, pancreas, cervix, brain, neural tissue, lymphatic tissue, blood vessel, bladder and muscle.

Another example of a cancer is a hematological cancer. Examples of hematological cancers include acute myeloid leukemia, acute promyelocytic leukemia, acute lymphocytic leukemia, myelodysplastic syndrome, leukocytosis, juvenile myelomonocytic leukemia, acute B-cell leukemia, chronic myeloid leukemia, acute T-cell leukemia, chronic myelomonocytic leukemia, myeloid metaplasia, chronic myelomonocytic leukemia, acute erythroblastic leukemia, Hodgkin's disease, and B-cell lymphoma.

Another kinase-related disorder is a cardiovascular disorder. Examples of cardiovascular disorder include congestive heart failure, ischemia, thrombosis, cardiac hypertrophy and restenosis.

Another kinase-related disorder is a neurodegenerative disorder. The neurodegenerative disorder may be Alzheimer's disease.

The compounds disclosed have the ability to be used in the treatment of proliferative disorders. An example of such a disorder is cancer.

Administration of compounds within Formula (I) to humans can be by any of the accepted modes for enteral administration such as oral or rectal, or by parenteral administration such as subcutaneous, intramuscular, intravenous and intradermal routes. Injection can be bolus or via constant or intermittent infusion. The active compound is typically included in a pharmaceutically acceptable carrier or diluent and in an amount sufficient to deliver to the patient a therapeutically effective dose. In various embodiments the inhibitor compound may be selectively toxic or more toxic to rapidly proliferating cells, e.g. cancerous tumours, than to normal cells.

As used herein the term 'cancer' is a general term intended to encompass the vast number of conditions that are characterised by uncontrolled abnormal growth of cells.

It is anticipated that the compounds of the invention will be useful in treating various cancers including but not limited to bone cancers including Ewing's sarcoma, osteosarcoma, chondrosarcoma and the like, brain and CNS tumours including acoustic neuroma, neuroblastomas, glioma and other brain tumours, spinal cord tumours, breast cancers, colorectal cancers, advanced colorectal adenocarcinomas, endocrine cancers including adrenocortical carcinoma, pancreatic cancer, pituitary cancer, thyroid cancer, parathyroid cancer, thymus cancer, multiple endocrine neoplasma, gastrointestinal cancers including stomach cancer, oesophageal cancer, small intestine cancer, Liver cancer, extra hepatic bile duct cancer, gastrointestinal carcinoid tumour, gall bladder cancer, genitourinary cancers including testicular cancer, penile cancer, prostrate cancer, gynaecological cancers including cervical cancer, ovarian cancer, vaginal cancer, uterus/endometrium cancer, vulva cancer, gestational trophoblastic cancer, fallopian tube cancer, uterine sarcoma, head and neck cancers including oral cavity cancer, lip cancer, salivary gland cancer, larynx cancer, hypopharynx cancer, orthopharynx cancer, nasal cancer, paranasal cancer, nasopharynx cancer, leukemias including childhood leukemia, acute lymphocytic leukemia, acute myeloid leukemia, chronic lymphocytic leukemia, chronic myeloid leukemia, hairy cell leukemia, acute promyelocytic leukemia, plasma cell leukemia, myelomas, hematological disorders including myelodysplastic syndromes, myeloproliferative disorders, aplastic anaemia, Fanconi anaemia, Waldenstroms Macroglobulinemia, lung cancers including small cell lung cancer, non-small cell lung cancer, lymphomas including Hodgkin's disease, non-Hodgkin's lymphoma, cutaneous T-cell lymphoma, peripheral T-cell lymphoma, B-cell lymphoma, Burkitt's lymphoma, AIDS related Lymphoma, eye cancers including retinoblastoma, intraocular melanoma, skin cancers including melanoma, non-melanoma skin cancer, merkel cell cancer, soft tissue sarcomas such as childhood soft tissue sarcoma, adult soft tissue sarcoma, Kaposi's sarcoma, urinary system cancers including kidney cancer, Wilms tumour, bladder cancer, urethral cancer, and transitional cell cancer. Exemplary cancers that may be treated by compounds of this invention include Hematologic cancer such as myeloproliferative disorders (idiopathic myelofibrosis, polycythemia vera, essential thrombocythemia, chronic myeloid leukemia), myeloid metaplasia, chronic myelomonocytic leukemia, acute lymphocytic leukemia, acute erythroblastic leukemia, Hodgkin's and Non Hodgkin's disease, B-cell lymphoma, acute T-cell leukemia, myelodysplastic syndromes, plasma cell disorder, hairy cell leukemia, kaposi's sarcoma, lymphoma; gynaecologic cancer such as breast carcinoma, ovarian cancer, cervical cancer, vaginal and vulva cancer, endometrial hyperplasia; gastrointestinal tract cancer such as colorectal carcinoma, polyps, liver cancer, gastric cancer, pancreatic cancer, gall bladder cancer; urinary tract cancer such as prostate cancer, kidney and renal cancer; urinary bladder cancer, urethral cancer, penile cancer; skin cancer such as melanoma; brain tumour such as glioblastoma, neuroblastoma, astrocytoma, ependymoma, brain-stem gliomas, medulloblastoma, menigiomas, astrocytoma, oligodendroglioma; head and neck cancer such as nasopharyngeal carcinoma, laryngeal carcinoma; respiratory tract cancer such as lung carcinoma (NSCLC and SCLC), mesothelioma; eye disease such as retinoblastoma; musculo-skeleton diseases such as osteosarcoma, musculoskeleletal neoplasm; Squamous cell carcinoma and fibroid tumour.

Exemplary cancers that may be treated by compounds of this invention include but are not limited to bladder cancer, breast cancer, cervical cancer, colorectal cancer, colon cancer, gastric cancer, neuroblastoma, retinoblastoma, ovarian cancer, pancreatic cancer, leukemia, lymphoma, prostate cancer and lung cancer.

Exemplary cancers that may be treated by compounds of this invention are colon cancer, colorectal cancer, pancreatic cancer and cervical cancer.

Even further exemplary cancers that may be treated by compounds of the present inventions include but are not limited to B-cell lymphoma (e.g. Burkitt's lymphoma), leukemia (e.g. acute promyelocytic leukemia, erythroleukemia), cutaneous T-cell lymphoma (CTCL) and peripheral T-cell lymphoma.

Even further exemplary cancers that may be treated by compounds of the present invention include solid tumours and hematologic malignancies.

It is anticipated that, by virtue of their JAK2 inhibition, the compounds of the invention will also be useful in treating various myeloproliferative disorders which may include polycythemia vera, essential thrombocythemia and idiopathic myelofibrosis.

In using the compounds of the invention they can be administered in any form or mode which makes the compound bioavailable. One skilled in the art of preparing formulations can readily select the proper form and mode of administration depending upon the particular characteristics of the compound selected, the condition to be treated, the stage of the condition to be treated and other relevant circumstances. We refer the reader to Remingtons Pharmaceutical Sciences, 19$^{th}$ edition, Mack Publishing Co. (1995) for further information.

The compounds of the present invention can be administered alone or in the form of a pharmaceutical composition in combination with a pharmaceutically acceptable carrier, diluent or excipient. The compounds of the invention, while effective themselves, are typically formulated and administered in the form of their pharmaceutically acceptable salts as these forms are typically more stable, more easily crystallised and have increased solubility.

The compounds are, however, typically used in the form of pharmaceutical compositions which are formulated depending on the desired mode of administration. As such in a further embodiment the present invention provides a pharmaceutical composition including a compound of Formula (I) and a pharmaceutically acceptable carrier, diluent or excipient. The compositions are prepared in manners well known in the art.

The invention in other embodiments provides a pharmaceutical pack or kit comprising one or more containers filled with one or more of the ingredients of the pharmaceutical compositions of the invention. In such a pack or kit can be found a container having a unit dosage of the agent (s). The kits can include a composition comprising an effective agent either as concentrates (including lyophilized compositions), which can be diluted further prior to use or they can be provided at the concentration of use, where the vials may include one or more dosages. Conveniently, in the kits, single dosages can be provided in sterile vials so that the physician can employ the vials directly, where the vials will have the desired amount and concentration of agent(s). Associated with such container(s) can be various written materials such as instructions for use, or a notice in the form prescribed by a governmental agency regulating the manufacture, use or sale of pharmaceuticals or biological products, which notice reflects approval by the agency of manufacture, use or sale for human administration.

The compounds of the invention may be used or administered in combination with one or more additional drug (s) that are anti-cancer drugs and/or procedures (e.g. surgery, radiotherapy) for the treatment of the disorder/diseases mentioned. The components can be administered in the same formulation or in separate formulations. If administered in separate formulations the compounds of the invention may be administered sequentially or simultaneously with the other drug(s).

In addition to being able to be administered in combination with one or more additional drugs that include anti-cancer drugs, the compounds of the invention may be used in a combination therapy. When this is done the compounds are typically administered in combination with each other. Thus one or more of the compounds of the invention may be administered either simultaneously (as a combined preparation) or sequentially in order to achieve a desired effect. This is especially desirable where the therapeutic profile of each compound is different such that the combined effect of the two drugs provides an improved therapeutic result.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of micro-organisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents that delay absorption such as aluminium monostearate and gelatin.

If desired, and for more effective distribution, the compounds can be incorporated into slow release or targeted delivery systems such as polymer matrices, liposomes, and microspheres.

The injectable formulations can be sterilized, for example, by filtration through a bacterial-retaining filter, or by incorporating sterilizing agents in the form of sterile solid compositions that can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

If desired, and for more effective distribution, the compounds can be incorporated into slow release or targeted delivery systems such as polymer matrices, liposomes, and microspheres.

The active compounds can also be in microencapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminium metahydroxide, bentonite, agar-agar, and tragacanth, and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Dosage forms for topical administration of a compound of this invention include powders, patches, sprays, ointments and inhalants. The active compound is mixed under sterile conditions with a pharmaceutically acceptable carrier and any needed preservatives, buffers, or propellants which may be required.

The amount of compound administered will preferably treat and reduce or alleviate the condition. A therapeutically effective amount can be readily determined by an attending diagnostician by the use of conventional techniques and by observing results obtained under analogous circumstances. In determining the therapeutically effective amount a number of factors are to be considered including but not limited to, the species of animal, its size, age and general health, the specific condition involved, the severity of the condition, the response of the patient to treatment, the particular compound administered, the mode of administration, the bioavailability of the preparation administered, the dose regime selected, the use of other medications and other relevant circumstances.

A preferred dosage will be a range from about 0.01 to 300 mg per kilogram of body weight per day. A more preferred dosage will be in the range from 0.1 to 100 mg per kilogram of body weight per day, more preferably from 0.2 to 80 mg per kilogram of body weight per day, even more preferably 0.2 to 50 mg per kilogram of body weight per day. A suitable dose can be administered in multiple sub-doses per day.

As discussed above, the compounds of the embodiments may be useful for treating proliferative diseases. Examples of such cell proliferative diseases or conditions include cancer (include any metastases), psoriasis, and smooth muscle cell proliferative disorders such as restenosis. The inventive compounds may be particularly useful for treating tumours such as breast cancer, colon cancer, lung cancer, ovarian cancer, prostate cancer, head and/or neck cancer, or renal, gastric, pancreatic cancer and brain cancer as well as hematologic malignancies such as lymphoma and leukemia. In addition, the inventive compounds may be useful for treating a proliferative disease that is refractory to the treatment with other anti-cancer drugs; and for treating hyperproliferative conditions such as leukemias, psoriasis and restenosis. In other embodiments, compounds of this invention can be used to treat pre-cancer conditions or hyperplasia including familial adenomatous polyposis, colonic adenomatous polyps, myeloid dysplasia, endometrial dysplasia, endometrial hyperplasia with atypia, cervical dysplasia, vaginal intraepithelial neoplasia, benign prostatic hyperplasia, papillomas of the larynx, actinic and solar keratosis, seborrheic keratosis and keratoacanthoma.

Synthesis of Pyrimidine Macrocycles

As discussed above the invention provides a method of synthesis of a compound of formula (I) the method including the steps of:

(a) providing a compound of the formula

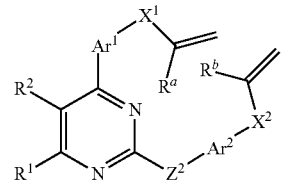

wherein $R^1$, $R^2$, $R^a$, $R^b$, $Z^2$, $Ar^1$, $Ar^2$, $X^1$ and $X^2$ are as defined above;

(b) subjecting the compound to ring closing metathesis;

(c) optionally reacting the double bond thus formed to form a cycloalkyl group.

The methods of the invention involve cyclisation of a diene compound of the formula described above which can be produced using procedures well known in the art or by the ones detailed below. The exact choice of method used to produce the diene for cyclisation will depend upon the diene selected and methods of synthesis of the dienes are within the skill of the skilled addressee. The compound may be reacted in its free form although it is typical that it is first converted to a suitable acid salt. Acid salts are well known as is discussed above with the hydrochloride salt and the trifluoroacetic acid salt being found to be particularly suitable.

Once the diene of an appropriate formula has been provided as discussed above it is then subjected to ring closing metathesis using standard conditions. A number of catalysts are well known to be suitable for ring closing metathesis including a number of ruthenium based catalysts. Suitable ruthenium based catalysts include well-known ruthenium based catalysts used in olefin metathesis reactions, such as Grubb's catalyst (first and second generation), Hoveyda's catalyst (first and second generation) and Nolan's catalyst. In each instance it may be necessary to make appropriate adjustments to the reaction conditions to allow ring-closing to occur. In one specific embodiment the catalyst is Grubb's second generation catalyst.

Ruthenium-based catalysts useful for the metathesis cyclisation step, as discussed above are all known catalysts that may be obtained by known synthetic techniques. For example, see the following references for examples of suitable ruthenium-based catalysts:

Organometallics 2002, 21, 671; 1999, 18, 5416; and 1998, 17, 2758;

J. Am. Chem. Soc. 2001, 123, 6543; 1999, 121, 791; 1999, 121, 2674; 2002, 124, 4954; 1998, 120, 2484; 1997, 119, 3887; 1996, 118, 100; and 1996, 118, 9606

J. Org. Chem. 1998, 63, 9904; and 1999, 64, 7202;

Angew. Chem. Int. Ed. Engl. 1998, 37, 2685; 1995, 34, 2038; 2000, 39, 3012 and 2002, 41, 4038;

U.S. Pat. Nos. 5,811,515; 6,306,987 B1; and 6,608,027 B1.

The ratio of diene to catalyst may vary widely as would be clear to a skilled addressee in the art. Nevertheless a suitable ratio is such that the ratio is from 100:1 to 1:1. A particularly suitable ratio is from 20:1 to 2:1. A more specific ratio is from 20:1 to 10:1.

The ring closing metathesis step may be carried out over a broad temperature range with the range of temperatures typically being chosen based upon the diene being cyclised, the time of reaction, and the catalyst chosen. In one embodiment the reaction is carried out at a temperature of from 20 to 200° C. In another embodiment the temperature is from 30 to 120° C. In another embodiment the temperature is in the range of from 30 to 50° C. In a specific embodiment the temperature is 40° C.

The ring-closing step may be carried out in the presence of any suitable non-interfering solvent that does not interfere with the reaction. A skilled addressee in the area can readily select suitable solvents that do not interfere with the reaction, nevertheless, examples of suitable solvents include alkanes, such as n-pentane, n-hexane or n-heptane, aromatic hydrocarbons, such as benzene, toluene or xylene, chlorinated hydrocarbons such as dichloromethane, trichloromethane, tetrachloromethane or dichloroethane, ether solvents, such as tetrahydrofuran, 2-methyl-tetrahydrofuran, 3-methyl-tetrahydrofuran, cyclopentyl methyl ether, methyl tert-butyl ether, dimethyl ether, diethyl ether or dioxane and methyl alcohol. An example of a specific solvent is dichloromethane.

The ring closing metathesis step may be carried out over a wide range of diene dilutions in the solvent with the ratio of diene to diluent typically being in the range of from 1:4000 by weight to 1:25 by weight. In another embodiment the ratio is from 1:200 by weight to 1:50 by weight.

The cycloalkylation step may be carried out using any cycloalkylation agent well known in the art. An example of a suitable cycloalkylation agent is a cyclopropanation agent. Examples of cyclopropanation agents are well known in the art and include diazomethane and carbenes. The use of these agents are well known and it is within the scope of a skilled addressee to be able to carry out reactions of this type.

The cycloalkylation reactions are typically carried out in a non-interfering solvent such as acetonitrile, ethyl acetate/hexane admixtures, ethyl acetate, tetrahydrofuran, ether, toluene, acetone, carbon tetrachloride, and dichloromethane or mixtures thereof. It will be appreciated by those skilled in the art that a range of solvents would in fact be suitable for use in conducting the reaction of the invention. In any specific case an optimum solvent can be identified by trial and experiment using the above solvents and others.

The agents of the various embodiments may be prepared using the reaction routes and synthesis schemes as described below, employing the techniques available in the art using starting materials that are readily available. The preparation of particular compounds of the embodiments is described in detail in the following examples, but the artisan will recognize that the chemical reactions described may be readily adapted to prepare a number of other agents of the various embodiments. For example, the synthesis of non-exemplified compounds may be successfully performed by modifications apparent to those skilled in the art, e.g. by appropriately protecting interfering groups, by changing to other suitable reagents known in the art, or by making routine modifications of reaction conditions. A list of suitable protecting groups in organic synthesis can be found in T. W. Greene's Protective Groups in Organic Synthesis, $3^{rd}$, John Wiley & Sons, 1991. Alternatively, other reactions disclosed herein or known in the art will be recognized as having applicability for preparing other compounds of the various embodiments.

Reagents useful for synthesizing compounds may be obtained or prepared according to techniques known in the art.

In the examples described below, unless otherwise indicated, all temperatures in the following description are in degrees Celsius and all parts and percentages are by weight, unless indicated otherwise.

Various starting materials and other reagents were purchased from commercial suppliers, such as Aldrich Chemical Company or Lancaster Synthesis Ltd., and used without further purification, unless otherwise indicated. Tetrahydrofuran (THF) and N,N-dimethylformamide (DMF) were purchased from Aldrich in SureSeal bottles and used as received. All solvents were purified by using standard methods in the art, unless otherwise indicated.

The reactions set forth below were performed under a positive pressure of nitrogen, argon or with a drying tube, at ambient temperature (unless otherwise stated), in anhydrous solvents, and the reaction flasks are fitted with rubber septa for the introduction of substrates and reagents via syringe. Glassware was oven-dried and/or heat-dried. Analytical thin-layer chromatography was performed on glass-backed silica gel 60 F 254 plates (E Merck (0.25 mm)) and eluted with the appropriate solvent ratios (v/v). The reactions were assayed by TLC and terminated as judged by the consumption of starting material.

The TLC plates were visualized by UV absorption or with a p-anisaldehyde spray reagent or a phosphomolybdic acid reagent (Aldrich Chemical, 20 wt % in ethanol) which was activated with heat, or by staining in an iodine chamber. Work-ups were typically done by doubling the reaction volume with the reaction solvent or extraction solvent and then washing with the indicated aqueous solutions using 25% by volume of the extraction volume (unless otherwise indicated). Product solutions were dried over anhydrous sodium sulfate prior to filtration, and evaporation of the solvents was under reduced pressure on a rotary evaporator and noted as solvents removed in vacuo. Flash column chromatography [Still et al, J. Org. Chem., 43, 2923 (1978)] was conducted using E Merck-grade flash silica gel (47-61 mm) and a silica gel:crude material ratio of about 20:1 to 50:1, unless otherwise stated. Hydrogenolysis was done at the pressure indicated or at ambient pressure.

$^1$H NMR spectra were recorded on a Bruker instrument operating at 400 MHz, and $^{13}$C-NMR spectra was recorded operating at 100 MHz. NMR spectra are obtained as $CDCl_3$ solutions (reported in ppm), using chloroform as the reference standard (7.27 ppm and 77.00 ppm) or $CD_3OD$ (3.4 and 4.8 ppm and 49.3 ppm), or an internal tetramethylsilane standard (0.00 ppm) when appropriate. Other NMR solvents were used as needed. When peak multiplicities are reported, the following abbreviations are used: s=singlet, d=doublet, t=triplet, m=multiplet, br=broadened, dd=doublet of doublets, dt=doublet of triplets. Coupling constants, when given, are reported in Hertz.

Mass spectra were obtained using LC/MS either in ESI or APCI. All melting points are uncorrected.

All final products had greater than 90% purity (by HPLC at wavelengths of 220 nm and 254 nm).

The following examples are intended to illustrate the embodiments disclosed and are not to be construed as being limitations thereto. Additional compounds, other than those described below, may be prepared using the following described reaction scheme or appropriate variations or modifications thereof.

General Synthetic Scheme

Scheme 1 is a general synthetic scheme outlining the procedures for the manufacture of compounds of the invention of general formula (VIIIa) and (IXa) being compounds of the invention wherein $X^1$ and $X^2$ are heteroalkyl groups containing at least one oxygen atom in the normal chain, and $Ar^1$ and $Ar^2$ are phenylene. This general procedure can be modified to produce other compounds of the invention with different values for $X^1$, $X^2$, $Ar^1$ and $Ar^2$ by appropriate modification of the reagents and starting materials used. A skilled addressee would readily be able to make these changes. The compounds of formula (VIIIa) may be reacted with appropriate reagents to produce the associated cyclopropyl analogs of formula (IXa).

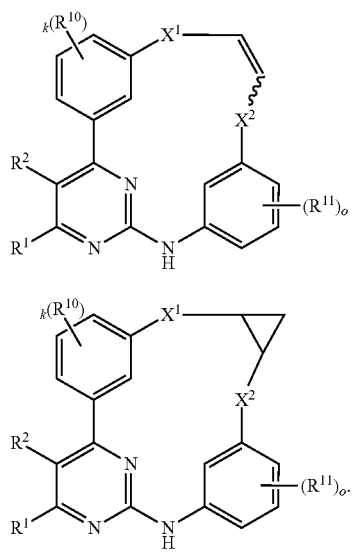

As can be seen in scheme 1 an appropriately substituted 2,4-dichloropyrimidine (Ia) is treated under Suzuki coupling conditions with a suitably functionalized boronic acids of type (IIa) to afford biaryl compounds of type (IIIa), which on treatment with allyl bromides (IV) in the presence of a base such as $Cs_2CO_3$ furnish allyl compounds of type (Va). Both the compound of formula (IIIa) and the compound of formula (IVa) are functionalized with appropriate L and $L^1$ groups respectively to produce the desired $X^1$ group after reaction. Variation of the identity of the groups L and $L^1$ easily allows for entry into the wide range of different $X^1$ groups contemplated by the present invention. Substitution with an appropriately functionalized aniline (VIa) under standard conditions affords terminal alkenes (VIIa), a key intermediate ready for ring closing metathesis (RCM). Once again selection of the appropriately substituted aniline (VIa) allows entry into a wide range of possible $X^2$ groups contemplated by the present invention. Employing Grubbs $2^{nd}$ generation catalyst RCM furnishes (VIIIa) as a mixture of trans- and cis-isomers which can be separated by chromatography. Compounds of type (IXa) may be obtained by cyclopropanation under standard conditions.

Scheme 1

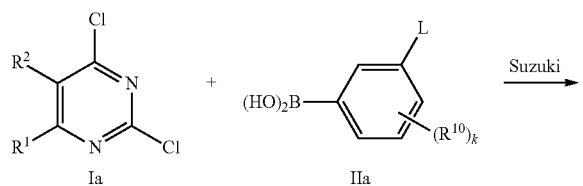

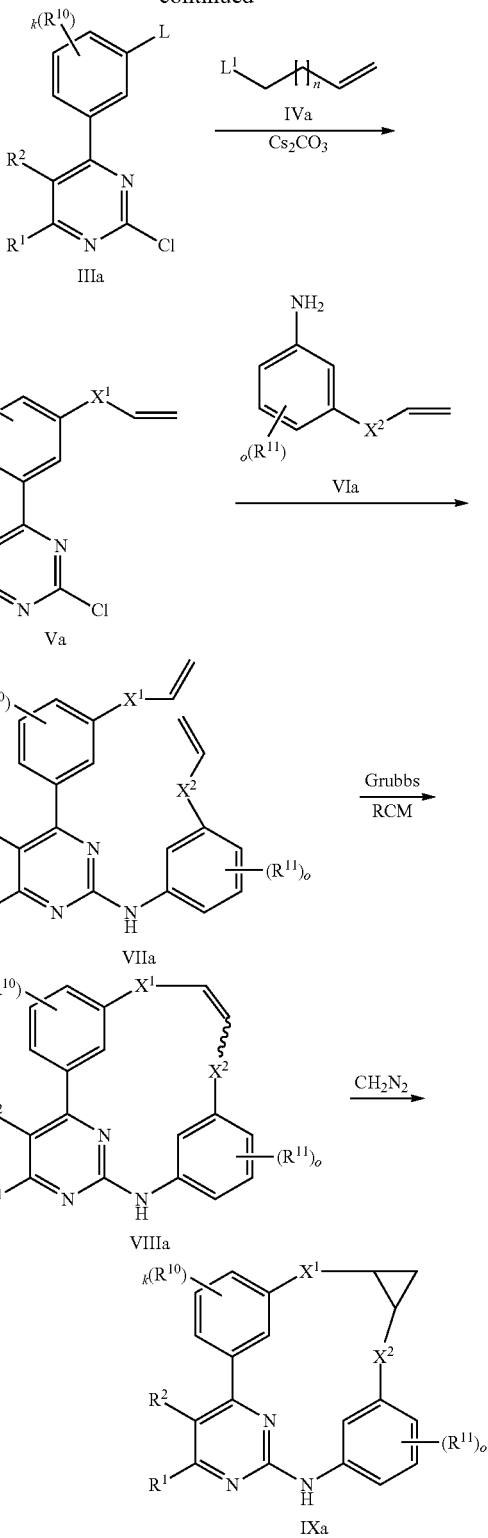

By varying the identities of the starting materials a number of different combinations of $X^1$ and $X^2$ can be envisaged and produced as can a number of differentially substituted forms of $Ar^1$ and $Ar^2$. In the scheme shown both $Ar^1$ and $Ar^2$ are represented as phenyl moieties, however other aryls can be accessed by employing analogous chemistry as depicted in Scheme 1. Synthetic procedures for the synthesis of a number of analogs of the compounds of formula VIIIa are detailed below.

Synthesis of XVIIIb and XVIIIc

Scheme 2 illustrates the procedure used for preparing compounds of formula (XVIIIb and XVIIIc) that can be prepared by analogous procedures, for example, by the choice of appropriate starting materials.

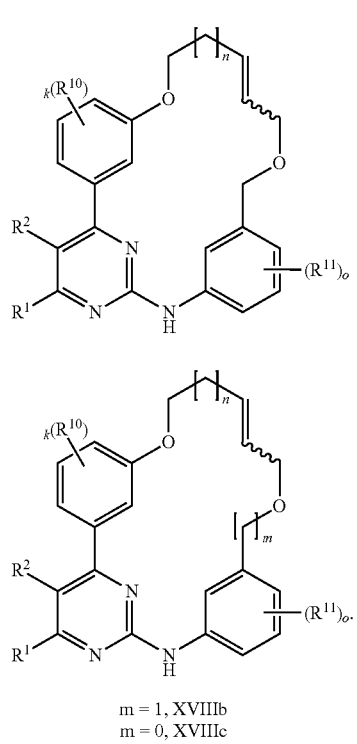

m = 1, XVIIIb
m = 0, XVIIIc

Once again coupling of commercially available 2,4-dichloropyrimidine (Ia) under Suzuki coupling conditions with boronic acids of type (XIIa) affords biaryl compounds of type (XIIIa), which on treatment with alkenyl bromides (XIV) in the presence of a base such as $Cs_2CO_3$ furnish unsaturated ethers of type (XVa). Substitution with aniline (XVIb or XVIc) under standard conditions affords terminal alkenes (XVIIb or XVIIc), a key intermediate ready for ring closing metathesis (RCM). Employing Grubbs $2^{nd}$ generation catalyst RCM furnishes (XVIIIb or XVIIIc). Compounds of type (XIXb) are obtained by cyclopropanation under standard conditions.

Scheme 2

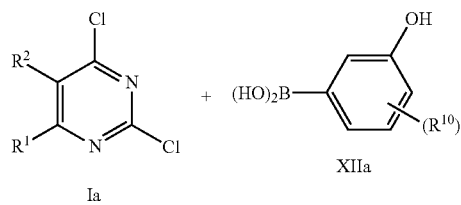

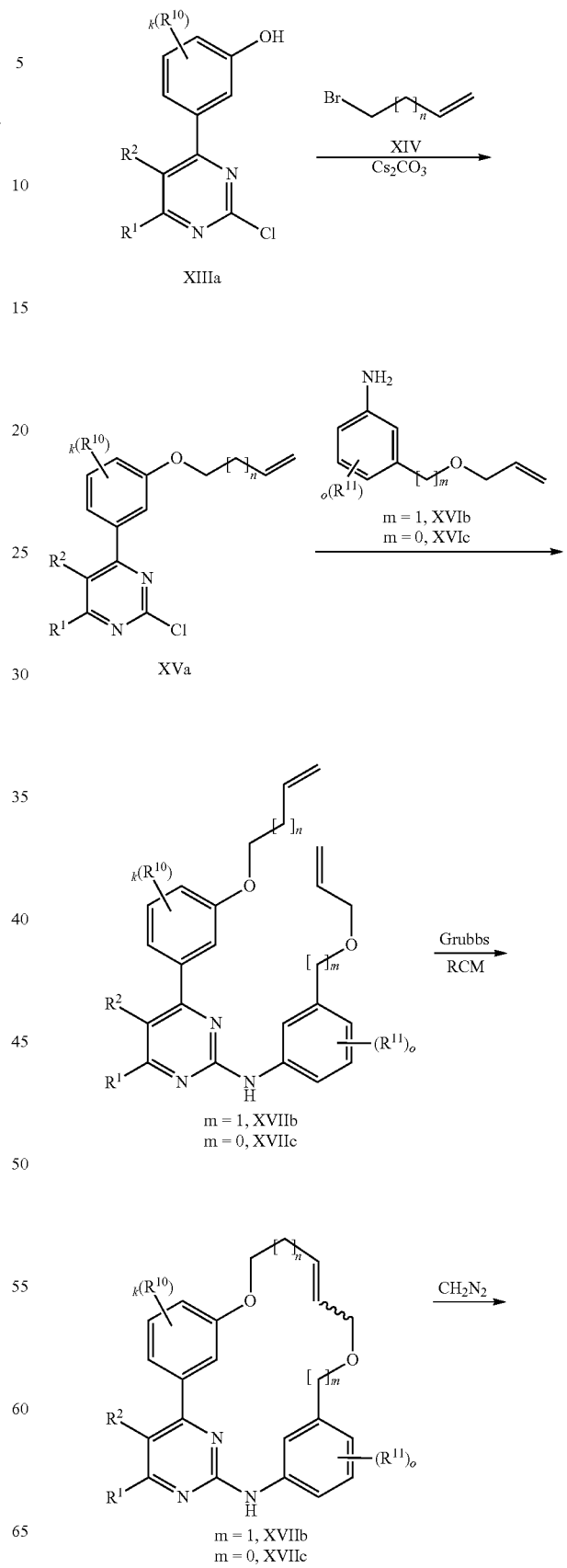

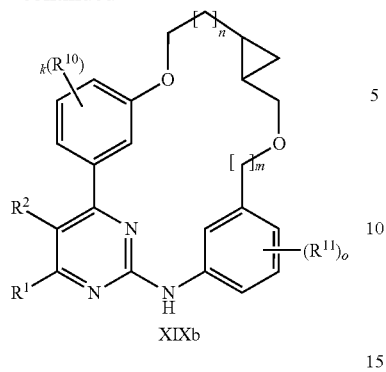

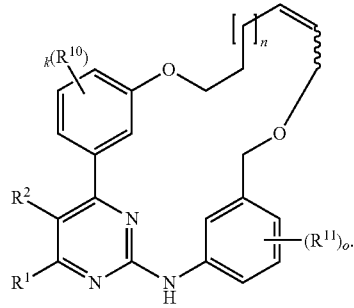

Synthesis of Intermediate XVIb

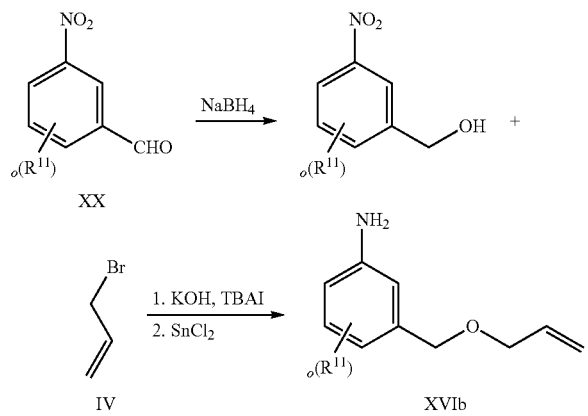

Aniline (XVIb) is obtained from nitro-aldehyde (XX) by alkylation of the corresponding alcohol (prepared by reduction of aldehyde (XX) with sodium borohydride) with allyl bromide (IVa1) followed by $SnCl_2$ reduction of the nitro function.

Synthesis of Intermediate XVIc

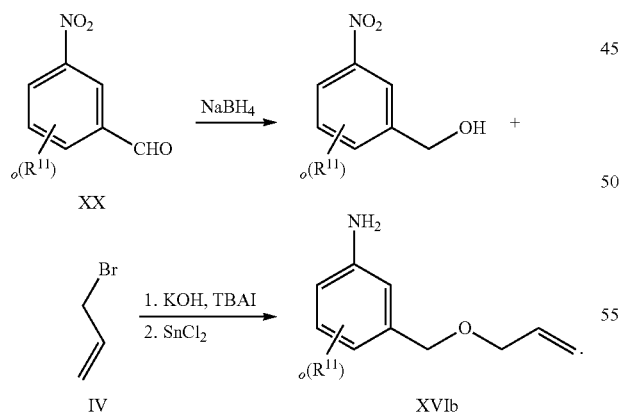

Aniline (XVIc) is obtained from a 3-nitrophenol by alkylation with allyl bromide Oval) followed by $SnCl_2$ reduction.

Synthesis of XVIIId

Scheme 3 illustrates the procedure used for preparing compounds of formula (XVIIId) that can be prepared by analogous procedures, for example, by the choice of appropriate starting materials.

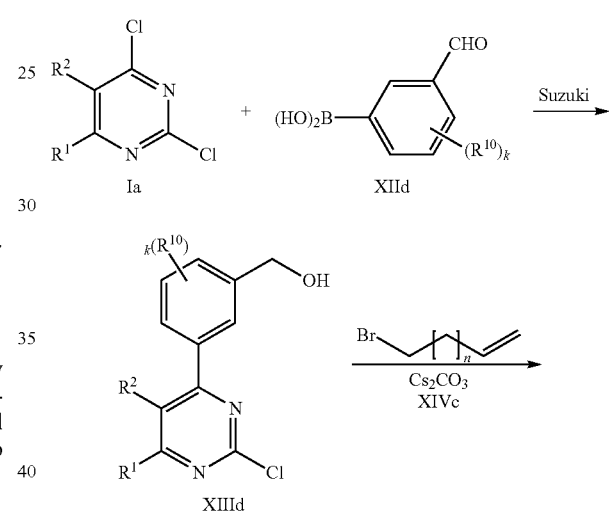

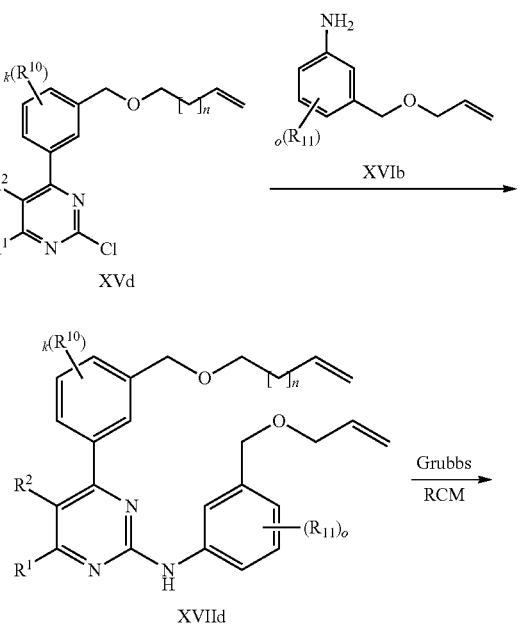

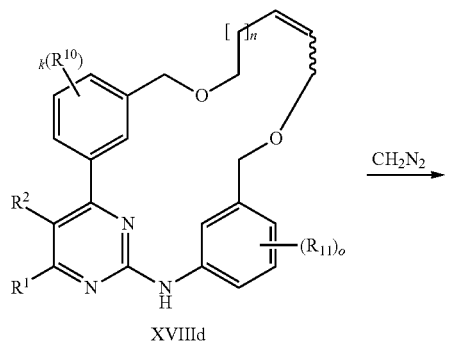

XVIIId

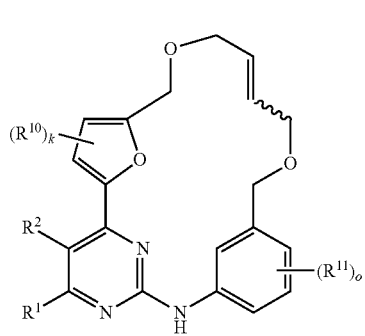

XVIIIf

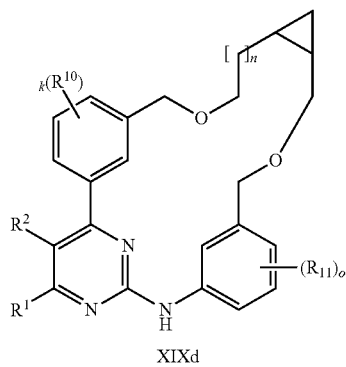

XIXd

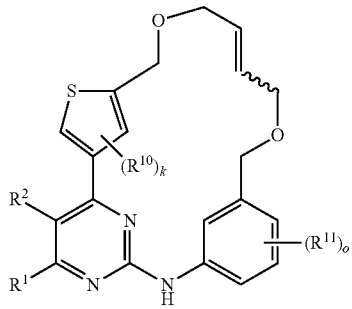

XVIIIg

Coupling of commercially available 2,4-dichloropyrimidine (Ia) under Suzuki coupling conditions with boronic acids of type (XIId) affords biaryl compounds of type (XIIIc), which on treatment with allyl bromides (XIVc) in the presence of a base such as $Cs_2CO_3$ furnish allyl ethers of type (XVd). Substitution with aniline (XVIb) under standard conditions affords terminal alkenes (XVIId), a key intermediate ready for ring closing metathesis (RCM). Employing Grubbs $2^{nd}$ generation catalyst RCM furnishes (XVIIId). Compounds of type (XIXd) are obtained by cyclopropanation under standard conditions.

Synthesis of XVIIIe-i

Macrocycles containing a five membered heterocyclic ring linked to the pyrimidine system can be prepared by a procedure analogous to that described for XVIIId by starting from alternative boronic acids. Structures XVIIIe-i below are representative of compounds of this class.

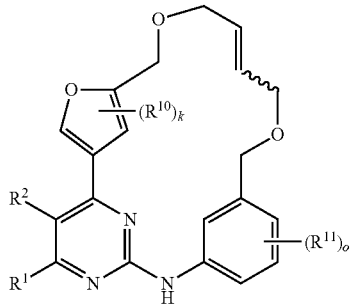

XVIIIh

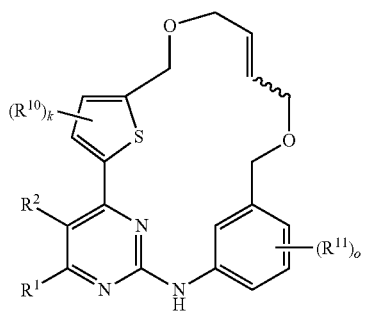

XVIIIe

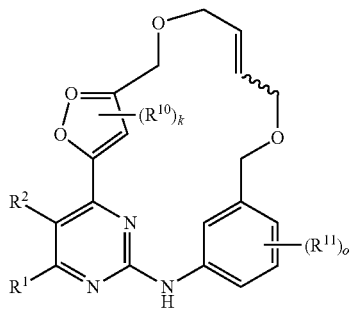

XVIIIi

Scheme 4

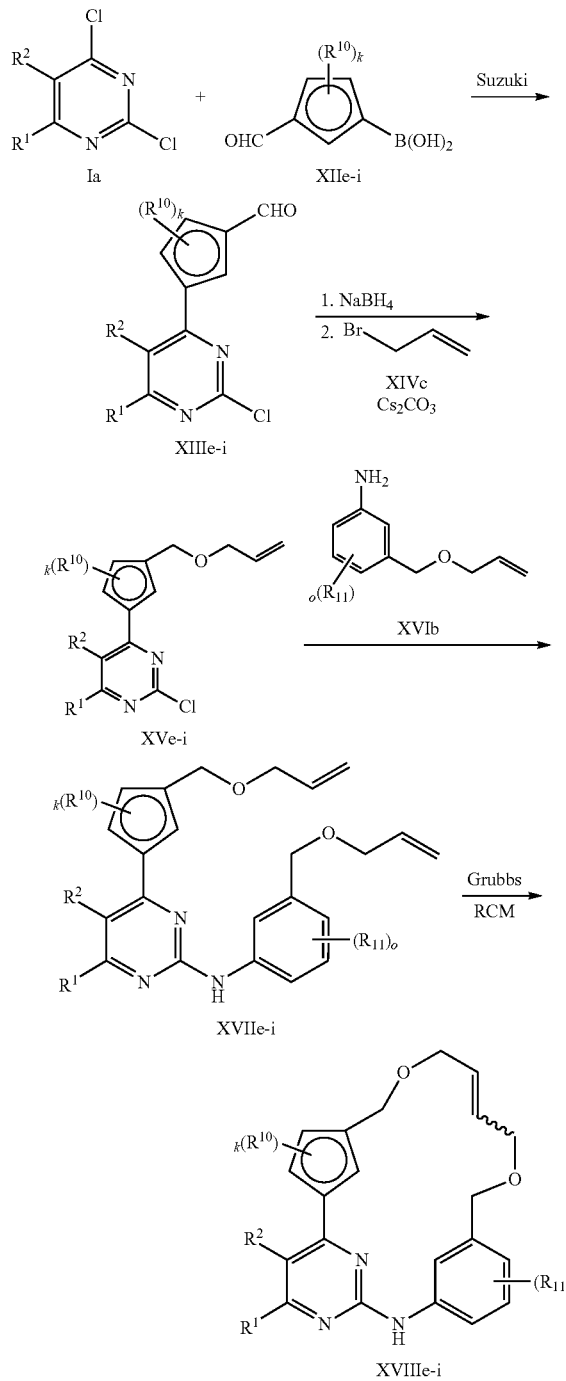

Scheme 4 illustrates the preparation of compounds of type XVIIIe, XVIIIf, XVIIIg and XVIIIh. Coupling of commercially available 2,4-dichloropyrimidine (Ia) under Suzuki coupling conditions with boronic acids of type (XIIe-i) affords biaryl compounds of type (XIIIe-i), which on treatment with allyl bromides (XIVc) in the presence of a base such as $Cs_2CO_3$ furnish allyl ethers of type (XVe-h). Reaction aniline (XVIb) under standard conditions followed by ring closing metathesis (RCM) employing Grubbs $2^{nd}$ generation catalyst then furnishes the desired products (XVIIIe-i).

Representative Procedure for the Synthesis of Compounds Type (XVIIIb)

3-(2-Chloro-pyrimidin-4-yl)-phenol (XIIIa1)

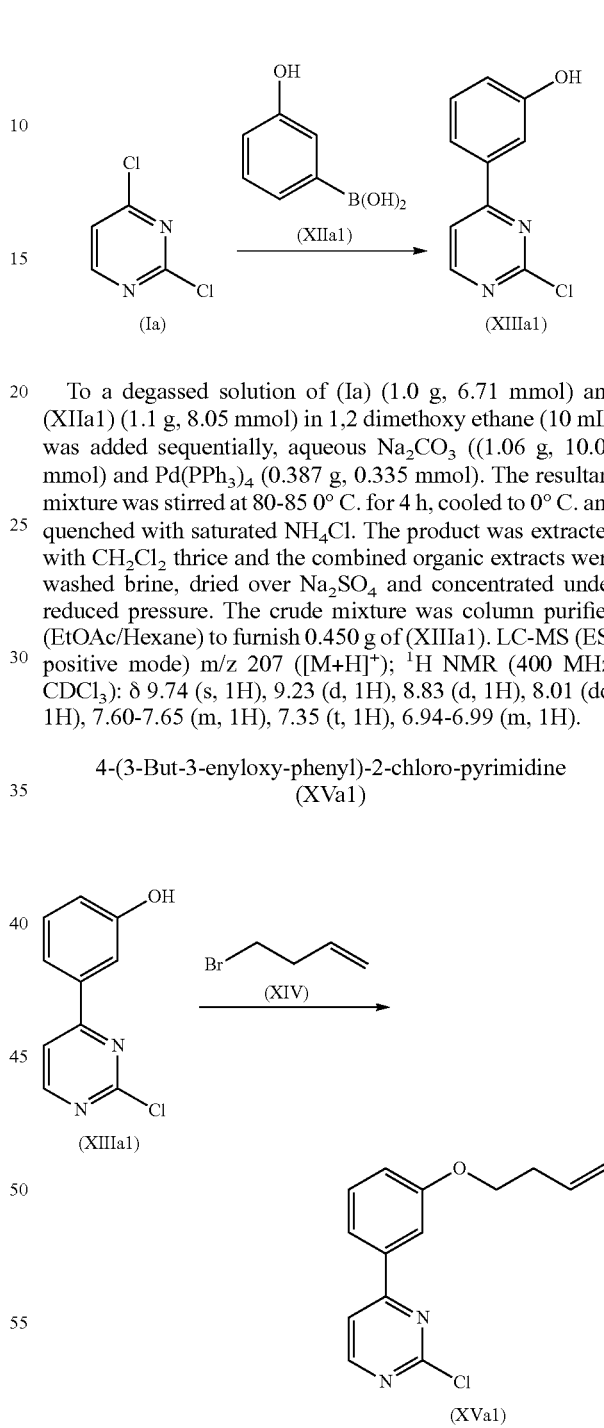

To a degassed solution of (Ia) (1.0 g, 6.71 mmol) and (XIIa1) (1.1 g, 8.05 mmol) in 1,2 dimethoxy ethane (10 mL) was added sequentially, aqueous $Na_2CO_3$ ((1.06 g, 10.06 mmol) and $Pd(PPh_3)_4$ (0.387 g, 0.335 mmol). The resultant mixture was stirred at 80-85 0° C. for 4 h, cooled to 0° C. and quenched with saturated $NH_4Cl$. The product was extracted with $CH_2Cl_2$ thrice and the combined organic extracts were washed brine, dried over $Na_2SO_4$ and concentrated under reduced pressure. The crude mixture was column purified (EtOAc/Hexane) to furnish 0.450 g of (XIIIa1). LC-MS (ESI positive mode) m/z 207 ([M+H]$^+$); $^1$H NMR (400 MHz, $CDCl_3$): δ 9.74 (s, 1H), 9.23 (d, 1H), 8.83 (d, 1H), 8.01 (dd, 1H), 7.60-7.65 (m, 1H), 7.35 (t, 1H), 6.94-6.99 (m, 1H).

4-(3-But-3-enyloxy-phenyl)-2-chloro-pyrimidine (XVa1)

To a mixture of (XIIIa1) (2.0 g, 9.68 mmol) and (XIV) (7.8 g, 5.80 mmol) in dry DMF (10 mL) at ambient temperature was added cesium carbonate (14.19 g, 43.55 mmol) and the resulting mixture was stirred at 40° C. for 6 h. The reaction mixture was cooled to 0° C. and quenched with $H_2O$. The product was extracted with $CH_2Cl_2$ thrice and the combined organic extracts were washed with $H_2O$ followed by brine, dried over Na₂SO₄ and concentrated under reduced pressure to furnish an oil, which was purified by column (EtOAc/Hexane) to obtain 1.61 g of (XVa1). LC-MS (ESI positive mode) m/z 261 ([M+H]⁺); ¹H NMR (400 MHz, DMSO d₆): δ 8.82 (d, 1H), 8.12 (d, 1H), 7.77 (d, 1H), 7.70 (br s, 1H), 7.48 (t, 1H), 7.18 (dd, 1H), 5.86-5.98 (m, 1H), 5.16-5.24 (m, 1H), 5.09-5.13 (m, 1H), 4.13 (t, 2H), 2.49-2.56 (m, 2H).

(3-Nitro-phenyl)-methanol (XXIb)

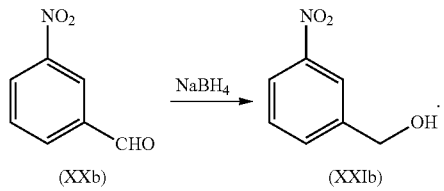 [SMILES: O=Cc1cccc([N+](=O)[O-])c1 ; "NaBH4" ; O=[N+]([O-])c1cccc(CO)c1]

To a solution of (XXb) (5 g, 33.1 mmol) in MeOH (25 mL) at ambient temperature was added NaBH₄ (1.25 g, 33.1 mmol) and the resulting mixture was stirred for 30 min. The reaction mixture was quenched with water. The product was extracted with CH₂Cl₂ thrice and the combined organic extracts were washed with H₂O followed by brine, dried over Na₂SO₄ and concentrated under reduced pressure to furnish without purification 5 g of compound (XXIb). LC-MS (ESI positive mode) m/z 154 ([M+H]⁺); ¹H NMR (CDCl₃) δ 8.27 (s, 1H), 8.17 (dd, 1H), 7.73 (dd, 1H), 7.57 (t, 1H), 4.85 (s, 2H), 2.07 (s, 1H).

1-Allyloxymethyl-3-nitro-benzene (XXIIb)

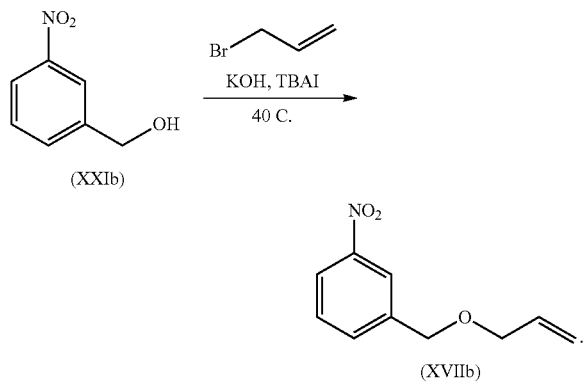

To a mixture of (XXIb) (5 g, 32.6 mmol) and allyl bromide (11.3 ml, 130.4 mmol) at ambient temperature was added KOH (3.65 g, 65.2 mmol) and TBAI (602 mg, 1.63 mmol) and the resulting mixture was stirred at 40° C. overnight. The reaction mixture was cooled and quenched with H₂O. The product was extracted with CH₂Cl₂ thrice and the combined organic extracts were washed with H₂O followed by brine, dried over Na₂SO₄ and concentrated under reduced pressure to furnish an oil, which was purified by column (EtOAc/Hexane:9/1) to obtain 6.3 g of (XXIIb). LC-MS (ESI positive mode) m/z 194 ([M+H]⁺); ¹H NMR (CDCl₃) δ 8.27 (s, 1H), 8.18 (dd, 1H), 7.73 (dd, 1H), 7.57 (t, 1H), 6.01 (m, 1H), 5.38 (m, 1H,), 5.29 (m, 1H,), 4.65 (s, 2H), 4.13 (dt, 2H).

3-Allyloxymethyl-phenylamine (XVIb1)

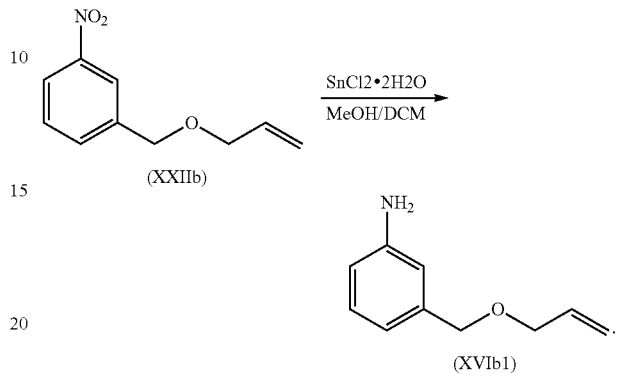

To a solution of (XXIIb) (10 g, 51.75 mmol) in MeOH/CH₂Cl₂ (1:1, 150 mL) at ambient temperature was added SnCl₂.2H₂O (46.7 g, 207 mmol) and the resulting mixture was stirred overnight. The reaction mixture was cooled to 0° C. and quenched with saturated Na₂CO₃. The product was extracted with CH₂Cl₂ thrice and the combined organic extracts were washed with H₂O followed by brine, dried over Na₂SO₄ and concentrated under reduced pressure to furnish an oil, which was purified by column (EtOAc/Hexane:5/1) to obtain 6.80 g of (XVIb1) in 80% yield. LC-MS (ESI positive mode) m/z 164 ([M+H]⁺); ¹H NMR (CDCl₃) δ 7.17 (t, 1H), 6.79 (m, 2H), 6.68 (d, 1H), 5.95-6.06 (m, 1H), 5.33 (m, 1H), 5.29 (m, 1H), 4.49 (s, 2H), 4.06 (m, 2H), 3.38 (s, 2H).

(3-Allyloxymethyl-phenyl)-[4-(3-but-3-enyloxy-phenyl)-pyrimidin-2-yl]-amine (XVIIb1)

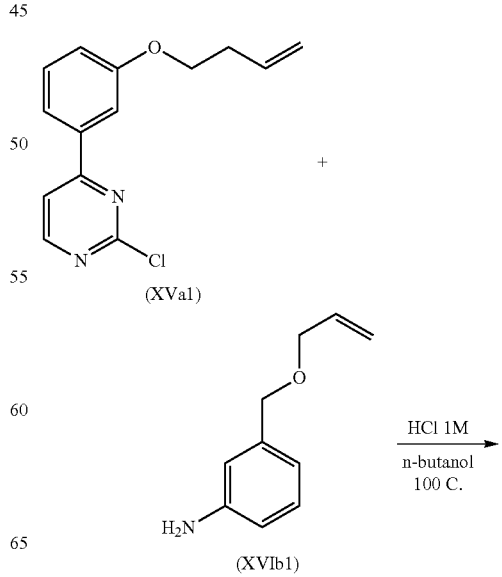

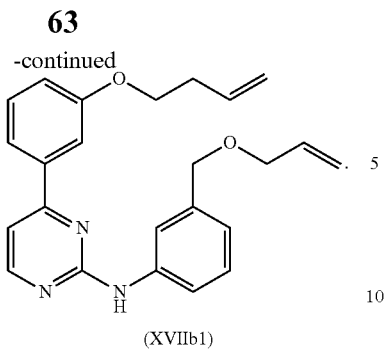

(XVIIb1)

To a mixture of (XVa1) (100 mg, 0.38 mmol) and (XVIb1) (93.9 mg, 0.57 mmol) in n-butanol (15 mL) at ambient temperature was added 1N HCl (1.0 mL) and the resulting mixture was stirred at 100° C. for overnight. The reaction mixture was cooled to 0° C. and quenched with $H_2O$. The product was extracted with $CH_2Cl_2$ thrice and the combined organic extracts were washed with saturated $NaHCO_3$ followed by brine, dried over $Na_2SO_4$ and concentrated under reduced pressure to furnish an oil, which was purified by column (EtOAc/Hexane) to obtain 70 mg of (XVIIb1) in 47%. $^1$H NMR (CDCl$_3$) δ 8.38 (d, 1H), 7.59-7.62 (m, 3H), 7.58 (d, 1H), 7.41 (s, 1H), 7.32 (t, 1H), 7.26 (t, 1H), 7.08 (d, 1H), 6.96-6.98 (m, 2H), 5.80-5.94 (m, 2H), 5.25 (m, 1H), 5.10-5.15 (m, 2H), 5.06 (m, 1H), 4.48 (s, 2H), 4.04 (t, 2H), 3.99 (m, 2H), 2.50 (m, 2H).

Macrocycle Example 1

Compound 1

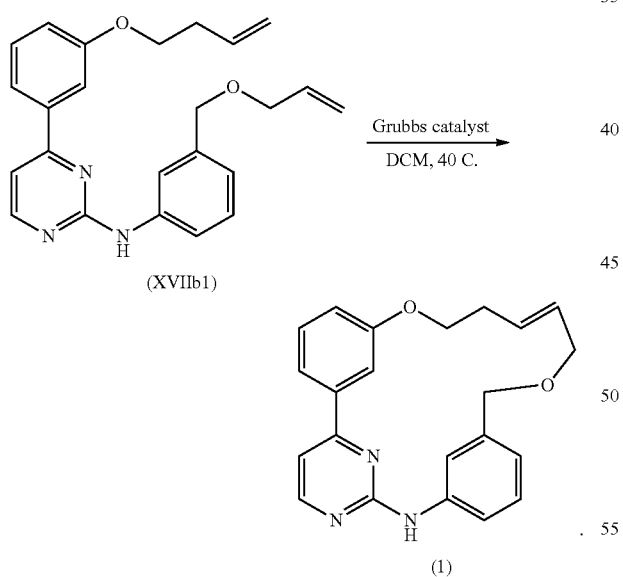

To a degassed solution of (XVIIb1) (20 mg, 0.05 mmol) and TFA (14 mg, 0.125 mmol) in $CH_2Cl_2$ (200 mL) at ambient temperature was added Grubbs 2$^{nd}$ generation catalyst (7 mg, 0.005 mmol). The resulting mixture was stirred at 50° C. for overnight. The reaction mixture was cooled and concentrated under reduced pressure to furnish an oil, which was purified by preparative HPLC to obtain 9 mg of (1). HPLC purity at 254 nm: 95%; LC-MS (ESI positive mode) m/z 360 ([M+H]$^+$); $^1$H NMR (CDCl$_3$) δ 11.75 (s, 1H), 8.38 (m, 1H), 8.18 (d, 1H), 7.92 (m, 1H), 7.41-7.42 (m, 1H), 7.30 (t, 1H), 7.23 (d, 1H, CH), 7.10-7.20 (m, 3H), 5.61-5.73 (m, 2H, $J_{trans}$=16.0 Hz), 4.51 (s, 2H), 4.11 (t, 2H), 4.08 (d, 2H), 2.48 (q, 2H).

Representative Procedure for the Synthesis of Compounds Type (XVIIIc)

1-Allyloxy-3-nitro-benzene (XXIIc)

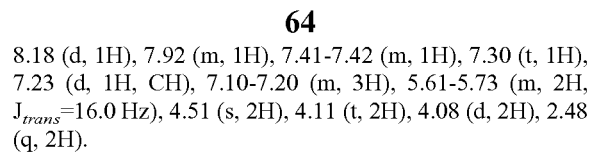

Compound (XXIIc) was obtained using the same procedure described for compound (XXIIb); LC-MS (ESI positive mode) m/z 180 ([M+H]$^+$).

3-Allyloxy-phenylamine (XVIc1)

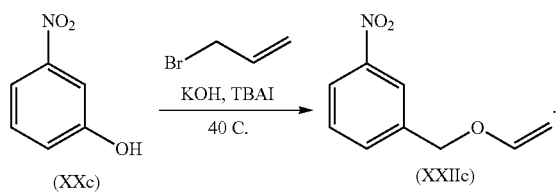

Compound (XVIc1) was obtained using the same procedure described for compound (XVIb1) LC-MS (ESI positive mode) m/z 150 ([M+H]$^+$).

(3-Allyloxy-phenyl)-[4-(3-but-3-enyloxy-phenyl)-pyrimidin-2-yl]-amine (XVIIc1)

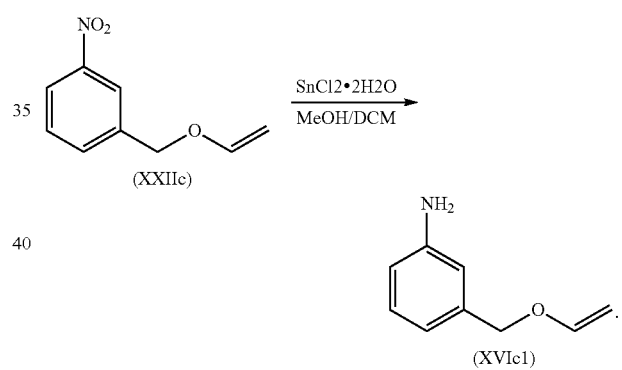

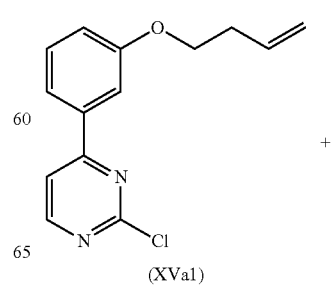

(XVa1)

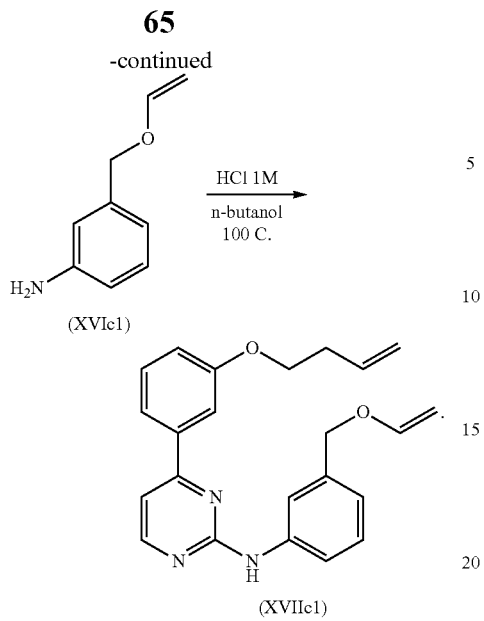

Compound (XVIIc1) was obtained using the same procedure described for compound (XVIIb1); LC-MS (ESI positive mode) m/z 374 ([M+H]⁺).

Macrocycle Example 2

Compound 12

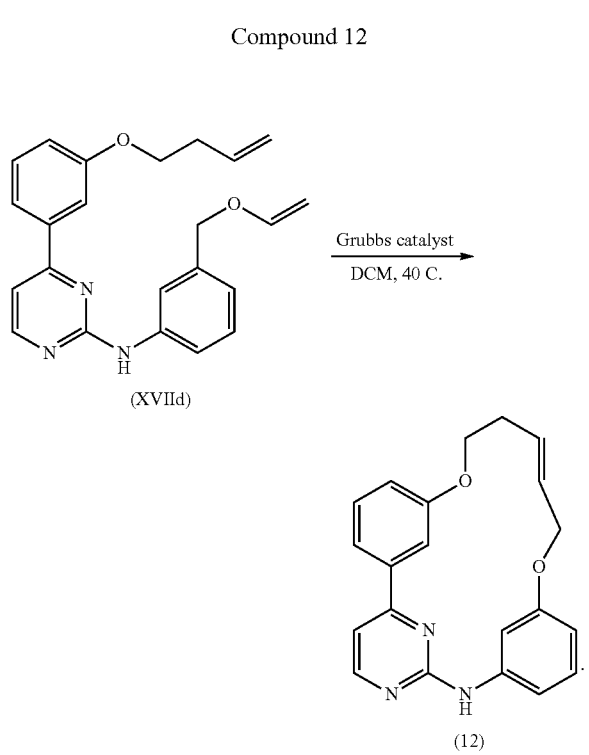

Compound (12) was obtained using the same procedure described for compound (I) HPLC purity at 254 nm: 99%; LC-MS (ESI positive mode) m/z 346 ([M+H]⁺); $^1$H NMR (CDCl$_3$) δ 11.30 (s, 1H), 8.29 (d, 1H), 8.21 (t, 1H), 8.11 (t, 1H), 7.57 (d, 1H), 7.48 (t, 1H), 7.32-7.35 (m, 2H), 7.22-7.25 (m, 1H), 6.95 (dd, 1H), 6.82 (dd, 1H), 6.02-6.08 (m, 1H, CH=, J$_{trans}$=11 Hz), 5.87-5.93 (m, 1H, CH=, J$_{trans}$=11 Hz), 4.78 (d, 2H), 4.29 (t, 2H), 2.63-2.68 (m, 2H).

Representative Procedure for the Synthesis of Compounds Type (XVIIId)

[3-(2-Chloro-pyrimidin-4-yl)-phenyl]-methanol (XIIIa2)

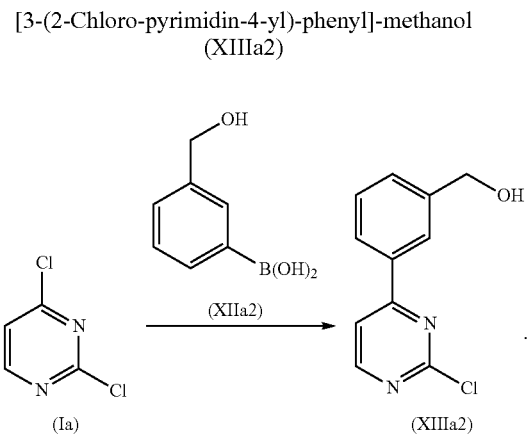

Compound (XIIIa2) was obtained using the same procedure described for compound (XIIIa1); LC-MS (ESI positive mode) m/z 221 ([M+H]⁺).

4-(3-Allyloxymethyl-phenyl)-2-chloro-pyrimidine (XVa2)

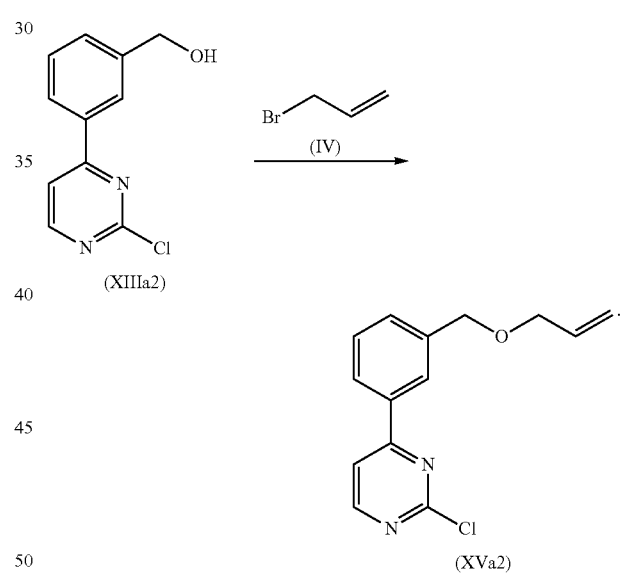

Compound (XVa2) was obtained using the same procedure described for compound (XVa1); LC-MS (ESI positive mode) m/z 271 ([M+H]⁺).

2-(2-Chloro-ethoxy)-5-nitro-benzaldehyde (XXId)

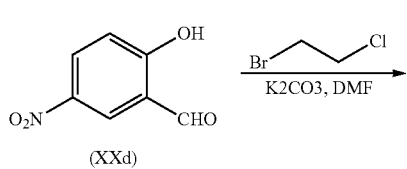

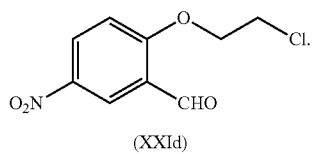
(XXId)

To a mixture of (XXd) (1.0 g, 5.98 mmol) and bromochloroethane (996 L, 11.96 mmol) in dry DMF (15 mL) at ambient temperature was added potassium carbonate (1.64 gg, 11.96 mmol) and the resulting mixture was stirred at 60° C. overnight. The reaction mixture was cooled to 0° C. and quenched with $H_2O$. The product was extracted with $CH_2Cl_2$ thrice and the combined organic extracts were washed with $H_2O$ followed by brine, dried over $Na_2SO_4$ and concentrated under reduced pressure to furnish 1.29 g of a yellow solid (XXId) in 94% yield. LC-MS (ESI positive mode) m/z 229 ([M+H]$^+$); $^1$H NMR (CDCl$_3$) δ 10.56 (s, 1H), 8.78 (d, 1H), 8.50 (dd, 1H), 7.15 (d, 1H), 4.54 (t, 2H), 3.99 (t, 2H).

[2-(2-Chloro-ethoxy)-5-nitro-phenyl]-methanol (XXIId)

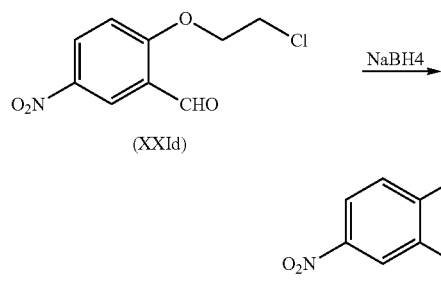

Compound (XXIId) was obtained using the same procedure described for compound (XXIb). LC-MS (ESI positive mode) m/z 232 ([M+H]$^+$).

2-Allyloxymethyl-1-(2-chloro-ethoxy)-4-nitro-benzene (XXIIId)

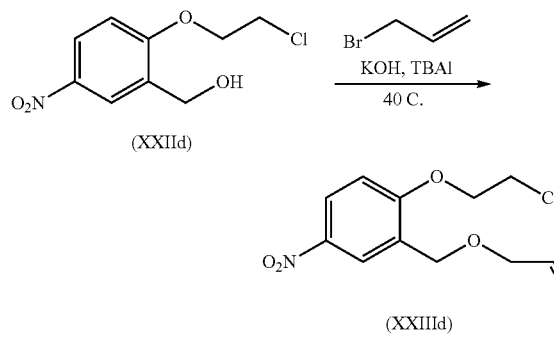

Compound (XXIIId) was obtained using the same procedure described for compound (XXIIb); LC-MS (ESI positive mode) m/z 272 ([M+H]$^+$).

1-[2-(2-Allyloxymethyl-4-nitro-phenoxy)-ethyl]-pyrrolidine (XXIVd)

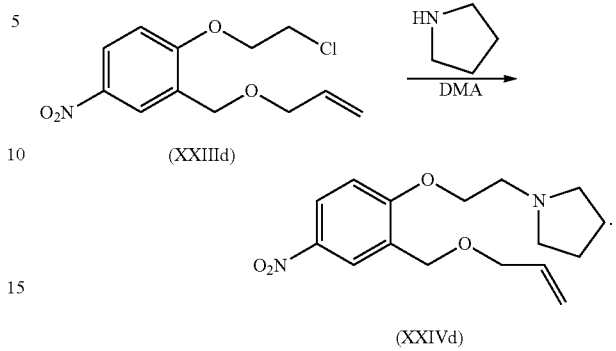

To a solution of (XXIIId) (1 g, 3.68 mmol) in DMA (10 mL) was added pyrrolidine (0.61 mL, 7.36 mmol) and the resulting mixture was stirred overnight at 60° C. The reaction mixture was quenched with water. The product was extracted with $CH_2Cl_2$ thrice and the combined organic extracts were washed with $H_2O$ followed by brine, dried over $Na_2SO_4$ and concentrated under reduced pressure to furnish without purification 750 mg of compound (XXIVd) with 70% yield. LC-MS (ESI positive mode) m/z 307 ([M+H]$^+$).

3-Allyloxymethyl-4-(2-pyrrolidin-1-yl-ethoxy)-phenylamine (XVIb2)

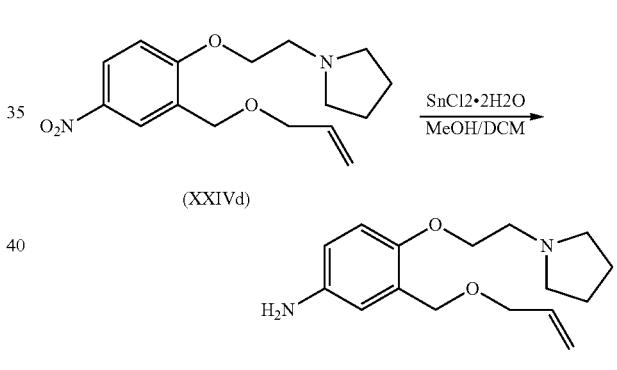

Compound (XVIb2) was obtained using the same procedure described for compound (XVIb); LC-MS (ESI positive mode) m/z 277 ([M+1-1]$^+$).

[4-(3-Allyloxymethyl-phenyl)-pyrimidin-2-yl]-[3-allyloxymethyl-4-(2-pyrrolidin-1-yl-ethoxy)-phenyl]-amine (XVIId1)

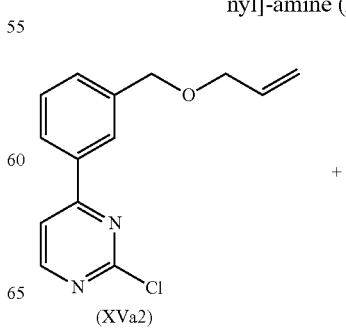

+

-continued

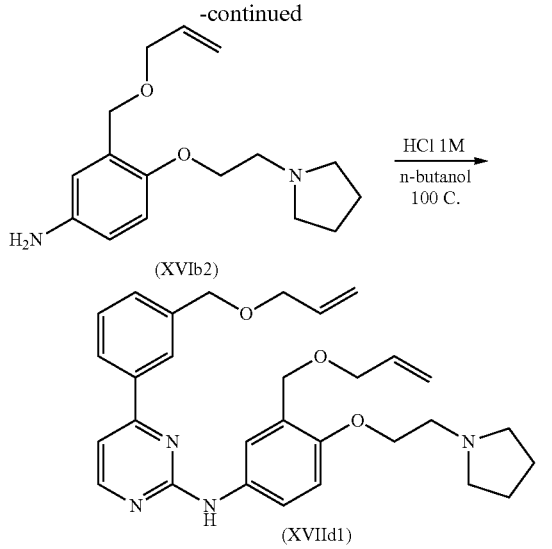

Compound (XVIId1) was obtained using the same procedure described for compound (XVIIb1); LC-MS (ESI positive mode) m/z 501.

Macrocycle Example 3

Compound 13

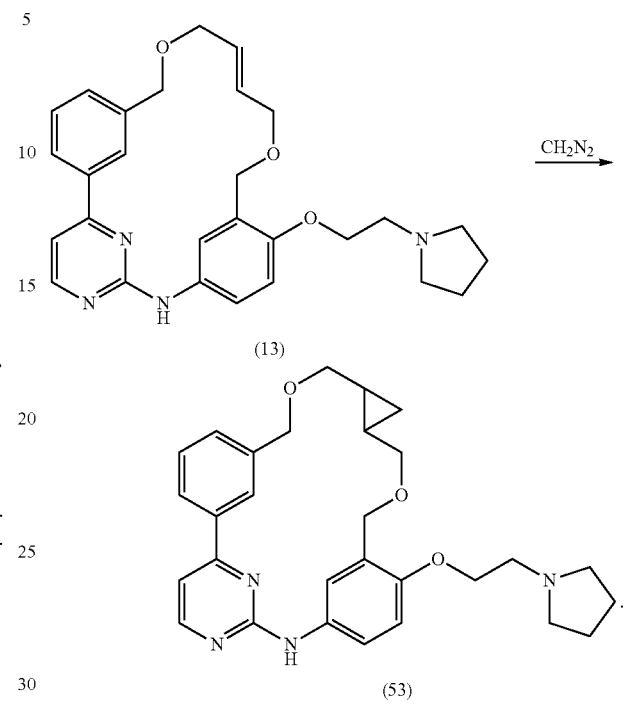

Compound (13) was obtained using the same procedure described for compound (1) HPLC purity at 254 nm: 99%; LC-MS (ESI positive mode) m/z 473 ([M+H]$^+$); $^1$H NMR (MeOD-d$_4$) δ 8.79 (d, 1H), 8.46 (d, 1H), 8.34-8.31 (m, 1H), 7.98-7.96 (m, 1H), 7.62-7.49 (m, 2H), 7.35 (d, 1H), 7.15-7.10 (m, 1H), 7.07-7.02 (m, 1H), 5.98-5.75 (m, 2H, 2×=CH), 4.67 (s, 2H), 4.67 (s, 2H), 4.39-4.36 (m, 2H), 4.17 (d, 2H), 4.08 (d, 2H), 3.88-3.82 (m, 2H), 3.70 (t, 2H), 2.23-2.21 (m, 2H), 2.10-2.07 (m, 2H).

Macrocycle Example 4

Compound 53

To solution of (13) (0.02 g) in CH$_2$Cl$_2$ (2 mL) dioxane mixture (1 mL) at 0° C. was added 5 mole % of Pd(OAc)$_2$. Then freshly prepared ethereal solution of CH$_2$N$_2$ was added slowly. The resulting mixture was stirred at 0° C. for 3 h. The reaction mixture was then concentrated under reduced pressure to furnish oil, which was purified by preparative HPLC to obtain 0.005 g of (53). (CDCl$_3$) δ 8.78 (br s, 1H), 8.63 (br s, 1H), 8.42 (d, 1H), 7.79 (d, 1H), 7.50 (d, 1H), 7.42 (t, 1H), 7.18 (d, 1H), 6.83 (m, 2H), 5.12 (d, 1H), 4.87 (d, 1H), 4.72 (d, 1H), 4.61 (d, 1H), 4.14-4.19 (m, 2H), 4.03-4.07 (m, 2H), 2.99 (t, 2H), 2.81-2.86 (m, 1H), 2.74 (br s, 4H), 2.66-2.71 (m, 1H), 1.81-1.86 (m, 4H), 1.04-1.15 (m, 2H), 0.28-0.33 (m, 1H), 0.15-0.20 (m, 1H).

Representative Procedure for the Synthesis of Compounds Type (XVIIIe)

5-(2-Chloro-pyrimidin-4-yl)-thiophene-2-carbaldehyde (XIIIe1)

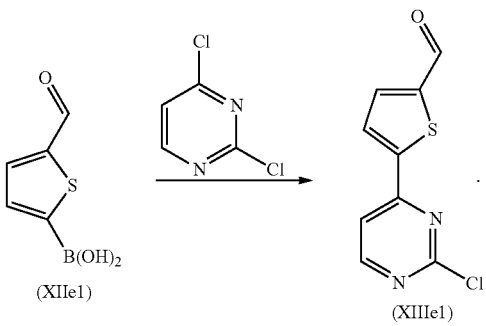 [SMILES: O=Cc1ccc(B(O)O)s1 ; Clc1ccnc(Cl)n1 ; O=Cc1ccc(-c2ccnc(Cl)n2)s1]

To a solution of 1,4 dioxane, 2,4 dichloropyrimidine was added and the reaction evacuated & purged with N$_2$. Then dppf catalyst ([1,1'-Bis(diphenylphosphino)ferrocene] dichloropalladium(II) was added and the system was evacuated and purged with N$_2$ again. Then (XIIe1) and saturated bicarbonate solution was added sequentially and the solution stirred at 85° C. under N$_2$ for 1 hr. The solution was cooled and filtered through celite and washed with DCM thrice. The DCM layer was extracted with water. The water layer was extracted with DCM and all DCM layers were dried over Na$_2$SO$_4$ and removed in vacuo. The crude was purified by flash chromatography eluting with 40% ethyl acetate in hexane to yield a pale yellow solid (XIIIe1) (50%). LC-MS (ESI positive mode) m/z 225 ([M+H]$^+$); $^1$H NMR (CDCl$_3$) δ 10.64 (s, 1H), 8.68 (d, 1H), 7.66 (m, 2H), 7.57 (d, 1H).

[5-(2-Chloro-pyrimidin-4-yl)-thiophen-2-yl]-methanol (XIIIe2)

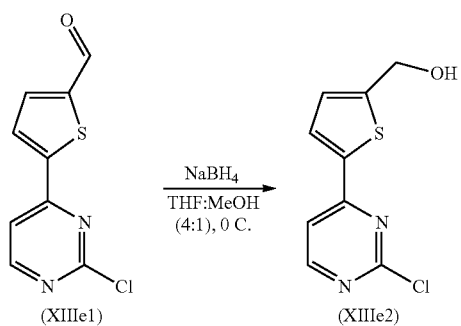

Compound (XIIIe2) was obtained using the same procedure described for compound (XXIb) with a yield of 90%. LC-MS (ESI positive mode) m/z 227 ([M+H]$^+$); $^1$H NMR (CDCl$_3$) δ 8.62 (d, 1H), 7.55 (m, 2H), 7.25 (d, 1H), 4.83 (s, 2H), 4.68 (bs, 1H).

4-(5-Allyloxymethyl-thiophen-2-yl)-2-chloro-pyrimidine (XVe1)

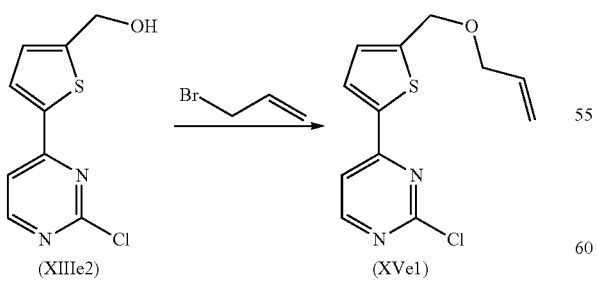

Compound (XVe1) was obtained using the same procedure described for compound (XXIIb) with a yield of 80%. LC-MS (ESI positive mode) m/z 267 ([M+H]$^+$)

[3-Allyloxymethyl-4-(2-pyrrolidin-1-yl-ethoxy)-phenyl]-[4-(5-allyloxymethyl-thiophen-2-yl)-pyrimidin-2-yl]-amine (XVIIe1)

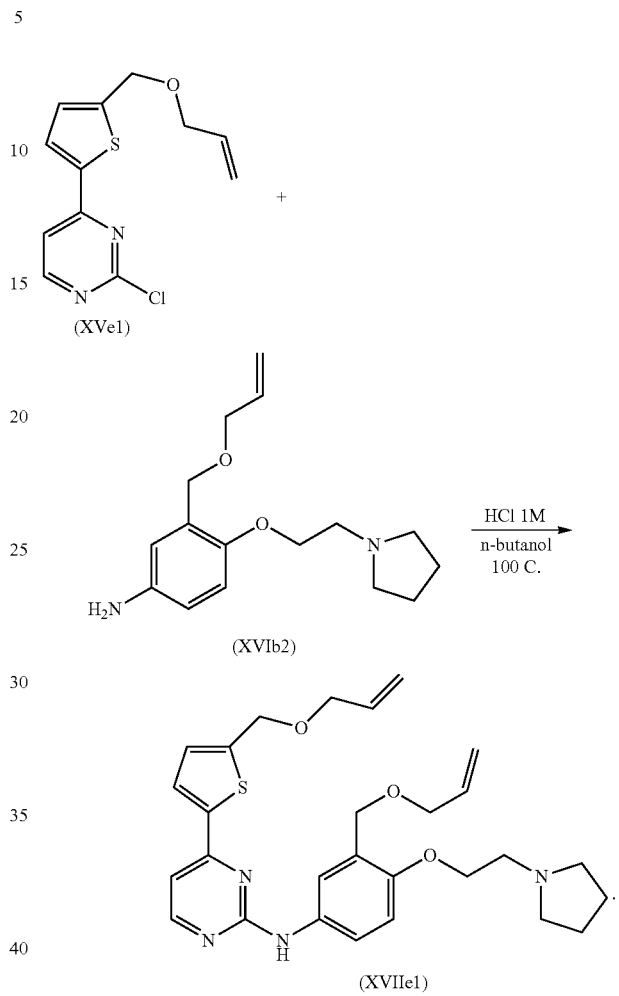

Compound (XVIIe1) was obtained using the same procedure described for compound (XVIIb1); LC-MS (ESI positive mode) m/z 507.

Macrocycle Example 5

Compound 48

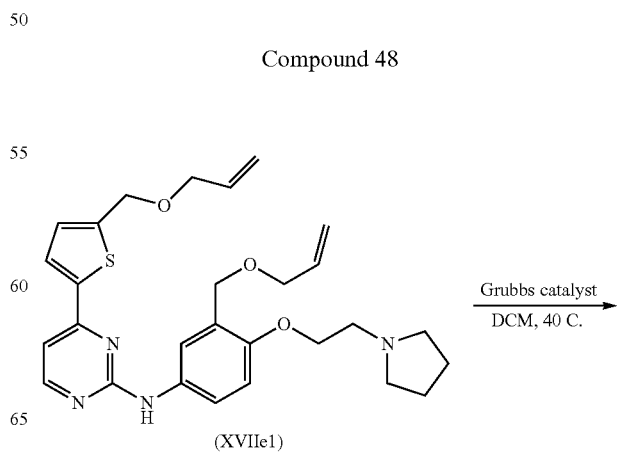

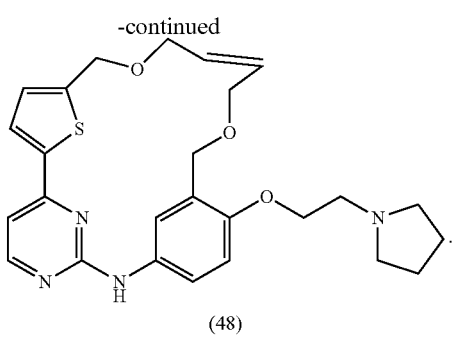

(48)

Compound (48) was obtained using the same procedure described for compound (I) HPLC purity at 254 nm: 100%; LC-MS (ESI positive mode) m/z 479 ([M+H]+); $^1$H NMR (MeOD-d$_4$): δ 8.66 (d, 1H), 8.32 (d, 1H), 7.81 (d, 1H), 7.27 (d, 1H), 7.12 (dd, 1H), 7.07-7.02 (m, 2H), 6.08 (dt, 1H, CH, J=4.4 Hz, J$_{trans}$=15.6 Hz), 5.98 (dt, 1H, CH, J=4.6 Hz, J$_{trans}$=15.6 Hz), 4.61 (s, 2H), 4.38 (t, 2H), 4.18 (d, 4H), 3.81 (br s, 2H), 3.69 (t, 2H), 3.37-3.35 (m, 2H), 2.22-2.08 (m, 6H).

Representative Procedure for the Synthesis of Compounds Type (XVIIIf)

5-(2-Chloro-pyrimidin-4-yl)-furan-2-carbaldehyde (XIIIf1)

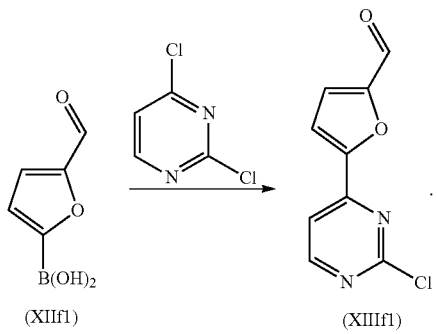

Compound (XIIIf1) was obtained using the same procedure described for compound (XIIIe1); LC-MS (ESI positive mode) m/z 209 ([M+H]+)

[5-(2-Chloro-pyrimidin-4-yl)-furan-2-yl]-methanol (XIIIf2)

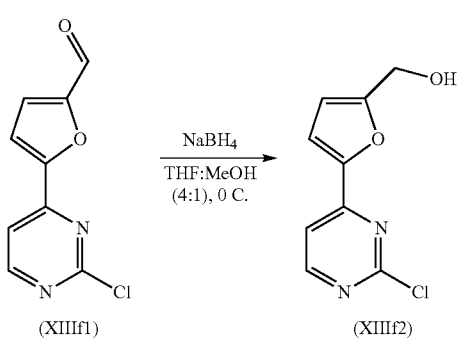

Compound (XIIIf2) was obtained using the same procedure described for compound (XXIb); LC-MS (ESI positive mode) m/z 211 ([M+H]+).

4-(5-Allyloxymethyl-furan-2-yl)-2-chloro-pyrimidine (XVf1)

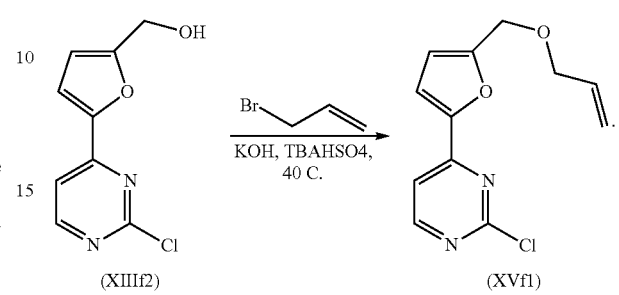

Compound (XVf1) was obtained using the same procedure described for compound (XXIIb); LC-MS (ESI positive mode) m/z 251 ([M+H]+).

[4-(5-Allyloxymethyl-furan-2-yl)-pyrimidin-2-yl]-[3-allyloxymethyl-4-(2-pyrrolidin-1-yl-ethoxy)-phenyl]-amine (XVIIf1)

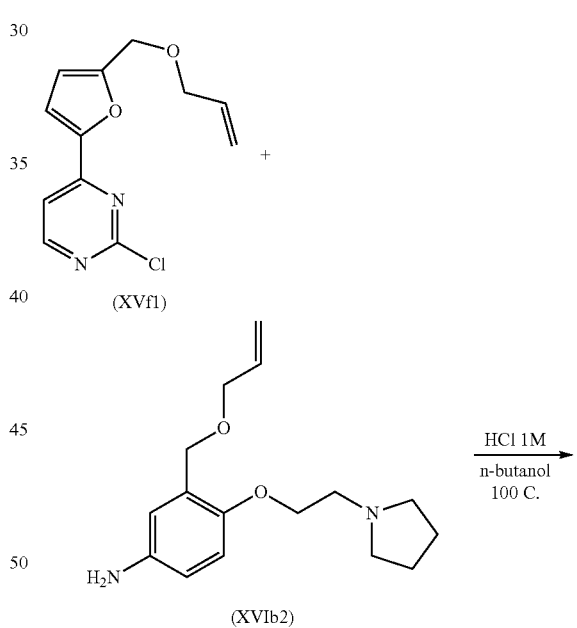

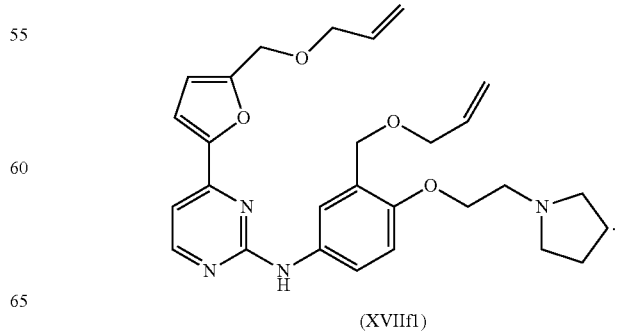

(XVIIf1)

Compound (XVIIf1) was obtained using the same procedure described for compound (XVIIb1); LC-MS (ESI positive mode) m/z 491.

Macrocycle Example 6

Compound 38

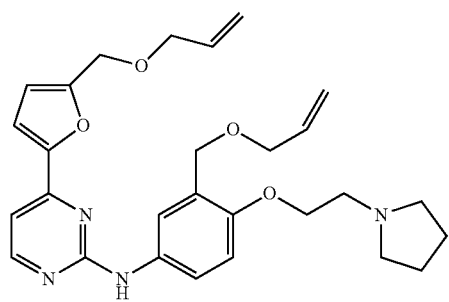

(XVIIf1)

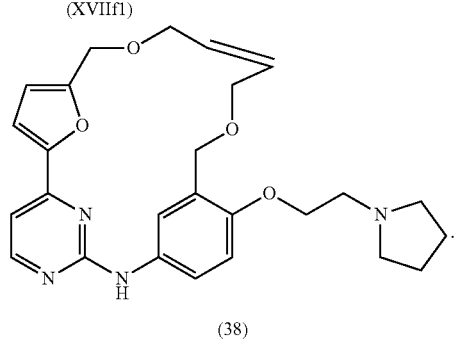

(38)

Compound (38) was obtained using the same procedure described for compound (1) HPLC purity at 254 nm: 99%; LC-MS (ESI positive mode) m/z 463 ([M+H]$^+$); $^1$H NMR (MeOD-d$_4$) δ 8.90 (d, 1H), 8.33 (d, 1H), 7.37 (d, 1H), 7.17 (d, 1H), 7.14-7.11 (m, 1H), 7.04 (d, 1H), 6.67 (d, 1H), 6.04 (dt, 1H, CH, J=5.2 Hz, J$_{trans}$=15.8 Hz), 5.96 (dt, 1H, CH, J=5.0 Hz, J$_{trans}$=15.8 Hz), 4.65 (s, 2H), 4.62 (s, 2H), 4.37 (t, 2H), 4.14 (d, 2H), 4.09 (d, 2H), 3.81 (br s, 2H), 3.66 (t, 2H), 3.33 (s, 2H), 2.21-1.98 (m, 4H).

Representative Procedure for the Synthesis of Compounds Type (XVIIIg1)

4-(2-Chloro-pyrimidin-4-yl)-thiophene-2-carbaldehyde (XIIIg1)

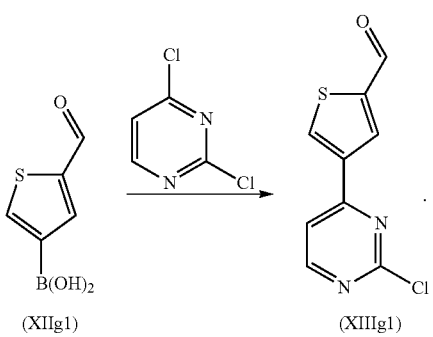

Compound (XIIIg1) was obtained using the same procedure described for compound (XIIIe1); LC-MS (ESI positive mode) m/z 225 ([M+H]$^+$).

[4-(2-Chloro-pyrimidin-4-yl)-thiophen-2-yl]-methanol (XIIIg2)

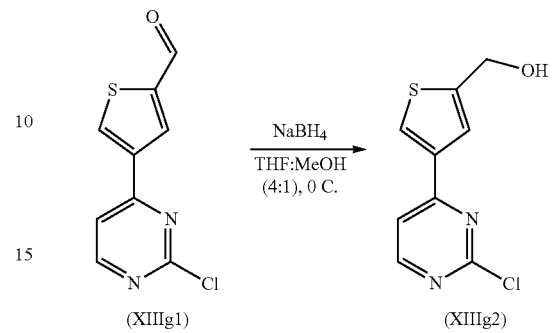

Compound (XIIIg2) was obtained using the same procedure described for compound (XXIb); LC-MS (ESI positive mode) m/z 227 ([M+H]$^+$).

4-(5-Allyloxymethyl-thiophen-3-yl)-2-chloro-pyrimidine (XVg1)

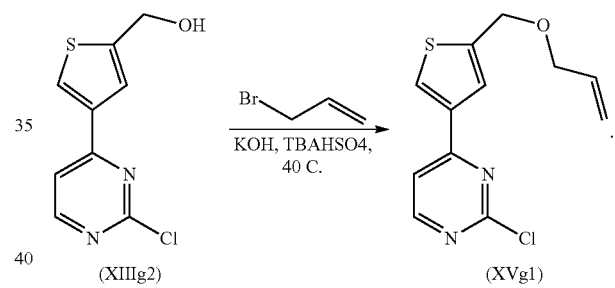

Compound (XVg1) was obtained using the same procedure described for compound (XXIIb); LC-MS (ESI positive mode) m/z 267 ([M+H]$^+$)

[3-Allyloxymethyl-4-(2-pyrrolidin-1-yl-ethoxy)-phenyl]-[4-(5-allyloxymethyl-thiophen-3-yl)-pyrimidin-2-yl]-amine (XVIIg1)

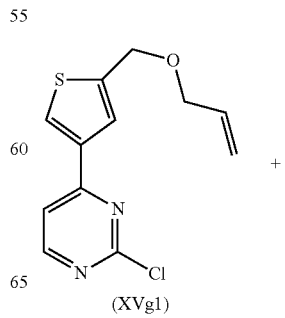

(XVg1)

+

4.65 (d, 2H), 4.54 (d, 2H), 4.29 (br s, 2H), 4.18 (t, 2H), 3.84-3.83 (m, 2H), 2.80-2.48 (m, 4H).

Representative Procedure for the Synthesis of Compounds Type (XVIIIh1)

4-(2-Chloro-pyrimidin-4-yl)-furan-2-carbaldehyde (XIIIh1)

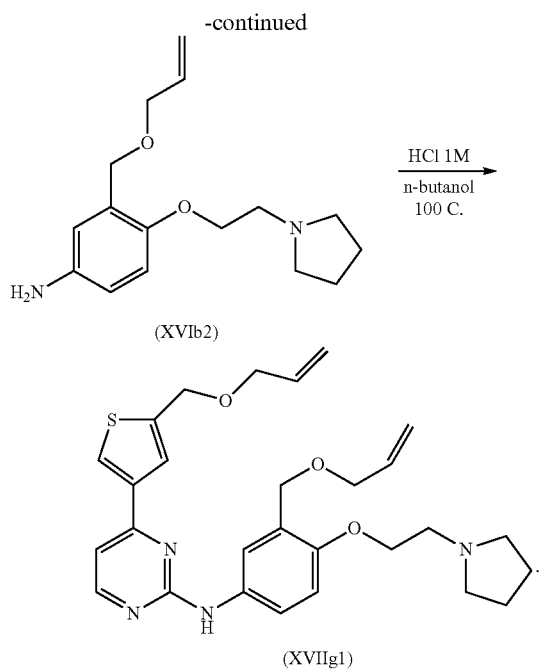

(XVIb2)

(XVIIg1)

Compound (XVIIg1) was obtained using the same procedure described for compound (XVIIb1); LC-MS (ESI positive mode) m/z 507.

Macrocycle Example 7

Compound 52

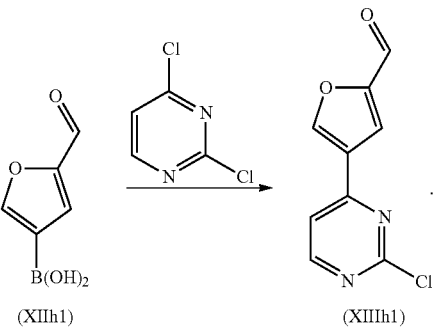

Compound (XIIIh1) was obtained using the same procedure described for compound (XIIIe1); LC-MS (ESI positive mode) m/z 209 ([M+H]$^+$)

[4-(2-Chloro-pyrimidin-4-yl)-furan-2-yl]-methanol (XIIIh2)

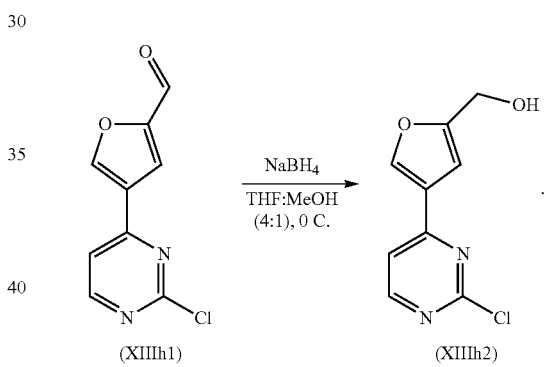

Compound (XIIIh2) was obtained using the same procedure described for compound (XXIb); LC-MS (ESI positive mode) m/z 211 ([M+H]$^+$).

4-(5-Allyloxymethyl-furan-3-yl)-2-chloro-pyrimidine (XVh1)

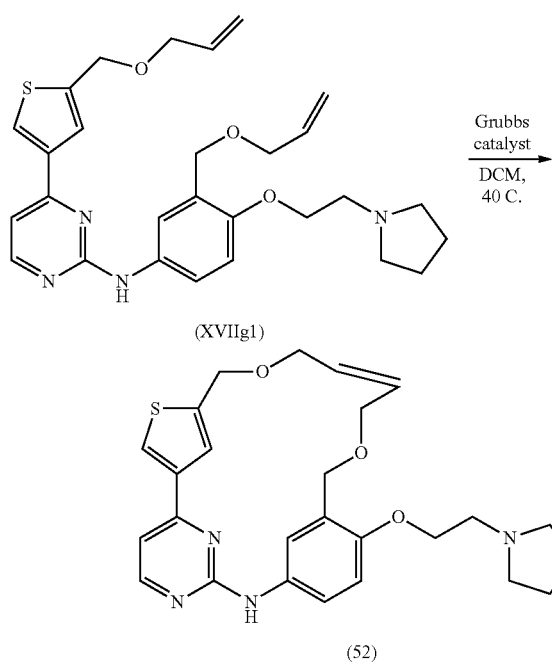

(XVIIg1)

(52)

Compound (52) was obtained using the same procedure described for compound (1) HPLC purity at 254 nm: 99%; LC-MS (ESI positive mode) m/z 479 ([M+H]$^+$); $^1$H NMR (MeOD-d$_4$): δ 9.03 (d, 1H), 8.86 (d, 1H), 8.81 (d, 1H), 8.26 (s, 1H), 7.81 (d, 1H), 7.59 (dd, 1H), 7.56-7.51 (m, 1H), 6.38 (dt, 1H, CH, J=5.7 Hz, J$_{trans}$=15.7 Hz), 6.31 (dt, 1H, CH, J=5.4 Hz, J$_{trans}$=15.7 Hz), 5.24 (s, 2H), 5.14 (s, 2H), 4.86 (t, 2H),

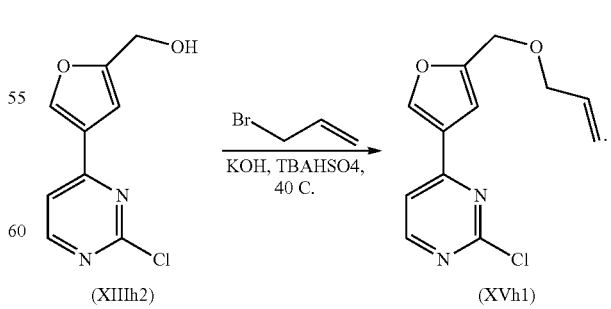

Compound (XVh1) was obtained using the same procedure described for compound (XXIb); LC-MS (ESI positive mode) m/z 251 ([M+H]$^+$).

[4-(5-Allyloxymethyl-furan-3-yl)-pyrimidin-2-yl]-[3-allyloxymethyl-4-(2-pyrrolidin-1-yl-ethoxy)-phenyl]-amine (XVIIh1)

Macrocycle Example 8

Compound 50

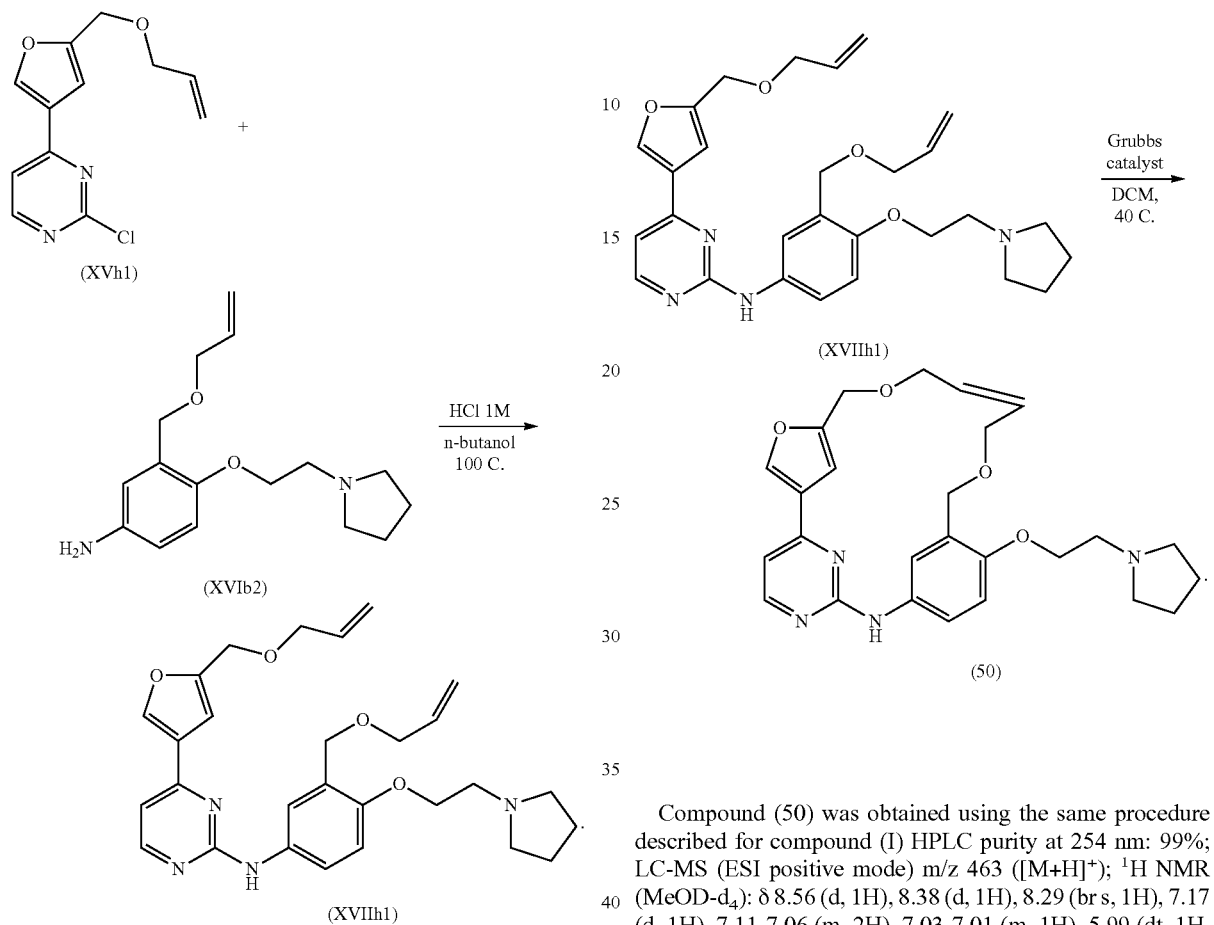

Compound (XVIIh1) was obtained using the same procedure described for compound (XVIIb1); LC-MS (ESI positive mode) m/z 491.

Compound (50) was obtained using the same procedure described for compound (I) HPLC purity at 254 nm: 99%; LC-MS (ESI positive mode) m/z 463 ([M+H]$^+$); $^1$H NMR (MeOD-d$_4$): δ 8.56 (d, 1H), 8.38 (d, 1H), 8.29 (br s, 1H), 7.17 (d, 1H), 7.11-7.06 (m, 2H), 7.03-7.01 (m, 1H), 5.99 (dt, 1H, CH, J=6.0 Hz, J$_{trans}$=15.6 Hz), 5.84 (dt, 1H, CH, J=5.8 Hz, J$_{trans}$=15.6 Hz), 4.66 (s, 2H$_2$), 4.57 (s, 2H), 4.37 (t, 2H), 4.18 (d, 2H), 4.09 (d, 2H), 3.79 (br s, 2H), 3.69 (t, 2H), 3.35-3.34 (m, 2H), 2.21-2.07 (m, 4H).

The compounds outlined in Table 1 were synthesized following the procedures outlined above.

TABLE 1

| No | Structure | $^1$H NMR (400 MHz) | m/z [MH]$^+$ |
|---|---|---|---|
| 1 | 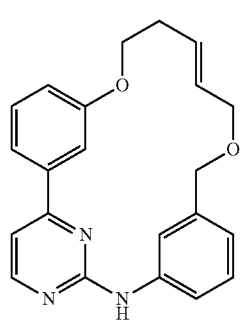 [SMILES: C1=C/COCc2cccc(c2)Nc2nccc(n2)-c2cccc(c2)OCC/1] | (CDCl$_3$) δ 11.75 (s, 1H), 8.38 (m, 1H), 8.18 (d, 1H), 7.92 (m, 1H), 7.41-7.42 (m, 1H), 7.30 (t, 1H), 7.23 (d, 1H), 7.10-7.20 (m, 3H), 5.61-5.73 (m, 2H, J$_{trans}$ = 16.0 Hz), 4.51 (s, 2H), 4.11 (t, 2H), 4.08 (d, 2H), 2.48 (q, 2H). | 360 |

TABLE 1-continued

| No | Structure | ¹H NMR (400 MHz) | m/z [MH]⁺ |
|---|---|---|---|
| 2 | 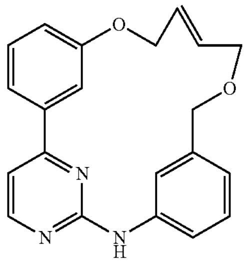 [SMILES: C1=C/COc2cccc(c2)-c2ccnc(n2)Nc2cccc(c2)COC/1] | (CDCl₃) δ 11.81 (s, 1H), 8.15 (m, 1H), 8.14 (d, 1H), 7.60 (m, 1H), 7.36-7.37 (m, 2H), 7.31 (t, 1H), 7.23 (m, 1H), 7.17 (d, 1H), 7.14-7.16 (m, 1H), 7.10 (d, 1H, CH), 6.02 (dt, 1H, CH═, $J_{trans}$ = 16.0 Hz, J = 5.0 Hz), 5.78 (dt, 1H, CH═, $J_{trans}$ = 16.0 Hz, J = 5.0 Hz), 4.61 (d, 2H), 4.47 (s, 2H), 4.05 (d, 2H). | 346 |
| 3 | 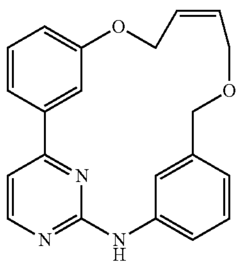 [SMILES: C1=C\COc2cccc(c2)-c2ccnc(n2)Nc2cccc(c2)COC/1] | (CDCl₃) δ 11.82 (s, 1H), 8.13 (d, 1H), 8.08 (s, 1H), 7.94-7.99 (m, 1H), 7.50 (d, 1H), 7.36 (t, 1H), 7.30-7.35 (m, 2H), 7.22-7.24 (m, 1H), 7.16 (d, 1H), 7.12 (d, 1H), 5.78-5.84 (m, 1H, CH═, $J_{cis}$ = 11.0 Hz), 5.66-5.72 (m, 1H, CH═, $J_{cis}$ = 11.0 Hz), 4.89 (d, 2H), 4.45 (s, 2H), 4.15 (d, 2H). | 346 |
| 4 | 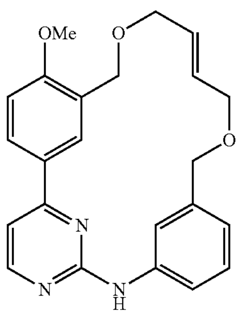 [SMILES: COc1ccc2cc1COC/C=C/COCc1cccc(c1)Nc1nccc-2n1] | (CDCl₃) δ 8.54-8.56 (m, 1H), 8.38 (d, 1H), 8.32 (d, 1H), 7.87 (dd, 1H), 7.14-7.17 (m, 2H), 7.31 (t, 1H), 6.98 (d, 1H), 6.91-6.93 (m, 1H), 5.89-5.93 (m, 2H), 4.62 (s, 2H), 4.61 (s, 2H), 4.16 (d, 2H), 4.11 (d, 2H), 3.95 (s, 3H). | 390 |
| 5 | 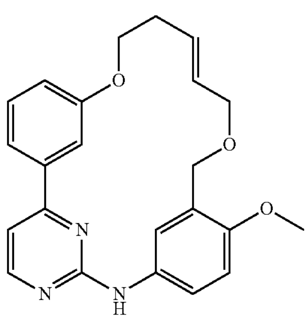 [SMILES: COc1ccc2cc1COC/C=C/CCOc1cccc(c1)-c1ccnc(n1)N2] | Mixture of cis and trans | 390 |
| 6 | 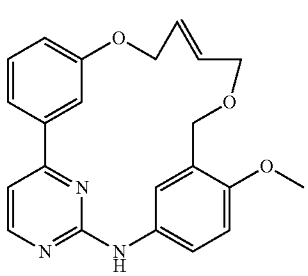 [SMILES: COc1ccc2cc1COC/C=C/COc1cccc(c1)-c1ccnc(n1)N2] | (CDCl₃) δ 11.76 (s, 1H), 8.16 (d, 1H), 8.14 (d, 1H), 7.66 (s, 1H), 7.40-7.42 (m, 2H), 7.28 (dd, 1H), 7.19-7.21 (m, 1H), 7.17 (d, 1H), 6.90 (d, 1H, 6.07-6.14 (m, 1H, ═CH, $J_{trans}$ = 15.7 Hz), 5.82-5.88 (m, 1H, ═CH, $J_{trans}$ = 15.7 Hz), 5.67 (d, 2H), 4.60 (s, 2H), 4.14 (dd, 2H), 3.86 (s, 3H). | 376 |

TABLE 1-continued

| No | Structure | ¹H NMR (400 MHz) | m/z [MH]⁺ |
|---|---|---|---|
| 7 | 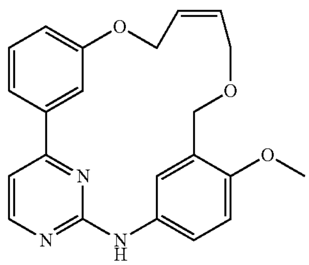 [SMILES: COc1ccc2cc1COC/C=C\COc1cccc(c1)-c1ccnc(n1)N2] | (CDCl₃) δ 11.75 (s, 1H), 8.19 (d, 1H), 7.13 (d, 1H), 8.09 (m, 1H), 7.46 (d, 1H), 7.34 (t, 1H), 7.31-7.32 (m, 2H), 7.25-7.26 (m, 1H), 6.94 (d, 1H, CH, J = 8.7 Hz), 5.79-5.93 (m, 2H), 5.03 (dd, 2H), 4.62 (s, 2H), 4.28 (dd, 2H), 3.90 (s, 3H). | 376 |
| 8 | 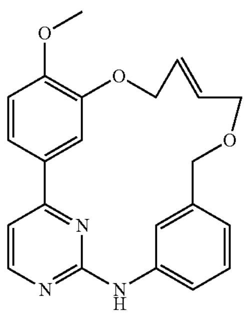 [SMILES: COc1ccc2cc1OC/C=C/COCc1cccc(c1)Nc1nccc-2n1] | Mixture of cis and trans | 376 |
| 9 | 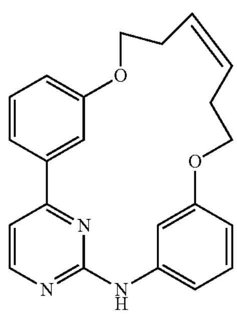 [SMILES: C1=C\CCOc2cccc(c2)-c2ccnc(n2)Nc2cccc(c2)OCC/1] | (DMSO-d₆) δ 9.72 (s, 1H), 8.55 (d, 1H), 8.31 (t, 1H), 7.94 (t, 1H), 7.62 (d, 1H), 7.46 (t, 1H), 7.42 (d, 1H), 7.17 (t, 1H), 7.14 (dd, 1H), 6.80 (dd, 1H), 6.50 (dd, 1H), 5.53-5.65 (m, 2H, 2XCH=, J$_{cis}$ = 8.8 Hz), 4.07 (t, 2H), 3.99 (t, 2H), 2.45-2.50 (m, 4H) | 360 |
| 10 | 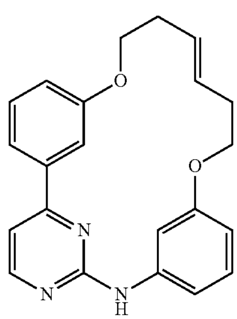 [SMILES: C1=C/CCOc2cccc(c2)-c2ccnc(n2)Nc2cccc(c2)OCC/1] | (DMSO-d₆) δ 9.77 (s, 1H), 8.57 (d, 1H), 8.48 (t, 1H), 8.09 (t, 1H), 7.65 (d, 1H), 7.46 (d, 1H), 7.44 (t, 1H), 7.17 (t, 1H), 7.10 (dd, 1H), 6.84 (dd, 1H), 6.54 (dd, 1H), 5.60-5.68 (m, 2H, 2XCH=), 4.12 (t, 2H), 4.06 (t, 2H), 2.56-2.61 (m, 4H) | 360 |
| 11 | 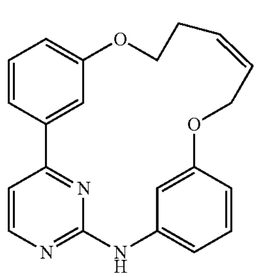 [SMILES: C1=C\COc2cccc(c2)Nc2nccc(n2)-c2cccc(c2)OCC/1] | (CDCl₃) δ 11.30 (s, 1H), 8.20-8.29 (m, 2H), 7.94 (t, 1H), 7.85 (t, 1H), 7.52-7.56 (m, 1H), 7.48 (t, 1H), 7.33-7.35 (m, 1H), 7.23-7.26 (m, 1H), 6.93 (dd, 1H), 6.85 (dd, 1H), 5.97-6.00 (m, 2H), 4.71 (m, 2H), 4.27 (t, 2H), 2.45-2.50 (m, 2H) | 346 |

TABLE 1-continued

| No | Structure | ¹H NMR (400 MHz) | m/z [MH]⁺ |
|----|-----------|------------------|-----------|
| 12 | 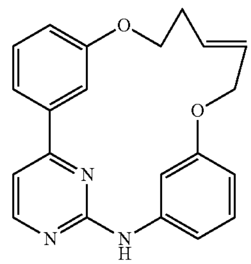 [SMILES: C1=C/COc2cccc(c2)Nc2nccc(n2)-c2cccc(c2)OCC/1] | (CDCl₃) δ 11.30 (s, 1H), 8.29 (d, 1H), 8.21 (t, 1H), 8.11 (t, 1H), 7.57 (d, 1H), 7.48 (t, 1H), 7.32-7.35 (m, 2H, 7.22-7.25 (m, 1H), 6.95 (dd, 1H), 6.82 (dd, 1H), 6.02-6.08 (m, 1H, CH=, $J_{trans}$ = 11 Hz), 5.87-5.93 (m, 1H, CH=, $J_{trans}$ = 11 Hz), 4.78 (d, 2H), 4.29 (t, 2H), 2.63-2.68 (m, 2H) | 346 |
| 13 | 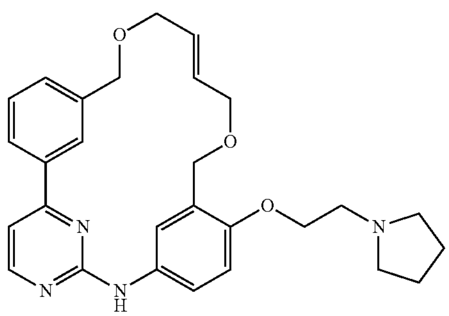 [SMILES: C1=C/COCc2cc(ccc2OCCN2CCCC2)Nc2nccc(n2)-c2cccc(c2)COC/1] | (MeOD-d₄) δ 8.79 (d, 1H), 8.46 (d, 1H), 8.34-8.31 (m, 1H), 7.98-7.96 (m, 1H), 7.62-7.49 (m, 2H), 7.35 (d, 1H), 7.15-7.10 (m, 1H), 7.07-7.02 (m, 1H), 5.98-5.75 (m, 2H, 2x = CH), 4.67 (s, 2H), 4.67 (s, 2H), 4.39-4.36 (m, 2H), 4.17 (d, 2H), 4.08 (d, 2H), 3.88-3.82 (m, 2H), 3.70 (t, 2H), 2.23-2.21 (m, 2H), 2.10-2.07 (m, 2H) | 473 |
| 14 | 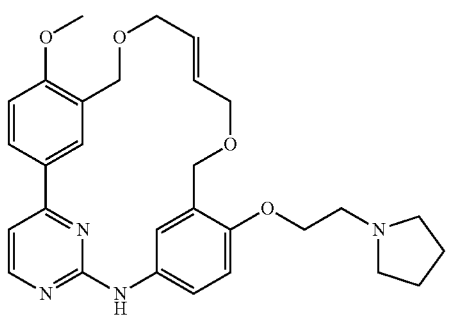 [SMILES: COc1ccc2cc1COC/C=C/COCc1cc(ccc1OCCN1CCCC1)Nc1nccc-2n1] | (MeOD-d₄) δ 8.50-8.48 (m, 1H), 8.37 (d, 1H), 8.27 (d, 1H), 8.07 (dd, 1H), 7.38 (d, 1H), 7.17-7.15 (m, 2H), 7.08-7.06 (m, 1H), 5.98-5.86 (m, 2H), 4.69 (s, 2H), 4.64 (s, 2H), 4.39 (t, 2H), 4.17 (d, 2H), 4.08 (d, 2H), 3.88-3.82 (m, 2H), 3.70 (t, 2H), 2.23-2.21 (m, 2H), 2.10-2.07 (m, 2H). | 503 |
| 15 | 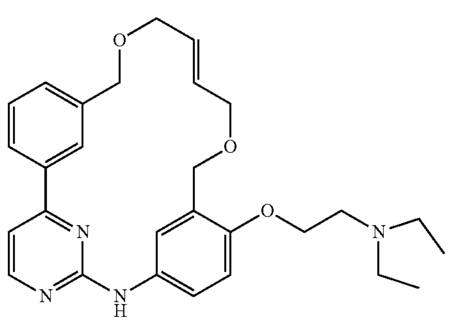 [SMILES: CCN(CC)CCOc1ccc2cc1COC/C=C/COCc1cccc(c1)-c1ccnc(n1)N2] | (MeOD-d₄): δ 8.49 (s, 1H), 7.98-7.97 (m, 1H), 7.77 (s, 1H), 7.63-7.61 (m, 1H), 7.57-7.55 (m, 1H), 7.42-7.38 (m, 4H), 7.14-7.11 (m, 1H), 5.83-5.76 (m, 1H, =CH), 5.42-5.34 (m, 1H, =CH), 4.29-4.27 (m, 1H, CH2), 4.13-4.10 (m, 2H), 3.83-3.72 (m, 2H), 3.24 (s, 2H), 3.25-2.97 (m, 4H), 2.29-2.24 (m, 2H), 2.11-1.92 (m, 4H) | 475 |
| 16 | 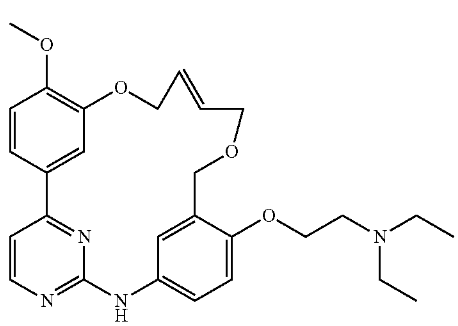 [SMILES: CCN(CC)CCOc1ccc2cc1COC/C=C/COc1cc(ccc1OC)-c1ccnc(n1)N2] | Mixture of cis and trans | 491 |

TABLE 1-continued

| No | Structure | ¹H NMR (400 MHz) | m/z [MH]⁺ |
|---|---|---|---|
| 17 | 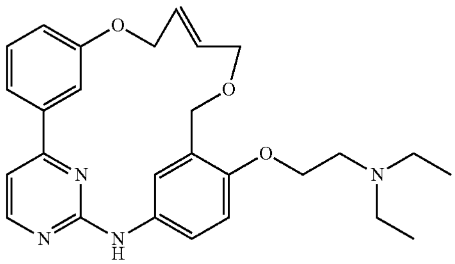 [SMILES: CCN(CC)CCOc1ccc2cc1COC/C=C/COc1cccc(c1)-c1ccnc(n1)N2] | Mixture of cis and trans | 461 |
| 18 | 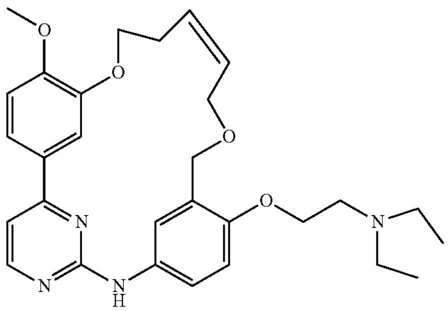 [SMILES: CCN(CC)CCOc1ccc2cc1COC/C=C\CCOc1cc(ccc1OC)-c1ccnc(n1)N2] | (CDCl₃) δ 12.11 (s, 1H), 8.21 (d, 1H), 8.09 (d, 1H), 7.88 (d, 1H), 7.57 (dd, 1H), 7.31-7.28 (m, 1H), 7.24-7.17 (m, 1H), 6.99 (d, 1H), 6.88 (d,), 5.94 (dt, 1H, CH, J = 7.6 Hz, J = 10.8 Hz), 5.82 (dt, J = 6.7 Hz, J = 10.8 Hz 1H), 4.51 (s, 2H), 4.42 (br s, 2H), 4.23-4.09 (m, 4H), 3.98 (s, 3H), 3.61 (br s, 2H), 3.36 (t, 4H), 2.70-2.60 (m, 2H), 1.41 (t, 6H). | 505 |
| 19 | 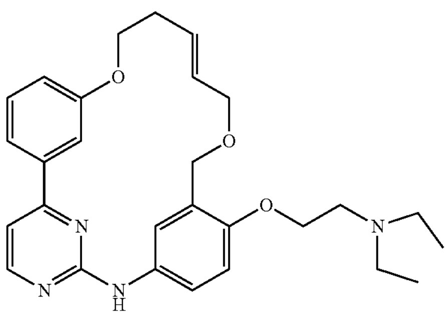 [SMILES: CCN(CC)CCOc1ccc2cc1COC/C=C/CCOc1cccc(c1)-c1ccnc(n1)N2] | (CDCl₃) δ 12.01 (s, 1H), 8.58 (d, 1H), 8.28-8.15 (m, 1H), 7.96-7.84 (m, 1H), 7.52-7.44 (m, 2H), 7.31-7.27 (m, 1H), 7.25-7.24 (m, 1H), 7.21-7.18 (m, 1H), 6.88-6.85 (m, 1H), 5.81 (dt, 1H, J = 6.0 Hz, J$_{trans}$ = 15.4 Hz), 5.69 (dt, 1H, J = 6.6 Hz, J$_{trans}$ = 15.4 Hz), 4.99 (s, 2H), 4.39 (brs, 2H), 4.31-4.25 (m, 2H), 4.07-4.00 (m, 2H), 3.60 (br s, 2H), 3.37-3.34 (m, 4H), 2.61-2.44 (m, 2H), 1.41 (t, 6H). | 475 |
| 20 | 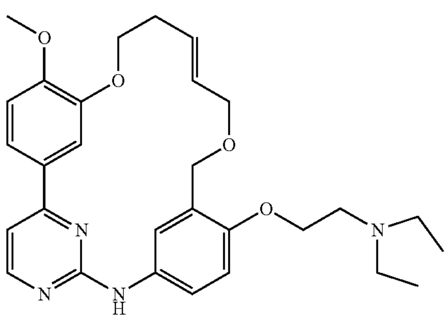 [SMILES: CCN(CC)CCOc1ccc2cc1COC/C=C/CCOc1cc(ccc1OC)-c1ccnc(n1)N2] | (CDCl₃) δ 12.01 (s, 1H), 8.29 (d, 1H), 8.08 (d, 1H), 7.96 (d, 1H), 7.66 (dd, 1H), 7.31-7.27 (m, 1H), 7.23-7.21 (m, 1H), 7.02 (d, 1H), 6.87 (d, 1H), 5.93 (dt, 1H, CH, J = 6.3 Hz, J$_{trans}$ = 15.6 Hz), 5.73 (dt, 1H, CH, J = 5.6 Hz, J$_{trans}$ = 15.6 Hz), 4.55 (s, 2H), 4.37 (br s, 2H), 4.30-4.25 (m, 2H), 4.08 (d, 2H), 3.97 (s, 3H), 3.60 (br s, 2H), 3.37-3.26 (m, 4H), 2.46-2.42 (m, 2H), 1.41 (t, 6H). | 505 |
| 21 | 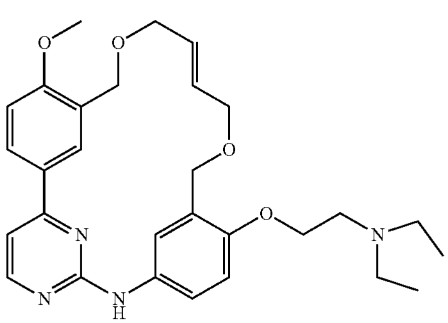 [SMILES: CCN(CC)CCOc1ccc2cc1COC/C=C/COCc1cc(ccc1OC)-c1ccnc(n1)N2] | (DMSO-d₆) δ 9.53 (s, 1H), 9.41 (s, 1H), 8.49 (d, 1H), 8.47 (d, 1H), 8.17 (d, 1H), 8.07 (dd, 1H), 7.36 (d, 1H), 7.17 (dd, 1H), 7.03 (d, 1H), 5.77-5.83 (m, 1H, =CH, J$_{trans}$ = 14.4 Hz), 5.51-5.59 (m, 1H, =CH, J$_{trans}$ = 14.4 Hz), 4.52 (d, 4H), 4.30 (t, 2H), 4.08 (d, 4H), 4.03 (d, 2H), 3.89 (s, 3H), 3.57 (q, 2H), 3.24-3.35 (m, 4H), 2.08 (s, 2H), 1.28 (t, 6H). | 506 |

TABLE 1-continued

| No | Structure | $^1$H NMR (400 MHz) | m/z [MH]$^+$ |
|---|---|---|---|
| 22 | 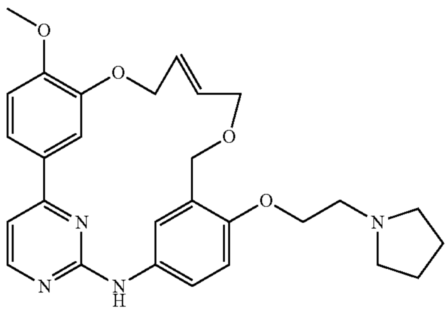 [SMILES: COc1ccc2cc1OC/C=C/COCc1cc(ccc1OCCN1CCCC1)Nc1nccc-2n1] | (CDCl$_3$) δ 11.92 (s, 1H), 8.15 (d, 1H), 8.10 (br s, 1H), 7.26 (d, 1H), 7.52 (dd, 1H), 7.31-7.29 (m, 1H), 7.18 (d, 1H), 6.99 (d, 1H), 6.89 (d, 1H), 6.08 (dt, 1H, CH, J = 5.6 Hz, J$_{trans}$ = 15.7 Hz), 5.83-5.74 (m, 1H, CH), 4.7 (d, 2H), 4.58 (s, 2H), 4.41 (s, 2H), 4.09 (d, 2H), 3.98 (s, 3H), 3.60 (s, 2H), 3.23-2.85 (m, 3H), 2.13 (br s, 5H). | 489 |
| 23 | 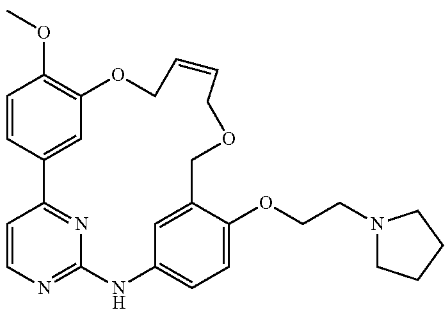 [SMILES: COc1ccc2cc1OC/C=C\COCc1cc(ccc1OCCN1CCCC1)Nc1nccc-2n1] | (CDCl$_3$) δ 8.20 (br s, 1H), 8.04 (dd, 2H), 7.64 (dd, 1H), 7.27-7.25 (m, 1H), 7.02-6.99 (m, 1H), 6.96-6.92 (m, 1H), 7.31-7.29 (m, 1H), 5.99 (dt, 1H, CH, J = 5.3 Hz, J$_{ciss}$ = 11.1 Hz), 5.79 (dt, 1H, CH, J = 4.7 Hz, J$_{ciss}$ = 11.2 Hz), 5.83-5.74 (m, 1H, CH), 4.92 (d, 2H), 4.54 (s, 2H), 4.44-4.42 (m, 2H), 4.19 (d, 2H), 3.99 (s, 3H), 3.62-3.60 (m, 2H), 3.43-3.37 (m, 1H), 2.13 (br s, 5H). | 489 |
| 24 | 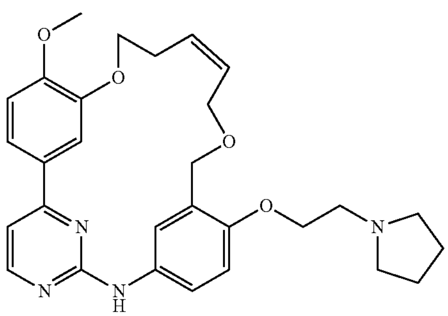 [SMILES: COc1ccc2cc1OCC/C=C\COCc1cc(ccc1OCCN1CCCC1)Nc1nccc-2n1] | (CDCl$_3$) δ 11.95 (s, 1H), 8.22 (d, 1H), 8.14 (d, 1H), 7.91 (d, 1H, 7.60 (dd, 1H), 7.35-7.32 (m, 1H), 7.27 (d, 1H), 7.03 (d, 1H), 6.90 (d, 1H), 5.94 (dt, 1H, J = 7.7 Hz, J$_{cis}$ = 10.8 Hz), 5.86 (dt, 1H, CH, J = 6.9 Hz, J$_{cis}$ = 10.8 Hz), 4.55 (s, 2H), 4.45 (br s, 2H), 4.26-4.13 (m, 4H), 4.01 (s, 3H), 3.65 (br s, 2H), 3.09-2.91 (m, 3H), 2.72-2.62 (m, 2H), 2.21-2.06 (br s, 5H). | 503 |
| 25 | 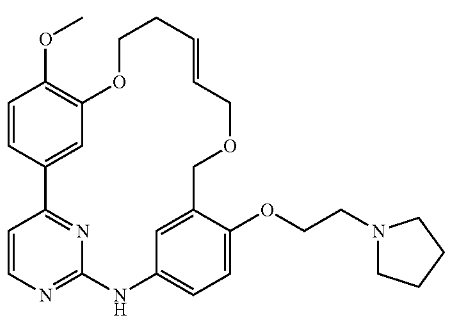 [SMILES: COc1ccc2cc1OCC/C=C/COCc1cc(ccc1OCCN1CCCC1)Nc1nccc-2n1] | (CDCl$_3$) δ 8.31 (d, 1H), 8.18 (d, 1H), 7.97 (d, 1H), 7.69 (dd, 1H), 7.26 (d, 1H), 7.03 (d, 1H), 6.91 (d, 1H), 5.95 (dt, 1H, CH, J = 6.3 Hz, J$_{trans}$ = 15.6 Hz), 5.73 (dt, 1H, CH, J = 5.3 Hz, J$_{trans}$ = 15.6 Hz), 4.58 (s, 2H), 4.42-4.37 (m, 2H), 4.29 (t, 2H), 3.65 (br s, 2H), 4.09 (d, 2H), 3.97 (s, 3H), 3.62-3.57 (m, 2H), 2.45-2.38 (m, 3H), 2.14 (br s, 5H). | 503 |
| 26 | 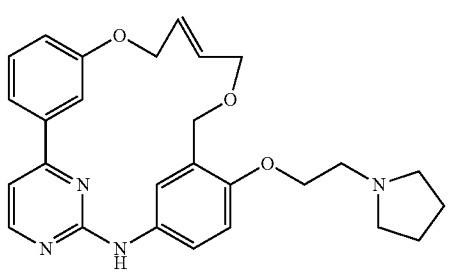 [SMILES: C1=C/COc2cccc(c2)-c2ccnc(n2)Nc2ccc(OCCN3CCCC3)c(c2)COC/1] | (CDCl$_3$) δ 8.24-8.14 (m, 1H), 8.00-7.94 (m, 1H), 7.61-7.92 (m, 1H), 7.41-7.37 (m, 1H), 7.33-7.31 (m, 1H), 7.24-7.15 (m, 2H), 6.88 (dd, 1H), 6.06 (dt, 1H, CH, J = 5.3 Hz, J$_{trans}$ = 15.8 Hz), 5.90-5.71 (m, 1H), 4.84 (d, 1H), 4.65 (d, 1H), 4.54 (s, 1H), 4.49 (s, 1H), 4.40-4.33, (m, 2H), 4.15 (d, 1H), 4.06 (dd, 1H), 3.88 (br s, 2H), 3.57 (br s, 2H), 3.41-3.37 (m, 2H), 2.13 (br s, 4H). | 459 |

TABLE 1-continued

| No | Structure | $^1$H NMR (400 MHz) | m/z [MH]$^+$ |
|---|---|---|---|
| 27 | 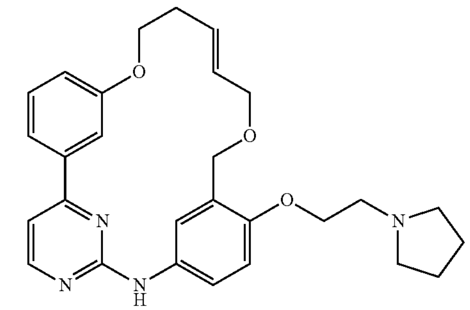 [SMILES: C1=C/COCc2cc(ccc2OCCN2CCCC2)Nc2nccc(n2)-c2cccc(c2)OCC/1] | (CDCl$_3$) δ 8.67 (d, 1H), 8.30 (d, 1H), 8.01-7.88 (m, 1H), 7.56-7.40 (m, 2H), 7.26-7.24 (m, 1H), 7.20-7.16 (m, 2H), 6.95-6.83 (m, 1H), 5.82 (dt, 1H, CH, J = 6.0 Hz, J$_{trans}$ = 15.5 Hz), 5.76-5.67 (m, 1H), 4.58-4.53 (m, 2H), 4.40-4.39 (m, 2H), 4.30-4.21 (m, 2H), 4.08-4.01 (m, 2H), 3.91 (br s, 2H), 3.61-3.60, (m, 2H), 3.39-3.34 (m, 2H), 2.63-2.49 (m, 2H), 2.13 (br s, 4H). | 473 |
| 28 | 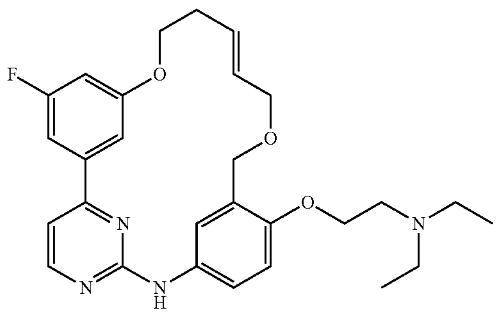 [SMILES: CCN(CC)CCOc1ccc2cc1COC/C=C/CCOc1cc(F)cc(c1)-c1ccnc(n1)N2] | (DMSO-d$_6$) δ 9.67 (s, 1H), 8.69 (d, 1H), 8.56 (d, 1H), 7.64 (s, 1H), 7.47 (d, 1H), 7.39 (d, 1H), 7.17-7.21 (m, 2H), 7.01 (d, 1H), 5.73-5.85 (m, 1H, =CH, J$_{trans}$ = 15.3 Hz), 5.57-5.64 (m, 1H, =CH, J$_{trans}$ = 15.3 Hz), 4.45 (s, 2H), 4.26-4.31 (m, 4H), 4.0 (d, 2H), 3.53-3.57 (m, 2H), 3.28-3.31 (m, 4H), 2.43-2.45 (m, 2H), 1.28 (t, 6H). | 493 |
| 29 | 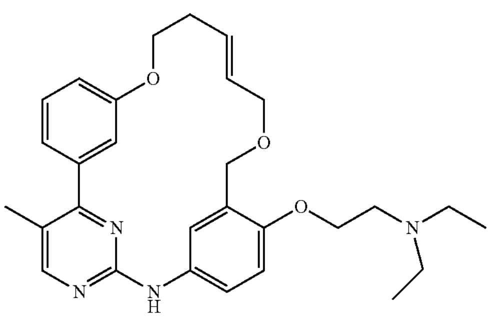 [SMILES: CCN(CC)CCOc1ccc2cc1COC/C=C/CCOc1cccc(c1)-c1nc(ncc1C)N2] | (DMSO-d$_6$) δ 9.83 (s, 1H), 9.64 (s, 1H), 8.75 (d, 1H), 8.44 (s, 1H), 7.52 (t, 1H), 7.45 (t, 1H), 7.28-7.33 (m, 2H), 7.18 (dd, 1H), 7.12 (d, 1H), 6.13-6.20 (m, 1H, =CH, J$_{trans}$ = 15.3 Hz), 5.73-5.81 (m, 1H, =CH, J$_{trans}$ = 15.3 Hz), 4.21-4.31 (m, 4H), 3.80-3.99 (m, 6H), 3.25-3.29 (m, 4H), 2.59-2.61 (m, 2H), 2.34 (s, 3H), 1.28 (t, 6H). | 489 |
| 30 | 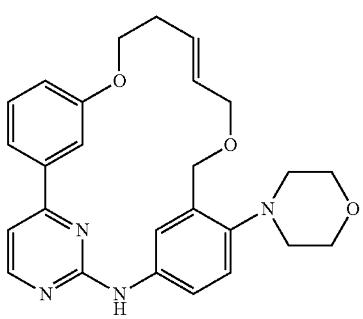 [SMILES: C1=C/COCc2cc(ccc2N2CCOCC2)Nc2nccc(n2)-c2cccc(c2)OCC/1] | (CDCl$_3$) δ 11.97 (s, 1H), 8.69 (d, 1H), 8.24 (d, 1H), 7.95 (br s, 1H), 7.54-7.45 (m, 2H), 7.35-7.32 (m, 2H), 7.22-7.15 (m, 2H), 5.83 (dt, 1H, CH, J = 6.0 Hz, J$_{trans}$ = 15.4 Hz), 5.69 (dt, 1H, CH, J = 6.7 Hz J$_{trans}$ = 15.4 Hz), 4.72 (s, 2H), 4.25-4.20 (m, 2H), 4.14 (d, 2H), 4.01-3.99 (m, 4H), 3.26-3.22 (m, 4H), 2.56-2.52 (m, 2H). | 445 |
| 31 | 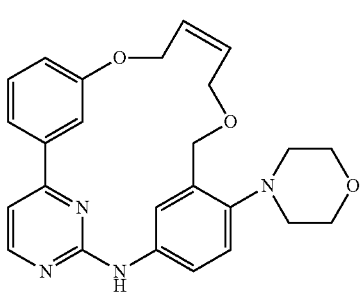 [SMILES: C1=C\COc2cccc(c2)-c2ccnc(n2)Nc2ccc(N3CCOCC3)c(c2)COC/1] | (CDCl$_3$) δ 11.47 (s, 1H), 8.24 (d, 1H), 8.18 (d, 1H), 8.09 (br t, 1H), 7.55 (d, 1H), 7.42 (t, 1H) 7.32-7.31 (m, 1H), 7.22-7.19 (m, 1H), 7.12 (d, 1H), 5.89 (dt, 1H, CH, J = 5.2 Hz, J$_{cis}$ = 11.4 Hz), 5.73 (dt, 1H, CH, J = 4.4 Hz, J$_{cis}$ = 11.4 Hz), 5.02-5.01 (m, 2H), 4.62 (s, 2H), 4.21-4.20 (m, 2H), 3.87-3.85 (m, 4H), 3.00-2.98 (m, 4H). | 431 |

TABLE 1-continued
| No | Structure | ¹H NMR (400 MHz) | m/z [MH]⁺ |
|---|---|---|---|
| 32 | 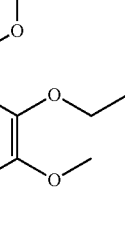 | (CDCl₃) δ 8.33-8.28 (m, 2H), 8.10 (d, 1H), 7.93 (d, 1H), 7.79 (d, 1H), 7.63 (t, 1H), 7.40 (d, 1H), 6.93 (d, 1H), 5.94-5.82 (m, 2H), 4.68 (s, 1H), 4.60 (s, 2H), 4.36 (m, 2H), 4.18 (d, 2H), 4.11 (d, 2H), 4.12-4.03 (m, 2H), 3.94 (s, 3H), 3.63 (m, 2H), 3.19 (m, 2H), 2.34-2.22 (m, 4H) | 502 |
| 33 | 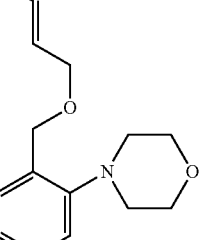 | (CDCl₃) δ 11.56 (s, 1H), 8.45 (d, 1H), 8.29-8.27 (m, 1H), 8.22 (d, 1H), 7.90 (d, 1H), 7.76 (d, 1H), 7.59 (t, 1H), 7.31 (d, 1H), 7.26-7.21 (m, 1H), 7.10 (d, 1H), 5.91-5.69 (m, 2H, 2xC=CH), 4.66 (s, 2H), 4.64 (s, 2H), 4.17-4.15 (m, 2H), 4.06-4.04 (m, 2H), 3.89-3.82 (m, 4H), 2.30-2.96 (m, 4H) | 445 |
| 348 | 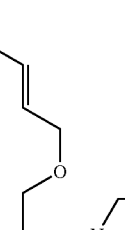 | (CDCl₃) δ 11.69 (s, 1H), 8.31 (d, 1H), 8.28 (d, 1H), 8.09 (d, 1H), 8.31 (dd, 1H), 7.25-7.21 (m, 2H), 7.09 (d, 1H), 6.99 (d, 1H), 5.98-5.85 (m, 2H, 2xC=CH), 4.67 (s, 2H), 4.61 (s, 2H), 4.19 (d, 2H), 4.10 (d, 2H), 3.98 (s, 3H), 3.93-3.86 (m, 4H), 2.95 (t, 2H) | 475 |
| 35 | 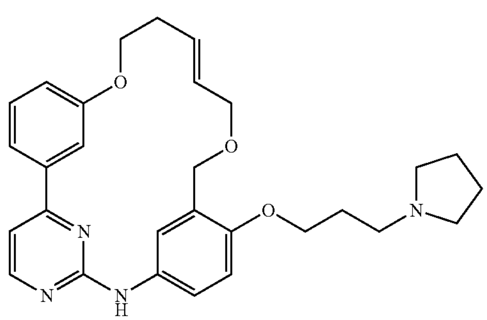 | (MeOD-d₄) δ 8.69 (d, 1H), 8.33 (d, 1H), 7.85 (d, 1H), 7.45 (d, 1H), 7.22 (m, 2H), 6.89-6.99 (m, 3H), 5.60-5.85 (m, 2H), 4.49 (m, 2H), 4.09 (m, 4H), 3.92 (m, 2H), 3.60 (m, 2H), 3.40 (m, 2H), 3.15 (m, 2H), 2.39 (m, 2H), 2.14 (m, 4H), 1.83 (m, 2H). | 487 |
| 36 | 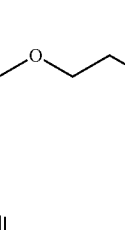 | (DMSO-d₆) δ 9.68 (s, 1H), 8.70 (d, 1H), 8.56 (d, 1H), 7.65 (s, 1H), 7.47 (d, 1H), 7.50 (d, 1H), 7.17-7.22 (m, 2H), 7.03 (d, 1H), 5.75-5.83 (m, 1H, =CH, J$_{trans}$ = 15.4 Hz), 5.56-5.65 (m, 1H, =CH, J$_{trans}$ = 15.4 Hz), 4.46 (s, 2H), 4.27 (t, 4H), 4.0 (d, 2H), 3.56-3.69 (m, 6H), 23.15-3.21 (m, 2H), 2.03-2.09 (m, 2H), 1.89-1.95 (m, 2H). | 491 |

TABLE 1-continued

| No | Structure | ¹H NMR (400 MHz) | m/z [MH]⁺ |
|---|---|---|---|
| 37 | 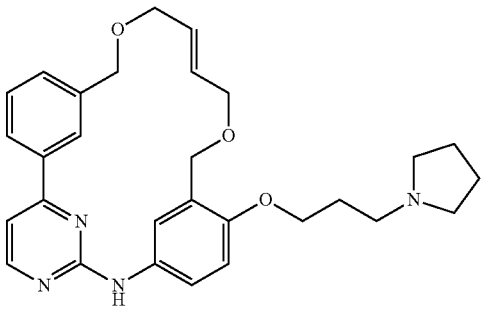 [SMILES: C1=C/COCc2cc(ccc2OCCCN2CCCC2)Nc2nccc(n2)-c2cccc(c2)OCC/1] | (CDCl₃) δ 8.39 (m, 1H), 8.26 (m, 2H), 7.90 (m, 1H), 7.76 (m, 1H), 7.61 (m, 1H), 7.26-7.34 (m, 2H), 6.89 (m, 1H), 5.60-5.95 (m, 2H), 4.65 (m, 2H), 4.61 (m, 2H), 4.15 (m, 2H), 4.09 (m, 4H), 3.90 (m, 2H), 3.35 (m, 2H), 3.05 (m, 2H), 2.34 (m, 2H), 2.10 (m, 4H). | 487 |
| 38 | 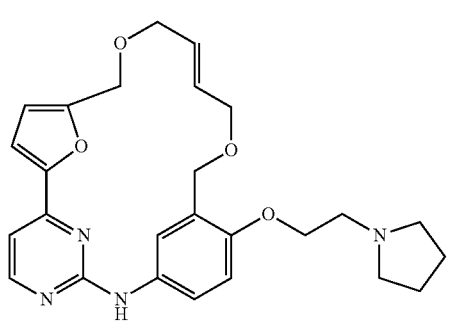 | (MeOD-d₄) δ 8.90 (d, 1H), 8.33 (d, 1H), 7.37 (d, 1H), 7.17 (d, 1H), 7.14-7.11 (m, 1H), 7.04 (d, 1H), 6.67 (d, 1H), 6.04 (dt, 1H, CH, J = 5.2 Hz, J$_{trans}$ = 15.8 Hz), 5.96 (dt, 1H, CH, J = 5.0 Hz, J$_{trans}$ = 15.8 Hz), 4.65 (s, 2H), 4.62 (s, 2H), 4.37 (t, 2H), 4.14 (d, 2H), 4.09 (d, 2H), 3.81 (br s, 2H) 3.66 (t, 2H), 3.33 (s, 2H), 2.21-1.98 (m, 4H). | 463 |
| 39 | 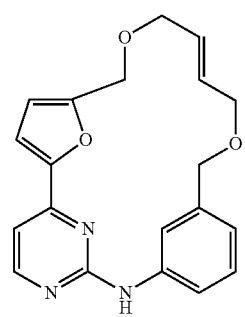 [SMILES: C1=C2COC/C=C/COCc3cccc(c3)Nc3nccc(n3)C(=C1)O2] | (CDCl₃): δ 10.91(s, 1H), 8.67-8.66 (m, 1H), 8.17-8.14 (m, 1H), 7.37-7.32 (m, 1H), 7.28-7.27 (m, 1H), 7.18-7.16 (m, 2H), 6.97 (d, 1H), 6.65 (d, 1H), 6.00 (dt, 1H, CH, J = 5.6 Hz, J$_{trans}$ = 15.8 Hz), 5.89 (dt, 1H, CH, J = 5.5 Hz, J$_{trans}$ = 15.8 Hz), 4.61 (s, 2H), 4.58 (s, 2H), 4.15 (d, 2H), 4.08 (d, 2H). | 350 |
| 40 | 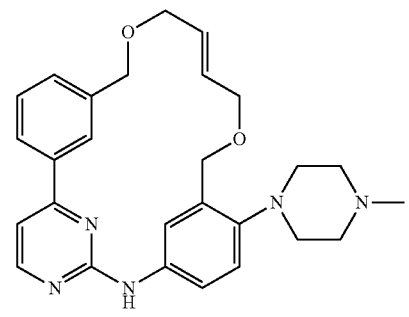 | (CDCl₃) δ 10.62 (s, 1H), 8.59 (d, 1H), 8.29-8.24 (m, 2H), 7.88 (d, 1H), 7.72 (d, 1H), 7.59-7.56 (m, 1H), 7.30 (d, 1H), 7.18-7.10 (m, 2H), 5.90-5.69 (m, 2H), 4.65 (s, 2H), 4.61 (s, 2H), 4.17-4.15 (m, 2H), 4.08-4.06 (m, 2H), 3.68-3.66 (m, 2H), 3.37-3.25 (m, 4H), 2.93-2.91 (m, 2H), 2.90 (s, 3H) | 458 |
| 41 | 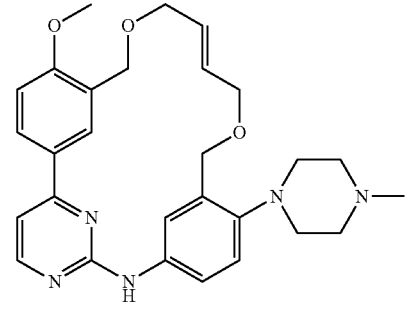 [SMILES: COc1ccc2cc1COC/C=C/COCc1cc(ccc1N1CCN(C)CC1)Nc1nccc-2n1] | (CDCl₃) δ 11.83 (s, 1H), 8.35 (d, 1H), 8.26 (d, 1H), 8.10 (d, 1H), 7.93 (dd, 1H), 7.31-7.23 (m, 2H), 7.13 (d, 1H), 7.03 (d, 1H), 5.96-5.86 (m, 2H), 4.61 (s, 4H), 4.17-4.15 (m, 2H), 4.11-4.10 (m, 2H), 3.98 (s, 3H), 3.68-3.66 (m, 2H), 3.35-3.32 (m, 2H), 3.22-3.08 (m, 2H), 3.08-3.06 (m, 2H), 2.90 (s, 3H) | 488 |

TABLE 1-continued

| No | Structure | $^1$H NMR (400 MHz) | m/z [MH]$^+$ |
|---|---|---|---|
| 42 | 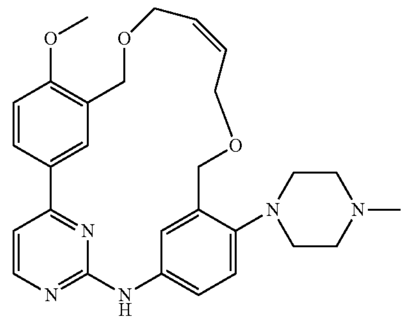 [SMILES: COc1ccc2cc1COC/C=C\COCc1cc(ccc1N1CCN(C)CC1)Nc1nccc-2n1] | (CDCl$_3$) δ 10.92 (s, 1H), 8.25 (d, 1H), 8.21 (d, 1H), 8.18-8.16 (m, 1H), 7.80 (dd, 1H), 7.18-7.11 (m, 3H), 6.95 (d, 1H), 5.72-5.64 (m, 2H), 4.54 (s, 2H), 4.50 (s, 2H), 4.26-4.25 (m, 2H), 4.18-4.17 (m, 2H), 3.90 (s, 3H), 3.61-3.59 (m, 2H), 3.33-3.26 (m, 4H), 3.22-3.08 (m, 2H), 3.05-3.01 (m, 2H), 2.85 (s, 3H) | 488 |
| 43 | 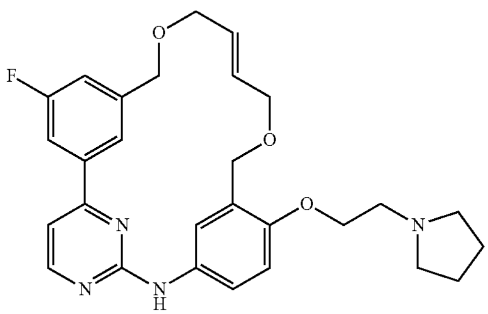 [SMILES: Fc1cc2cc(c1)-c1ccnc(n1)Nc1ccc(OCCN3CCCC3)c(c1)COC/C=C/COC2] | (MeOD-d$_4$) δ 8.72 (d, 1H), 8.48 (m, 1H), 8.11 (s, 1H), 7.72 (m, 1H), 7.34 (m, 2H), 7.05-7.15 (m, 2H), 5.82-5.90 (m, 2H), 4.65 (m, 2H), 4.39 (m, 2H), 4.16 (m, 2H), 4.09 (m, 2H), 3.80 (m, 2H), 3.71 (m, 2H), 3.27 (m, 4H), 2.08-2.24 (m, 4H). | 491 |
| 44 | 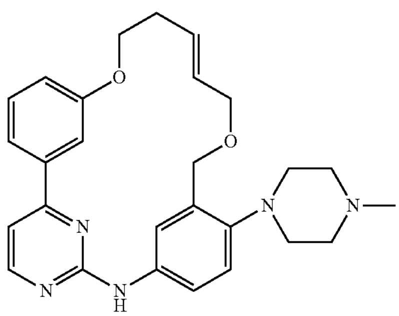 [SMILES: CN1CCN(c2ccc3cc2COC/C=C/CCOc2cccc(c2)-c2ccnc(n2)N3)CC1] | (MeOD-d$_4$): δ 8.95 (d, 1H), 8.45 (d, 1H), 7.95 (t, 1H), 7.56 (d, 1H), 7.46 (t, 1H), 7.33 (d, 1H), 7.21 (dd, 1H), 7.17-7.15 (m, 1H), 7.12-7.09 (m, 1H), 5.89 (dt, 1H, CH, J = 6.1 Hz, J$_{trans}$ = 15.5 Hz), 5.71 (dt, 1H, CH, J = 6.7 Hz, J$_{trans}$ = 15.5 Hz), 4.63 (s, 2H), 4.29 (t, 2H), 4.13 (d, 2H), 3.60-3.57 (m, 3H), 3.37-3.35 (m, 5H), 2.99 (s, 3H), 2.54-2.48 (m, 2H). | 458 |
| 45 | 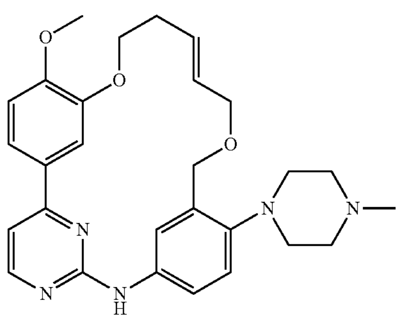 [SMILES: COc1ccc2cc1OCC/C=C/COCc1cc(ccc1N1CCN(C)CC1)Nc1nccc-2n1] | Mixture of cis and trans | 488 |
| 46 | 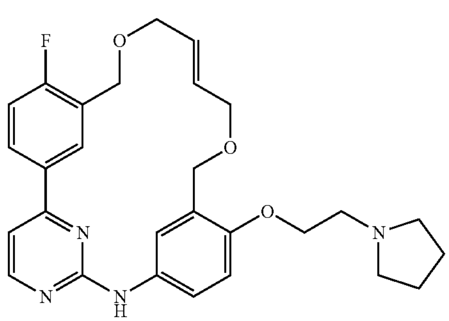 [SMILES: Fc1ccc2cc1COC/C=C/COCc1cc(ccc1OCCN1CCCC1)Nc1nccc-2n1] | (MeOD-d$_4$) δ 8.45 (m, 2H), 8.30 (m, 1H), 8.05 (m, 1H), 7.38 (m, 1H), 7.26 (m, 1H), 7.16 (m, 1H), 7.08 (m, 1H), 5.90-5.92 (m, 2H), 4.65 (m, 4H), 4.39 (m, 2H), 4.16 (m, 2H), 4.09 (m, 2H), 3.85 (m, 2H), 3.71 (m, 2H), 3.32 (m, 2H), 2.08-2.25 (m, 4H). | 491 |

TABLE 1-continued

| No | Structure | ¹H NMR (400 MHz) | m/z [MH]⁺ |
|---|---|---|---|
| 47 | 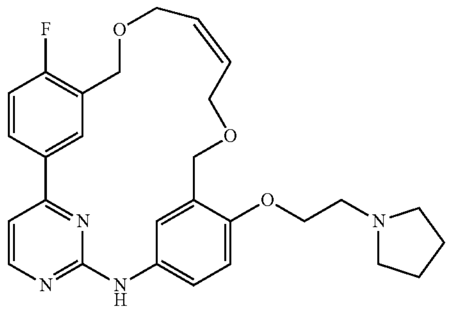 [SMILES: Fc1ccc2cc1COC/C=C\COCc1cc(ccc1OCCN1CCCC1)Nc1nccc-2n1] | (MeOD-d₄) δ 8.45 (m, 1H), 8.40 (m, 1H), 8.22 (m, 1H), 8.01 (m, 1H), 7.35 (m, 1H), 7.27 (m, 1H), 7.15 (m, 1H), 7.08 (m, 1H), 5.78 (m, 2H), 4.64 (m, 2H), 4.61 (m, 2H), 4.40 (m, 2H), 4.31 (m, 2H), 4.21 (m, 2H), 3.81 (m, 2H), 3.72 (m, 2H), 3.32 (m, 2H), 2.08-2.24 (m, 4H). | 491 |
| 48 | 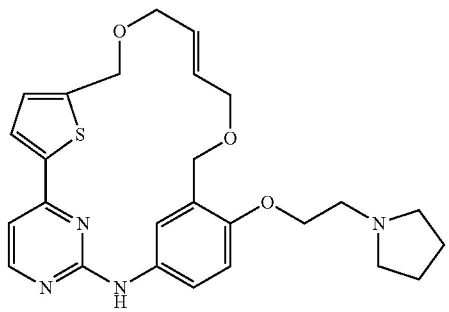 [SMILES: C1=C2COC/C=C/COCc3cc(ccc3OCCN3CCCC3)Nc3nccc(n3)C(=C1)S2] | (MeOD-d₄): δ 8.66 (d, 1H), 8.32 (d, 1H), 7.81 (d, 1H), 7.27 (d, 1H), 7.12 (dd, 1H), 7.07-7.02 (m, 2H), 6.08 (dt, 1H, CH, J = 4.4 Hz, J$_{trans}$ = 15.6 Hz), 5.98 (dt, 1H, CH, J = 4.6 Hz, J$_{trans}$ = 15.6 Hz), 4.61 (s, 2H), 4.38 (t, 2H), 4.18 (d, 4H), 3.81 (br s, 2H), 3.69 (t, 2H), 3.37-3.35 (m, 2H), 2.22-2.08 (m, 6H). | 479 |
| 49 | 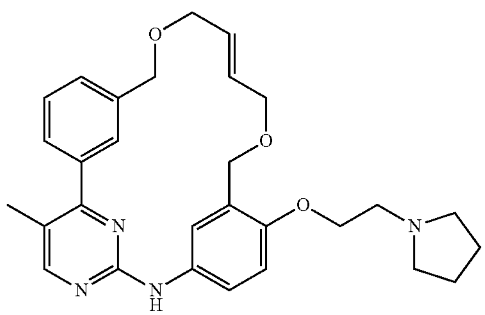 [SMILES: Cc1cnc2nc1-c1cccc(c1)COC/C=C/COCc1cc(ccc1OCCN1CCCC1)N2] | (CDCl₃): δ 10.4 (s, 1H), 8.40 (s, 1H), 8.12 (s, 1H), 7.78 (s, 1H), 7.65-7.36 (m, 3H), 7.07 (d, 1H), 6.78 (d, 1H), 5.84-5.64 (m, 2H), 4.56 (s, 2H), 4.42 (s, 2H), 4.31 (br s, 2H), 4.10 (d, 2H), 3.99 (d, 2H), 3.85 (m, 2H), 3.50 (m, 2H), 2.97 (m, 2H), 2.26 (s, 3H), 2.05 (m, 4H) | 487 |
| 50 | 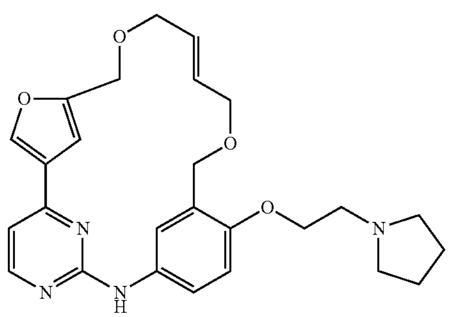 [SMILES: C1=C/COCc2cc(ccc2OCCN2CCCC2)Nc2nccc(n2)-c2coc(c2)COC/1] | (MeOD-d₄): δ 8.56 (d, 1H), 8.38 (d, 1H), 8.29 (br s, 1H), 7.17 (d, 1H), 7.11-7.06 (m, 2H), 7.03-7.01 (m, 1H), 5.99 (dt, 1H, CH, J = 6.0 Hz, J$_{trans}$ = 15.6 Hz), 5.84 (dt, 1H, CH, J = 5.8 Hz, J$_{trans}$ = 15.6 Hz), 4.66 (s, 2 H₂), 4.57 (s, 2H), 4.37 (t, 2H), 4.18 (d, 2H), 4.09 (d, 2H), 3.79 (br s, 2H), 3.69 (t, 2H), 3.35-3.34 (m, 2H), 2.21-2.07 (m, 4H). | 463 |
| 51 | 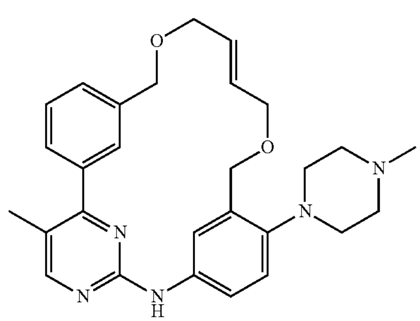 | (DMSO-d₆): δ 9.50 (s, 1H), 8.58-8.52 (m, 1H), 8.42-8.41 (m, 1H), 7.73-7.64 (m, 1H), 7.61-7.57 (m, 1H), 7.51-7.44 (m, 2H), 7.15-7.11 (m, 1H), 7.08-7.01 (m, 1H), 5.86-5.67 (m, 2H), 4.61-4.55 (m, 2H), 4.45-4.43 (m, 2H), 4.12-4.03 (m, 4H), 3.58-3.54 (m, 2H), 3.22-3.18 (m, 2H), 3.20 (s, 3H), 2.46-2.31 (m, 2H), 2.24 (s, 3H) | 472 |

TABLE 1-continued

| No | Structure | ¹H NMR (400 MHz) | m/z [MH]⁺ |
|---|---|---|---|
| 52 | 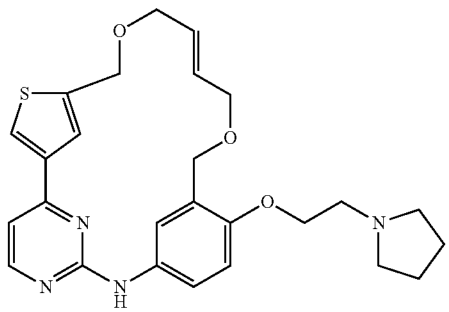 [SMILES: C1=C/COCc2cc(ccc2OCCN2CCCC2)Nc2nccc(n2)-c2csc(c2)COC/1] | (MeOD-d₄): δ 9.03 (d, 1H), 8.86 (d, 1H), 8.81 (d, 1H), 8.26 (s, 1H), 7.81 (d, 1H), 7.59 (dd, 1H), 7.56-7.51 (m, 1H), 6.38 (dt, 1H, CH, J = 5.7 Hz, J$_{trans}$ = 15.7 Hz), 6.31 (dt, 1H, CH, J = 5.4 Hz, J$_{trans}$ = 15.7 Hz), 5.24 (s, 2H), 5.14 (s, 2H), 4.86 (t, 2H), 4.65 (d, 2H), 4.54 (d, 2H), 4.29 (br s, 2H), 4.18 (t, 2H), 3.84-3.83 (m, 1H), 2.80-2.48 (m, 5H). | 479 |
| 53 | 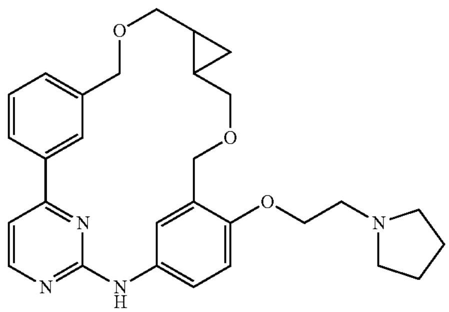 [SMILES: c1cc2cc(c1)-c1ccnc(n1)Nc1ccc(OCCN3CCCC3)c(c1)COCC1CC1COC2] | (CDCl₃) δ 8.78 (br s, 1H), 8.63 (br s, 1H), 8.42 (d, 1H), 7.79 (d, 1H), 7.50 (d, 1H), 7.42 (t, 1H), 7.18 (d, 1H), 6.83 (m, 2H), 5.12 (d, 1H), 4.87 (d, 1H), 4.72 (d, 1H), 4.61 (d, 1H), 4.14-4.19 (m, 2H), 4.03-4.07 (m, 2H), 2.99 (t, 2H), 2.81-2.86 (m, 1H), 2.74 (br s, 4H), 2.66-2.71 (m, 1H), 1.81-1.86 (m, 4H), 1.04-1.15 (m, 2H), 0.28-0.33 (m, 1H), 0.15-0.20 (m, 1H). | 487 |
| 54 | 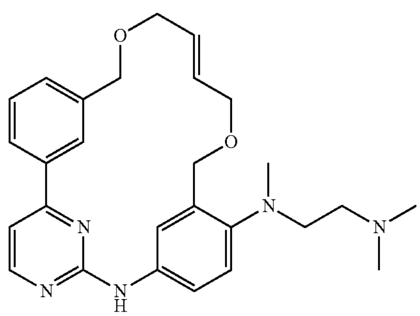 [SMILES: CN(C)CCN(C)c1ccc2cc1COC/C=C/COCc1cccc(c1)-c1ccnc(n1)N2] | (MeOD-d₄) δ 8.87 (s, 1H), 8.48 (s, 1H), 8.29 (s, 1H), 7.98 (d, 1H), 7.64 (d, 1H), 7.54 (d, 1H), 7.40 (d, 1H), 7.37 (d, 1H), 7.20 (dd, 1H), 6.00-5.78 (m, 2H, J$_{trans}$ = 15.6 Hz), 4.67 (s, 2H), 4.27 (d, 2H), 4.06 (d, 2H), 3.40 (t, 2H), 3.15 (t, 2H), 2.89 (s, 6H), 2.76 (s, 3H). | 460 |
| 55 | 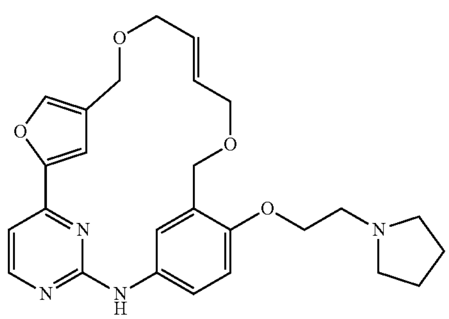 [SMILES: C1=C/COCc2cc(ccc2OCCN2CCCC2)Nc2nccc(n2)-c2cc(co2)COC/1] | (MeOD-d₄) δ 8.51 (bs, 1H), 8.34 (bd, 1H), 7.75 (s, 1H), 7.49 (s, 1H), 7.11-7.06 (m, 2H), 7.00 (d, 1H), 6.07 (dt, 1H, J$_{trans}$ = 15.6 Hz, J = 5.4 Hz), 5.92 (dt, 1H, J$_{trans}$ = 15.7 Hz, J = 5.0 Hz), 4.63 (s, 2H), 4.47 (s, 2H), 4.36 (t, 2H), 4.19 (d, 2H), 4.08 (d, 2H), 3.79 (bs, 2H), 3.69 (t, 2H), 3.27-3.25 (m, 2H), 2.21-2.08 (m, 4H). | 463 |
| 56 | 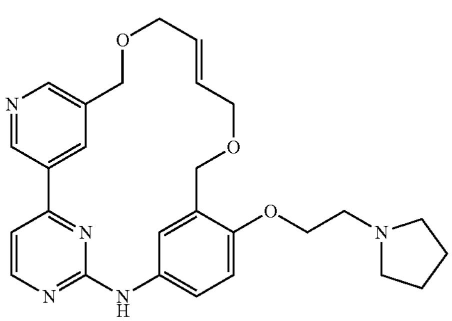 [SMILES: C1=C/COCc2cc(ccc2OCCN2CCCC2)Nc2nccc(n2)-c2cncc(c2)COC/1] | (MeOD-d₄) δ 9.26 (bs, 1H), 8.90-8.87 (m, 2H), 8.61-8.58 (m, 2H), 7.44 (d, 1H), 7.15-7.12 (m, 1H), 7.06 (d, 1H), 5.96 (dt, 1H, J$_{trans}$ = 15.7 Hz, J = 5.3 Hz), 5.88 (dt, 1H, J$_{trans}$ = 15.7 Hz, J = 5.6 Hz,), 4.77 (s, 2H), 4.64 (s, 2H), 4.38 (t, 2H), 4.15 (q, 4H), 3.81 (bs, 2H), 3.70 (t, 2H), 3.27-3.25 (m, 2H), 2.23-1.99 (m, 5H). | 474 |

TABLE 1-continued

| No | Structure | ¹H NMR (400 MHz) | m/z [MH]⁺ |
|---|---|---|---|
| 57 | 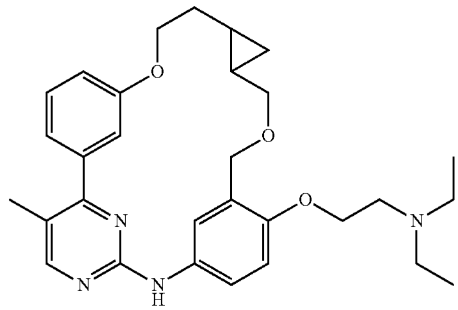 [SMILES: CCN(CC)CCOc1ccc2cc1COCC1CC1CCOc1cccc(c1)-c1nc(ncc1C)N2] | (CDCl₃) δ 8.27 (d, 1H), 8.07 (s, 1H), 7.49-7.48 (m, 1H), 7.38 (t, 1H), 7.24-7.21 (m, 2H), 7.11-7.08 (dd, 1H), 6.86 (d, 1H), 4.52 (q, 2H), 4.40-4.38 (br, m, 2H), 4.33-4.23 (m, 1H), 4.18-4.13 (m, 1H), 4.78 (dd, 1H), 3.56-3.53 (m, 2H), 3.33-3.28 (br, m, 4H), 3.03 (dd, 1H), 2.38 (s, 3H), 1.38 (t, 6H), 1.22-1.12 (m, 1H), 1.00-0.93 (m, 1H), 0.86-0.77 (m, 1H), 0.51-0.42 (m, 2H). | 503 |
| 58 | 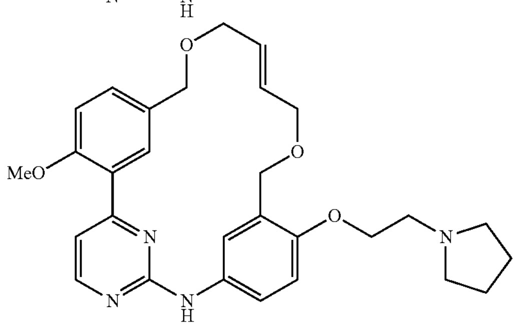 | (MeOD-d₄) δ 8.61 (d, 1H), 8.36 (d, 1H), 8.07 (s, 1H), 7.59 (d, 1H), 7.53 (dd, 1H), 7.19 (d, 1H), 7.13 (dd, 1H), 7.04 (d, 1H), 5.90 (dt, 1H, $J_{trans}$ = 15.6 Hz, J = 5.6 Hz), 5.79 (dt, 1H, $J_{trans}$ = 15.8 Hz, J = 5.9 Hz), 4.61 (s, 2H), 4.59 (s, 2H), 4.37 (t, 2H), 4.11 (d, 2H), 4.08 (d, 2H), 3.95 (s, 3H), 3.80 (m, 2H); 3.68 (t, 2H), 2.17 (m, 2H), 2.08 (m, 2H), 1.30 (m, 2H). | 503 |
| 59 | 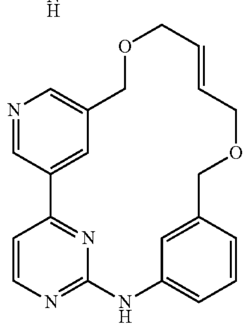 | (DMSO-d₆) δ 9.29 (s, 1H), 8.78 (s, 1H), 8.63 (d, 1H), 8.57 (s, 1H), 8.52 (s, 1H), 7.62 (d, 1H), 7.28 (t, 1H), 7.14 (d, 1H), 6.98 (d, 1H), 5.90-5.81 (m, 2H), 4.62 (s, 2H), 4.49 (s, 2H), 4.09-4.05 (m, 4H). | 361 |
| 60 | 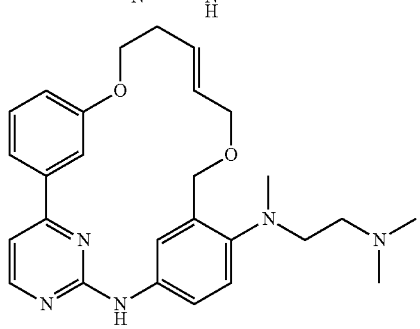 | (MeOD-d₄) δ 9.06 (s, 1H), 8.45 (d, 1H), 7.95 (s, 1H), 7.57-7.32 (m, 4H), 7.21-7.18 (m, 2H), 5.97 (dt, $J_{trans}$ = 15.4 Hz, J = 6.1 Hz), 5.77 (dt, $J_{trans}$ = 15.4 Hz, J = 6.1 Hz), 4.63 (s, 2H), 4.50-4.00 (m, 4H), 3.09 (t, 2H), 3.08 (s, 3H), 2.91 (s, 3H), 2.88 (s, 3H), 2.55-2.50 (m, 2H), 1.32-1.25 (m, 2H). | 460 |

As stated previously in one embodiment of the invention the compounds are of the formula (III):

Formula (III)

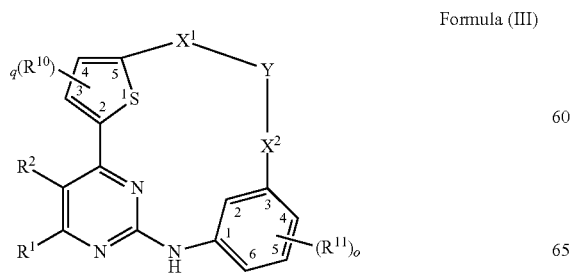

Following analogous procedures to the ones described above and by making appropriate modifications to the starting materials the compounds listed in Table 2 may also be made.

Following analogous procedures to the ones described above and by making appropriate modifications to the starting materials the compounds listed in Table 3 may also be made.

TABLE 2

| No | $R^1$ | $R^2$ | $X^1$ | $X^2$ | $Y^A$ | $R^{10B}$ | $R^{11B}$ |
|---|---|---|---|---|---|---|---|
| III-1 | H | H | —OCH$_2$CH$_2$— | —CH$_2$OCH$_2$— | —CH=CH— | H | H |
| III-2 | H | H | —OCH$_2$— | —CH$_2$OCH$_2$— | —CH=CH— | H | H |
| III-3 | H | H | —CH$_2$OCH$_2$— | —CH$_2$OCH$_2$— | —CH=CH— | —OCH$_3$ | H |
| III-4 | H | H | —OCH$_2$CH$_2$— | —CH$_2$OCH$_2$— | —CH=CH— | H | —OCH$_3$ |
| III-5 | H | H | —OCH$_2$— | —CH$_2$OCH$_2$— | —CH=CH— | H | —OCH$_3$ |
| III-6 | H | H | —OCH$_2$— | —CH$_2$OCH$_2$— | —CH=CH— | —OCH$_3$ | H |
| III-7 | H | H | —OCH$_2$CH$_2$— | —CH$_2$CH$_2$O— | —CH=CH— | H | H |
| III-8 | H | H | —OCH$_2$CH$_2$— | —CH$_2$O— | —CH=CH— | H | H |
| III-9 | H | H | —CH$_2$OCH$_2$— | —CH$_2$OCH$_2$— | —CH=CH— | —OCH$_3$ | —OCH$_2$CH$_2$-pyrollidin-1-yl |
| III-10 | H | H | —CH$_2$OCH$_2$— | —CH$_2$OCH$_2$— | —CH=CH— | H | —OCH$_2$CH$_2$—N(Et)$_2$ |
| III-11 | H | H | —OCH$_2$— | —CH$_2$OCH$_2$— | —CH=CH— | —OCH$_3$ | —OCH$_2$CH$_2$—N(Et)$_2$ |
| III-12 | H | H | —OCH$_2$— | —CH$_2$OCH$_2$— | —CH=CH— | H | —OCH$_2$CH$_2$—N(Et)$_2$ |
| III-13 | H | H | —OCH$_2$— | —CH$_2$OCH$_2$— | —CH=CH— | —OCH$_3$ | —OCH$_2$CH$_2$—N(Et)$_2$ |
| III-14 | H | H | —OCH$_2$CH$_2$— | —CH$_2$OCH$_2$— | —CH=CH— | H | —OCH$_2$CH$_2$—N(Et)$_2$ |
| III-15 | H | H | —OCH$_2$CH$_2$— | —CH$_2$OCH$_2$— | —CH=CH— | —OCH$_3$ | —OCH$_2$CH$_2$—N(Et)$_2$ |
| III-16 | H | H | —CH$_2$OCH$_2$— | —CH$_2$OCH$_2$— | —CH=CH— | —OCH$_3$ | —OCH$_2$CH$_2$—N(Et)$_2$ |
| III-17 | H | H | —OCH$_2$— | —CH$_2$OCH$_2$— | —CH=CH— | —OCH$_3$ | —OCH$_2$CH$_2$-pyrollidin-1-yl |
| III-18 | H | H | —OCH$_2$CH$_2$— | —CH$_2$OCH$_2$— | —CH=CH— | —OCH$_3$ | —OCH$_2$CH$_2$-pyrollidin-1-yl |
| III-19 | H | H | —OCH$_2$— | —CH$_2$OCH$_2$— | —CH=CH— | H | —OCH$_2$CH$_2$-pyrollidin-1-yl |
| III-20 | H | H | —OCH$_2$CH$_2$— | —CH$_2$OCH$_2$— | —CH=CH— | H | —OCH$_2$CH$_2$-pyrollidin-1-yl |
| III-21 | H | H | —OCH$_2$CH$_2$— | —CH$_2$OCH$_2$— | —CH=CH— | F | —OCH$_2$CH$_2$—N(Et)$_2$ |
| III-22 | H | CH$_3$ | —OCH$_2$CH$_2$— | —CH$_2$OCH$_2$— | —CH=CH— | H | —OCH$_2$CH$_2$—N(Et)$_2$ |
| III-23 | H | H | —OCH$_2$CH$_2$— | —CH$_2$OCH$_2$— | —CH=CH— | H | morpholin-4-yl |
| III-24 | H | H | —OCH$_2$— | —CH$_2$OCH$_2$— | —CH=CH— | H | morpholin-4-yl |
| III-25 | H | H | —CH$_2$OCH$_2$— | —CH$_2$OCH$_2$— | —CH=CH— | H | morpholin-4-yl |
| III-26 | H | H | —CH$_2$OCH$_2$— | —CH$_2$OCH$_2$— | —CH=CH— | —OCH$_3$ | morpholin-4-yl |
| III-27 | H | H | —OCH$_2$CH$_2$— | —CH$_2$OCH$_2$— | —CH=CH— | H | —OCH$_2$CH$_2$CH$_2$—N(Et)$_2$ |
| III-28 | H | H | —OCH$_2$CH$_2$— | —CH$_2$OCH$_2$— | —CH=CH— | F | —OCH$_2$CH$_2$-pyrollidin-1-yl |
| III-29 | H | H | —CH$_2$OCH$_2$— | —CH$_2$OCH$_2$— | —CH=CH— | H | —OCH$_2$CH$_2$CH$_2$-pyrollidin-1-yl |
| III-30 | H | H | —CH$_2$OCH$_2$— | —CH$_2$OCH$_2$— | —CH=CH— | H | 4-methy-piperazin-1-yl |
| III-31 | H | H | —CH$_2$OCH$_2$— | —CH$_2$OCH$_2$— | —CH=CH— | —OCH$_3$ | 4-methy-piperazin-1-yl |
| III-32 | H | H | —CH$_2$OCH$_2$— | —CH$_2$OCH$_2$— | —CH=CH— | F | —OCH$_2$CH$_2$CH$_2$-pyrollidin-1-yl |
| III-33 | H | H | —OCH$_2$CH$_2$— | —CH$_2$OCH$_2$— | —CH=CH— | H | 4-methy-piperazin-1-yl |
| III-34 | H | H | —OCH$_2$CH$_2$— | —CH$_2$OCH$_2$— | —CH=CH— | —OCH$_3$ | 4-methy-piperazin-1-yl |
| III-35 | H | H | —CH$_2$OCH$_2$— | —CH$_2$OCH$_2$— | —CH=CH— | F | —OCH$_2$CH$_2$-pyrollidin-1-yl |
| III-36 | H | CH$_3$ | —CH$_2$OCH$_2$— | —CH$_2$OCH$_2$— | —CH=CH— | H | —OCH$_2$CH$_2$-pyrollidin-1-yl |
| III-37 | H | CH$_3$ | —CH$_2$OCH$_2$— | —CH$_2$OCH$_2$— | —CH=CH— | H | —OCH$_2$CH$_2$CH$_2$-pyrollidin-1-yl |
| III-38 | H | H | —CH$_2$OCH$_2$— | —CH$_2$OCH$_2$— | —CH=CH— | H | —N(CH$_3$)CH$_2$CH$_2$Et$_2$ |
| III-39 | H | H | —CH$_2$OCH$_2$— | —CH$_2$OCH$_2$— | —CH=CH— | —OCH$_3$ | —OCH$_2$CH$_2$-pyrollidin-1-yl |
| III-40 | H | H | —OCH$_2$CH$_2$— | —CH$_2$OCH$_2$— | —CH=CH— | —OCH$_3$ | —N(CH$_3$)CH$_2$CH$_2$Et$_2$ |
| III-41 | H | H | —OCH$_2$CH$_2$— | —CH$_2$OCH$_2$— | —CH=CH— | H | —OCH$_2$CH$_2$—OCH$_3$ |
| III-42 | H | H | —OCH$_2$CH$_2$— | —CH$_2$OCH$_2$— | —CH=CH— | H | —OCH$_2$CH$_2$—SO$_2$Et |
| III-43 | H | H | —CH$_2$OCH$_2$— | —CH$_2$OCH$_2$— | —CH=CH— | H | —OCH$_2$CH$_2$—SO$_2$Et |
| III-44 | H | H | —CH$_2$OCH$_2$— | —CH$_2$OCH$_2$— | —CH=CH— | H | —OCH$_2$CH$_2$—OCH$_3$ |

$^A$In each of the compounds listed the geometry about the double bond may be cis or trans $^B$The position of $R^{10}$ and $R^{11}$ may vary depending on the position of the corresponding substituent in the relevant starting material In another embodiment of the invention the compounds are of the formula (IV):

Formula (IV)

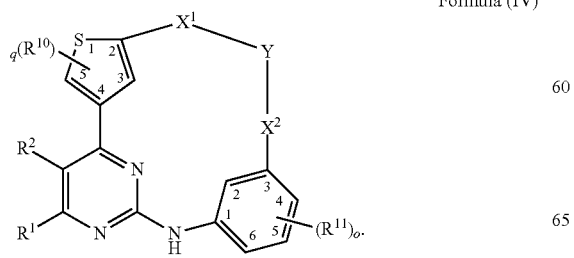

TABLE 3

| No | $R^1$ | $R^2$ | $X^1$ | $X^2$ | $Y^A$ | $R^{10B}$ | $R^{11B}$ |
|---|---|---|---|---|---|---|---|
| IV-1 | H | H | —OCH$_2$CH$_2$— | —CH$_2$OCH$_2$— | —CH=CH— | H | H |
| IV-2 | H | H | —OCH$_2$— | —CH$_2$OCH$_2$— | —CH=CH— | H | H |
| IV-3 | H | H | —OCH$_2$— | —CH$_2$OCH$_2$— | —CH=CH— | H | H |
| IV-4 | H | H | —CH$_2$OCH$_2$— | —CH$_2$OCH$_2$— | —CH=CH— | —OCH$_3$ | H |
| IV-5 | H | H | —OCH$_2$CH$_2$— | —CH$_2$OCH$_2$— | —CH=CH— | H | —OCH$_3$ |
| IV-6 | H | H | —OCH$_2$— | —CH$_2$OCH$_2$— | —CH=CH— | H | —OCH$_3$ |
| IV-7 | H | H | —OCH$_2$— | —CH$_2$OCH$_2$— | —CH=CH— | —OCH$_3$ | H |
| IV-8 | H | H | —OCH$_2$CH$_2$— | —CH$_2$CH$_2$O— | —CH=CH— | H | H |
| IV-9 | H | H | —OCH$_2$CH$_2$— | —CH$_2$O— | —CH=CH— | H | H |
| IV-10 | H | H | —CH$_2$OCH$_2$— | —CH$_2$OCH$_2$— | —CH=CH— | —OCH$_3$ | —OCH$_2$CH$_2$-pyrollidin-1-yl |
| IV-11 | H | H | —CH$_2$OCH$_2$— | —CH$_2$OCH$_2$— | —CH=CH— | H | —OCH$_2$CH$_2$—N(Et)$_2$ |
| IV-12 | H | H | —OCH$_2$— | —CH$_2$OCH$_2$— | —CH=CH— | —OCH$_3$ | —OCH$_2$CH$_2$—N(Et)$_2$ |
| IV-13 | H | H | —OCH$_2$— | —CH$_2$OCH$_2$— | —CH=CH— | H | —OCH$_2$CH$_2$—N(Et)$_2$ |
| IV-14 | H | H | —OCH$_2$— | —CH$_2$OCH$_2$— | —CH=CH— | —OCH$_3$ | —OCH$_2$CH$_2$—N(Et)$_2$ |
| IV-15 | H | H | —OCH$_2$CH$_2$— | —CH$_2$OCH$_2$— | —CH=CH— | H | —OCH$_2$CH$_2$—N(Et)$_2$ |
| IV-16 | H | H | —OCH$_2$CH$_2$— | —CH$_2$OCH$_2$— | —CH=CH— | —OCH$_3$ | —OCH$_2$CH$_2$—N(Et)$_2$ |
| IV-17 | H | H | —CH$_2$OCH$_2$— | —CH$_2$OCH$_2$— | —CH=CH— | —OCH$_3$ | —OCH$_2$CH$_2$—N(Et)$_2$ |
| IV-18 | H | H | —OCH$_2$— | —CH$_2$OCH$_2$— | —CH=CH— | —OCH$_3$ | —OCH$_2$CH$_2$-pyrollidin-1-yl |
| IV-19 | H | H | —OCH$_2$CH$_2$— | —CH$_2$OCH$_2$— | —CH=CH— | —OCH$_3$ | —OCH$_2$CH$_2$-pyrollidin-1-yl |
| IV-20 | H | H | —OCH$_2$— | —CH$_2$OCH$_2$— | —CH=CH— | H | —OCH$_2$CH$_2$-pyrollidin-1-yl |
| IV-21 | H | H | —OCH$_2$CH$_2$— | —CH$_2$OCH$_2$— | —CH=CH— | H | —OCH$_2$CH$_2$-pyrollidin-1-yl |
| IV-22 | H | H | —OCH$_2$CH$_2$— | —CH$_2$OCH$_2$— | —CH=CH— | F | —OCH$_2$CH$_2$—N(Et)$_2$ |
| IV-23 | H | CH$_3$ | —OCH$_2$CH$_2$— | —CH$_2$OCH$_2$— | —CH=CH— | H | —OCH$_2$CH$_2$—N(Et)$_2$ |
| IV-24 | H | H | —OCH$_2$CH$_2$— | —CH$_2$OCH$_2$— | —CH=CH— | H | morpholin-4-yl |
| IV-25 | H | H | —OCH$_2$— | —CH$_2$OCH$_2$— | —CH=CH— | H | morpholin-4-yl |
| IV-26 | H | H | —CH$_2$OCH$_2$— | —CH$_2$OCH$_2$— | —CH=CH— | H | morpholin-4-yl |
| IV-27 | H | H | —CH$_2$OCH$_2$— | —CH$_2$OCH$_2$— | —CH=CH— | —OCH$_3$ | morpholin-4-yl |
| IV-28 | H | H | —OCH$_2$CH$_2$— | —CH$_2$OCH$_2$— | —CH=CH— | H | —OCH$_2$CH$_2$CH$_2$—N(Et)$_2$ |
| IV-29 | H | H | —OCH$_2$CH$_2$— | —CH$_2$OCH$_2$— | —CH=CH— | F | —OCH$_2$CH$_2$-pyrollidin-1-yl |
| IV-30 | H | H | —CH$_2$OCH$_2$— | —CH$_2$OCH$_2$— | —CH=CH— | H | —OCH$_2$CH$_2$CH$_2$-pyrollidin-1-yl |
| IV-31 | H | H | —CH$_2$OCH$_2$— | —CH$_2$OCH$_2$— | —CH=CH— | H | 4-methy-piperazin-1-yl |
| IV-32 | H | H | —CH$_2$OCH$_2$— | —CH$_2$OCH$_2$— | —CH=CH— | —OCH$_3$ | 4-methy-piperazin-1-yl |
| IV-33 | H | H | —CH$_2$OCH$_2$— | —CH$_2$OCH$_2$— | —CH=CH— | F | —OCH$_2$CH$_2$CH$_2$-pyrollidin-1-yl |
| IV-34 | H | H | —OCH$_2$CH$_2$— | —CH$_2$OCH$_2$— | —CH=CH— | H | 4-methy-piperazin-1-yl |
| IV-35 | H | H | —OCH$_2$CH$_2$— | —CH$_2$OCH$_2$— | —CH=CH— | —OCH$_3$ | 4-methy-piperazin-1-yl |
| IV-36 | H | H | —CH$_2$OCH$_2$— | —CH$_2$OCH$_2$— | —CH=CH— | F | —OCH$_2$CH$_2$-pyrollidin-1-yl |
| IV-37 | H | CH$_3$ | —CH$_2$OCH$_2$— | —CH$_2$OCH$_2$— | —CH=CH— | H | —OCH$_2$CH$_2$-pyrollidin-1-yl |
| IV-38 | H | CH$_3$ | —CH$_2$OCH$_2$— | —CH$_2$OCH$_2$— | —CH=CH— | H | —OCH$_2$CH$_2$CH$_2$-pyrollidin-1-yl |
| IV-39 | H | H | —CH$_2$OCH$_2$— | —CH$_2$OCH$_2$— | —CH=CH— | H | —N(CH$_3$)CH$_2$CH$_2$Et$_2$ |
| IV-40 | H | H | —CH$_2$OCH$_2$— | —CH$_2$OCH$_2$— | —CH=CH— | —OCH$_3$ | —OCH$_2$CH$_2$-pyrollidin-1-yl |
| IV-41 | H | H | —OCH$_2$CH$_2$— | —CH$_2$OCH$_2$— | —CH=CH— | —OCH$_3$ | —N(CH$_3$)CH$_2$CH$_2$Et$_2$ |
| IV-42 | H | H | —OCH$_2$CH$_2$— | —CH$_2$OCH$_2$— | —CH=CH— | H | —OCH$_2$CH$_2$—OCH$_3$ |
| IV-43 | H | H | —OCH$_2$CH$_2$— | —CH$_2$OCH$_2$— | —CH=CH— | H | —OCH$_2$CH$_2$—SO$_2$Et |
| IV-44 | H | H | —CH$_2$OCH$_2$— | —CH$_2$OCH$_2$— | —CH=CH— | H | —OCH$_2$CH$_2$—SO$_2$Et |
| IV-46 | H | H | —CH$_2$OCH$_2$— | —CH$_2$OCH$_2$— | —CH=CH— | H | —OCH$_2$CH$_2$—OCH$_3$ |

$^A$In each of the compounds listed the geometry about the double bond may be cis or trans
$^B$The position of $R^{10}$ and $R^{11}$ may vary depending on the position of the corresponding substituent in the relevant starting material.

In another embodiment of the invention the compounds are of the formula (V):

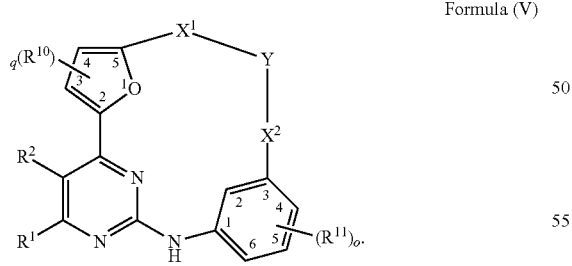

Formula (V)

Following analogous procedures to the ones described above and by making appropriate modifications to the starting materials the compounds listed in Table 4 may also be made.

TABLE 4

| No | $R^1$ | $R^2$ | $X^1$ | $X^2$ | $Y^A$ | $R^{10B}$ | $R^{11B}$ |
|---|---|---|---|---|---|---|---|
| V-1 | H | H | —OCH$_2$CH$_2$— | —CH$_2$OCH$_2$— | —CH=CH— | H | H |
| V-2 | H | H | —OCH$_2$— | —CH$_2$OCH$_2$— | —CH=CH— | H | H |

TABLE 4-continued

| No | $R^1$ | $R^2$ | $X^1$ | $X^2$ | $Y^A$ | $R^{10B}$ | $R^{11B}$ |
|---|---|---|---|---|---|---|---|
| V-3 | H | H | —OCH$_2$— | —CH$_2$OCH$_2$— | —CH=CH— | H | H |
| V-4 | H | H | —CH$_2$OCH$_2$— | —CH$_2$OCH$_2$— | —CH=CH— | —OCH$_3$ | H |
| V-5 | H | H | —OCH$_2$CH$_2$— | —CH$_2$OCH$_2$— | —CH=CH— | H | —OCH$_3$ |
| V-6 | H | H | —OCH$_2$— | —CH$_2$OCH$_2$— | —CH=CH— | H | —OCH$_3$ |
| V-7 | H | H | —OCH$_2$— | —CH$_2$OCH$_2$— | —CH=CH— | —OCH$_3$ | H |
| V-8 | H | H | —OCH$_2$CH$_2$— | —CH$_2$CH$_2$O— | —CH=CH— | H | H |
| V-9 | H | H | —OCH$_2$CH$_2$— | —CH$_2$O— | —CH=CH— | H | H |
| V-10 | H | H | —CH$_2$OCH$_2$— | —CH$_2$OCH$_2$— | —CH=CH— | —OCH$_3$ | —OCH$_2$CH$_2$-pyrollidin-1-yl |
| V-11 | H | H | —CH$_2$OCH$_2$— | —CH$_2$OCH$_2$— | —CH=CH— | H | —OCH$_2$CH$_2$—N(Et)$_2$ |
| V-12 | H | H | —OCH$_2$— | —CH$_2$OCH$_2$— | —CH=CH— | —OCH$_3$ | —OCH$_2$CH$_2$—N(Et)$_2$ |
| V-13 | H | H | —OCH$_2$— | —CH$_2$OCH$_2$— | —CH=CH— | H | —OCH$_2$CH$_2$—N(Et)$_2$ |
| V-14 | H | H | —OCH$_2$— | —CH$_2$OCH$_2$— | —CH=CH— | —OCH$_3$ | —OCH$_2$CH$_2$—N(Et)$_2$ |
| V-15 | H | H | —OCH$_2$CH$_2$— | —CH$_2$OCH$_2$— | —CH=CH— | H | —OCH$_2$CH$_2$—N(Et)$_2$ |
| V-16 | H | H | —OCH$_2$CH$_2$— | —CH$_2$OCH$_2$— | —CH=CH— | —OCH$_3$ | —OCH$_2$CH$_2$—N(Et)$_2$ |
| V-17 | H | H | —CH$_2$OCH$_2$— | —CH$_2$OCH$_2$— | —CH=CH— | —OCH$_3$ | —OCH$_2$CH$_2$—N(Et)$_2$ |
| V-18 | H | H | —OCH$_2$— | —CH$_2$OCH$_2$— | —CH=CH— | —OCH$_3$ | —OCH$_2$CH$_2$-pyrollidin-1-yl |
| V-19 | H | H | —OCH$_2$CH$_2$— | —CH$_2$OCH$_2$— | —CH=CH— | —OCH$_3$ | —OCH$_2$CH$_2$-pyrollidin-1-yl |
| V-20 | H | H | —OCH$_2$— | —CH$_2$OCH$_2$— | —CH=CH— | H | —OCH$_2$CH$_2$-pyrollidin-1-yl |
| V-21 | H | H | —OCH$_2$CH$_2$— | —CH$_2$OCH$_2$— | —CH=CH— | H | —OCH$_2$CH$_2$-pyrollidin-1-yl |
| V-22 | H | H | —OCH$_2$CH$_2$— | —CH$_2$OCH$_2$— | —CH=CH— | F | —OCH$_2$CH$_2$—N(Et)$_2$ |
| V-23 | H | CH$_3$ | —OCH$_2$CH$_2$— | —CH$_2$OCH$_2$— | —CH=CH— | H | —OCH$_2$CH$_2$—N(Et)$_2$ |
| V-24 | H | H | —OCH$_2$CH$_2$— | —CH$_2$OCH$_2$— | —CH=CH— | H | morpholin-4-yl |
| V-25 | H | H | —OCH$_2$— | —CH$_2$OCH$_2$— | —CH=CH— | H | morpholin-4-yl |
| V-26 | H | H | —CH$_2$OCH$_2$— | —CH$_2$OCH$_2$— | —CH=CH— | H | morpholin-4-yl |
| V-27 | H | H | —CH$_2$OCH$_2$— | —CH$_2$OCH$_2$— | —CH=CH— | —OCH$_3$ | morpholin-4-yl |
| V-28 | H | H | —OCH$_2$CH$_2$— | —CH$_2$OCH$_2$— | —CH=CH— | H | —OCH$_2$CH$_2$CH$_2$—N(Et)$_2$ |
| V-29 | H | H | —OCH$_2$CH$_2$— | —CH$_2$OCH$_2$— | —CH=CH— | F | —OCH$_2$CH$_2$-pyrollidin-1-yl |
| V-30 | H | H | —CH$_2$OCH$_2$— | —CH$_2$OCH$_2$— | —CH=CH— | H | —OCH$_2$CH$_2$CH$_2$-pyrollidin-1-yl |
| V-31 | H | H | —CH$_2$OCH$_2$— | —CH$_2$OCH$_2$— | —CH=CH— | H | 4-methy-piperazin-1-yl |
| V-32 | H | H | —CH$_2$OCH$_2$— | —CH$_2$OCH$_2$— | —CH=CH— | —OCH$_3$ | 4-methy-piperazin-1-yl |
| V-33 | H | H | —CH$_2$OCH$_2$— | —CH$_2$OCH$_2$— | —CH=CH— | F | —OCH$_2$CH$_2$-pyrollidin-1-yl |
| V-34 | H | H | —OCH$_2$CH$_2$— | —CH$_2$OCH$_2$— | —CH=CH— | H | 4-methy-piperazin-1-yl |
| V-35 | H | H | —OCH$_2$CH$_2$— | —CH$_2$OCH$_2$— | —CH=CH— | —OCH$_3$ | 4-methy-piperazin-1-yl |
| V-36 | H | H | —CH$_2$OCH$_2$— | —CH$_2$OCH$_2$— | —CH=CH— | F | —OCH$_2$CH$_2$-pyrollidin-1-yl |
| V-37 | H | CH$_3$ | —CH$_2$OCH$_2$— | —CH$_2$OCH$_2$— | —CH=CH— | H | —OCH$_2$CH$_2$-pyrollidin-1-yl |
| V-38 | H | CH$_3$ | —CH$_2$OCH$_2$— | —CH$_2$OCH$_2$— | —CH=CH— | H | —OCH$_2$CH$_2$CH$_2$-pyrollidin-1-yl |
| V-39 | H | H | —CH$_2$OCH$_2$— | —CH$_2$OCH$_2$— | —CH=CH— | H | —N(CH$_3$)CH$_2$CH$_2$Et$_2$ |
| V-40 | H | H | —CH$_2$OCH$_2$— | —CH$_2$OCH$_2$— | —CH=CH— | —OCH$_3$ | —OCH$_2$CH$_2$-pyrollidin-1-yl |
| V-41 | H | H | —OCH$_2$CH$_2$— | —CH$_2$OCH$_2$— | —CH=CH— | —OCH$_3$ | —N(CH$_3$)CH$_2$CH$_2$Et$_2$ |
| V-42 | H | H | —OCH$_2$CH$_2$— | —CH$_2$OCH$_2$— | —CH=CH— | H | —OCH$_2$CH$_2$—OCH$_3$ |
| V-43 | H | H | —OCH$_2$CH$_2$— | —CH$_2$OCH$_2$— | —CH=CH— | H | —OCH$_2$CH$_2$—SO$_2$Et |
| V-44 | H | H | —CH$_2$OCH$_2$— | —CH$_2$OCH$_2$— | —CH=CH— | H | —OCH$_2$CH$_2$—SO$_2$Et |
| V-46 | H | H | —CH$_2$OCH$_2$— | —CH$_2$OCH$_2$— | —CH=CH— | H | —OCH$_2$CH$_2$—OCH$_3$ |

$^A$In each of the compounds listed the geometry about the double bond may be cis or trans
$^B$The position of $R^{10}$ and $R^{11}$ may vary depending on the position of the corresponding substituent in the relevant starting material.

In another embodiment of the invention the compounds are of the formula (VI):

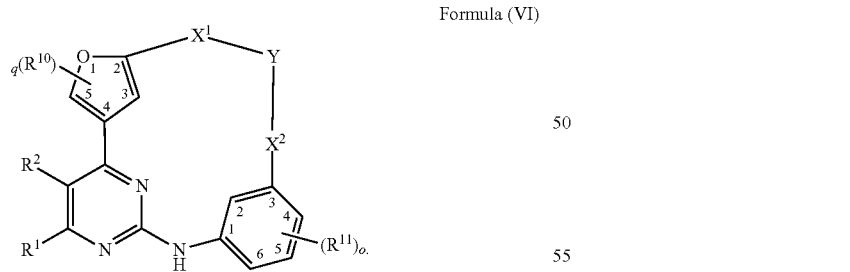

Formula (VI)

Following analogous procedures to the ones described above and by making appropriate modifications to the starting materials the compounds listed in Table 5 may also be made.

TABLE 5

| No | $R^1$ | $R^2$ | $X^1$ | $X^2$ | $Y^A$ | $R^{10B}$ | $R^{11B}$ |
|---|---|---|---|---|---|---|---|
| VI-1 | H | H | —OCH$_2$CH$_2$— | —CH$_2$OCH$_2$— | —CH=CH— | H | H |
| VI-2 | H | H | —OCH$_2$— | —CH$_2$OCH$_2$— | —CH=CH— | H | H |

TABLE 5-continued

| No | $R^1$ | $R^2$ | $X^1$ | $X^2$ | $Y^A$ | $R^{10B}$ | $R^{11B}$ |
|---|---|---|---|---|---|---|---|
| VI-3 | H | H | —OCH$_2$— | —CH$_2$OCH$_2$— | —CH=CH— | H | H |
| VI-4 | H | H | —CH$_2$OCH$_2$— | —CH$_2$OCH$_2$— | —CH=CH— | —OCH$_3$ | H |
| VI-5 | H | H | —OCH$_2$CH$_2$— | —CH$_2$OCH$_2$— | —CH=CH— | H | —OCH$_3$ |
| VI-6 | H | H | —OCH$_2$— | —CH$_2$OCH$_2$— | —CH=CH— | H | —OCH$_3$ |
| VI-7 | H | H | —OCH$_2$— | —CH$_2$OCH$_2$— | —CH=CH— | —OCH$_3$ | H |
| VI-8 | H | H | —OCH$_2$CH$_2$— | —CH$_2$CH$_2$O— | —CH=CH— | H | H |
| VI-9 | H | H | —OCH$_2$CH$_2$— | —CH$_2$O— | —CH=CH— | H | H |
| VI-10 | H | H | —CH$_2$OCH$_2$— | —CH$_2$OCH$_2$— | —CH=CH— | —OCH$_3$ | —OCH$_2$CH$_2$-pyrollidin-1-yl |
| VI-11 | H | H | —CH$_2$OCH$_2$— | —CH$_2$OCH$_2$— | —CH=CH— | H | —OCH$_2$CH$_2$—N(Et)$_2$ |
| VI-12 | H | H | —OCH$_2$— | —CH$_2$OCH$_2$— | —CH=CH— | —OCH$_3$ | —OCH$_2$CH$_2$—N(Et)$_2$ |
| VI-13 | H | H | —OCH$_2$— | —CH$_2$OCH$_2$— | —CH=CH— | H | —OCH$_2$CH$_2$—N(Et)$_2$ |
| VI-14 | H | H | —OCH$_2$— | —CH$_2$OCH$_2$— | —CH=CH— | —OCH$_3$ | —OCH$_2$CH$_2$—N(Et)$_2$ |
| VI-15 | H | H | —OCH$_2$CH$_2$— | —CH$_2$OCH$_2$— | —CH=CH— | H | —OCH$_2$CH$_2$—N(Et)$_2$ |
| VI-16 | H | H | —OCH$_2$CH$_2$— | —CH$_2$OCH$_2$— | —CH=CH— | —OCH$_3$ | —OCH$_2$CH$_2$—N(Et)$_2$ |
| VI-17 | H | H | —CH$_2$OCH$_2$— | —CH$_2$OCH$_2$— | —CH=CH— | —OCH$_3$ | —OCH$_2$CH$_2$—N(Et)$_2$ |
| VI-18 | H | H | —OCH$_2$— | —CH$_2$OCH$_2$— | —CH=CH— | —OCH$_3$ | —OCH$_2$CH$_2$-pyrollidin-1-yl |
| VI-19 | H | H | —OCH$_2$CH$_2$— | —CH$_2$OCH$_2$— | —CH=CH— | —OCH$_3$ | —OCH$_2$CH$_2$-pyrollidin-1-yl |
| VI-20 | H | H | —OCH$_2$— | —CH$_2$OCH$_2$— | —CH=CH— | H | —OCH$_2$CH$_2$-pyrollidin-1-yl |
| VI-21 | H | H | —OCH$_2$CH$_2$— | —CH$_2$OCH$_2$— | —CH=CH— | H | —OCH$_2$CH$_2$-pyrollidin-1-yl |
| VI-22 | H | H | —OCH$_2$CH$_2$— | —CH$_2$OCH$_2$— | —CH=CH— | F | —OCH$_2$CH$_2$—N(Et)$_2$ |
| VI-23 | H | CH$_3$ | —OCH$_2$CH$_2$— | —CH$_2$OCH$_2$— | —CH=CH— | H | —OCH$_2$CH$_2$—N(Et)$_2$ |
| VI-24 | H | H | —OCH$_2$CH$_2$— | —CH$_2$OCH$_2$— | —CH=CH— | H | morpholin-4-yl |
| VI-25 | H | H | —OCH$_2$— | —CH$_2$OCH$_2$— | —CH=CH— | H | morpholin-4-yl |
| VI-26 | H | H | —CH$_2$OCH$_2$— | —CH$_2$OCH$_2$— | —CH=CH— | H | morpholin-4-yl |
| VI-27 | H | H | —CH$_2$OCH$_2$— | —CH$_2$OCH$_2$— | —CH=CH— | —OCH$_3$ | morpholin-4-yl |
| VI-28 | H | H | —OCH$_2$CH$_2$— | —CH$_2$OCH$_2$— | —CH=CH— | H | —OCH$_2$CH$_2$CH$_2$—N(Et)$_2$ |
| VI-29 | H | H | —OCH$_2$CH$_2$— | —CH$_2$OCH$_2$— | —CH=CH— | F | —OCH$_2$CH$_2$-pyrollidin-1-yl |
| VI-30 | H | H | —CH$_2$OCH$_2$— | —CH$_2$OCH$_2$— | —CH=CH— | H | —OCH$_2$CH$_2$CH$_2$-pyrollidin-1-yl |
| VI-31 | H | H | —CH$_2$OCH$_2$— | —CH$_2$OCH$_2$— | —CH=CH— | H | 4-methy-piperazin-1-yl |
| VI-32 | H | H | —CH$_2$OCH$_2$— | —CH$_2$OCH$_2$— | —CH=CH— | —OCH$_3$ | 4-methy-piperazin-1-yl |
| VI-33 | H | H | —CH$_2$OCH$_2$— | —CH$_2$OCH$_2$— | —CH=CH— | F | —OCH$_2$CH$_2$CH$_2$-pyrollidin-1-yl |
| VI-34 | H | H | —OCH$_2$CH$_2$— | —CH$_2$OCH$_2$— | —CH=CH— | H | 4-methy-piperazin-1-yl |
| VI-35 | H | H | —OCH$_2$CH$_2$— | —CH$_2$OCH$_2$— | —CH=CH— | —OCH$_3$ | 4-methy-piperazin-1-yl |
| VI-36 | H | H | —CH$_2$OCH$_2$— | —CH$_2$OCH$_2$— | —CH=CH— | F | —OCH$_2$CH$_2$-pyrollidin-1-yl |
| VI-37 | H | CH$_3$ | —CH$_2$OCH$_2$— | —CH$_2$OCH$_2$— | —CH=CH— | H | —OCH$_2$CH$_2$-pyrollidin-1-yl |
| VI-38 | H | CH$_3$ | —CH$_2$OCH$_2$— | —CH$_2$OCH$_2$— | —CH=CH— | H | —OCH$_2$CH$_2$CH$_2$-pyrollidin-1-yl |
| VI-39 | H | H | —CH$_2$OCH$_2$— | —CH$_2$OCH$_2$— | —CH=CH— | H | —N(CH$_3$)CH$_2$CH$_2$Et$_2$ |
| VI-40 | H | H | —CH$_2$OCH$_2$— | —CH$_2$OCH$_2$— | —CH=CH— | —OCH$_3$ | —OCH$_2$CH$_2$-pyrollidin-1-yl |
| VI-41 | H | H | —OCH$_2$CH$_2$— | —CH$_2$OCH$_2$— | —CH=CH— | —OCH$_3$ | —N(CH$_3$)CH$_2$CH$_2$Et$_2$ |
| VI-42 | H | H | —OCH$_2$CH$_2$— | —CH$_2$OCH$_2$— | —CH=CH— | H | —OCH$_2$CH$_2$—OCH$_3$ |
| VI-43 | H | H | —OCH$_2$CH$_2$— | —CH$_2$OCH$_2$— | —CH=CH— | H | —OCH$_2$CH$_2$—SO$_2$Et |
| VI-44 | H | H | —CH$_2$OCH$_2$— | —CH$_2$OCH$_2$— | —CH=CH— | H | —OCH$_2$CH$_2$—SO$_2$Et |
| VI-46 | H | H | —CH$_2$OCH$_2$— | —CH$_2$OCH$_2$— | —CH=CH— | H | —OCH$_2$CH$_2$—OCH$_3$ |

$^A$In each of the compounds listed the geometry about the double bond may be cis or trans
$^B$The position of $R^{10}$ and $R^{11}$ may vary depending on the position of the corresponding substituent in the relevant starting material.

In another embodiment of the invention the compounds are of the formula (VII):

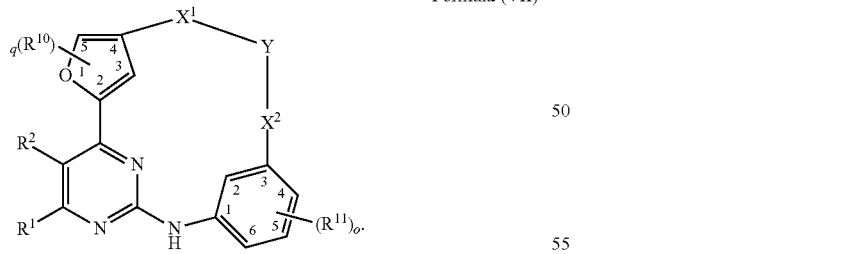

Formula (VII)

Following analogous procedures to the ones described above and by making appropriate modifications to the starting materials the compounds listed in Table 6 may also be made.

TABLE 6

| No | $R^1$ | $R^2$ | $X^1$ | $X^2$ | $Y^A$ | $R^{10B}$ | $R^{11B}$ |
|---|---|---|---|---|---|---|---|
| VII-1 | H | H | —OCH$_2$CH$_2$— | —CH$_2$OCH$_2$— | —CH=CH— | H | H |
| VII-2 | H | H | —OCH$_2$— | —CH$_2$OCH$_2$— | —CH=CH— | H | H |
| VII-3 | H | H | —OCH$_2$— | —CH$_2$OCH$_2$— | —CH=CH— | H | H |

TABLE 6-continued

| No | R$^1$ | R$^2$ | X$^1$ | X$^2$ | Y$^A$ | R$^{10B}$ | R$^{11B}$ |
|---|---|---|---|---|---|---|---|
| VII-4 | H | H | —CH$_2$OCH$_2$— | —CH$_2$OCH$_2$— | —CH=CH— | —OCH$_3$ | H |
| VII-5 | H | H | —OCH$_2$CH$_2$— | —CH$_2$OCH$_2$— | —CH=CH— | H | —OCH$_3$ |
| VII-6 | H | H | —OCH$_2$— | —CH$_2$OCH$_2$— | —CH=CH— | H | —OCH$_3$ |
| VII-7 | H | H | —OCH$_2$— | —CH$_2$OCH$_2$— | —CH=CH— | —OCH$_3$ | H |
| VII-8 | H | H | —OCH$_2$CH$_2$— | —CH$_2$CH$_2$O— | —CH=CH— | H | H |
| VII-9 | H | H | —OCH$_2$CH$_2$— | —CH$_2$O— | —CH=CH— | H | H |
| VII-10 | H | H | —CH$_2$OCH$_2$— | —CH$_2$OCH$_2$— | —CH=CH— | —OCH$_3$ | —OCH$_2$CH$_2$-pyrollidin-1-yl |
| VII-11 | H | H | —CH$_2$OCH$_2$— | —CH$_2$OCH$_2$— | —CH=CH— | H | —OCH$_2$CH$_2$—N(Et)$_2$ |
| VII-12 | H | H | —OCH$_2$— | —CH$_2$OCH$_2$— | —CH=CH— | —OCH$_3$ | —OCH$_2$CH$_2$—N(Et)$_2$ |
| VII-13 | H | H | —OCH$_2$— | —CH$_2$OCH$_2$— | —CH=CH— | H | —OCH$_2$CH$_2$—N(Et)$_2$ |
| VII-14 | H | H | —OCH$_2$— | —CH$_2$OCH$_2$— | —CH=CH— | —OCH$_3$ | —OCH$_2$CH$_2$—N(Et)$_2$ |
| VII-15 | H | H | —OCH$_2$CH$_2$— | —CH$_2$OCH$_2$— | —CH=CH— | H | —OCH$_2$CH$_2$—N(Et)$_2$ |
| VII-16 | H | H | —OCH$_2$CH$_2$— | —CH$_2$OCH$_2$— | —CH=CH— | —OCH$_3$ | —OCH$_2$CH$_2$—N(Et)$_2$ |
| VII-17 | H | H | —CH$_2$OCH$_2$— | —CH$_2$OCH$_2$— | —CH=CH— | —OCH$_3$ | —OCH$_2$CH$_2$—N(Et)$_2$ |
| VII-18 | H | H | —OCH$_2$— | —CH$_2$OCH$_2$— | —CH=CH— | —OCH$_3$ | —OCH$_2$CH$_2$-pyrollidin-1-yl |
| VII-19 | H | H | —OCH$_2$CH$_2$— | —CH$_2$OCH$_2$— | —CH=CH— | —OCH$_3$ | —OCH$_2$CH$_2$-pyrollidin-1-yl |
| VII-20 | H | H | —OCH$_2$— | —CH$_2$OCH$_2$— | —CH=CH— | H | —OCH$_2$CH$_2$-pyrollidin-1-yl |
| VII-21 | H | H | —OCH$_2$CH$_2$— | —CH$_2$OCH$_2$— | —CH=CH— | H | —OCH$_2$CH$_2$-pyrollidin-1-yl |
| VII-22 | H | H | —OCH$_2$CH$_2$— | —CH$_2$OCH$_2$— | —CH=CH— | F | —OCH$_2$CH$_2$—N(Et)$_2$ |
| VII-23 | H | CH$_3$ | —OCH$_2$CH$_2$— | —CH$_2$OCH$_2$— | —CH=CH— | H | —OCH$_2$CH$_2$—N(Et)$_2$ |
| VII-24 | H | H | —OCH$_2$CH$_2$— | —CH$_2$OCH$_2$— | —CH=CH— | H | morpholin-4-yl |
| VII-25 | H | H | —OCH$_2$— | —CH$_2$OCH$_2$— | —CH=CH— | H | morpholin-4-yl |
| VII-26 | H | H | —CH$_2$OCH$_2$— | —CH$_2$OCH$_2$— | —CH=CH— | H | morpholin-4-yl |
| VII-27 | H | H | —CH$_2$OCH$_2$— | —CH$_2$OCH$_2$— | —CH=CH— | —OCH$_3$ | morpholin-4-yl |
| VII-28 | H | H | —OCH$_2$CH$_2$— | —CH$_2$OCH$_2$— | —CH=CH— | H | —OCH$_2$CH$_2$CH$_2$—N(Et)$_2$ |
| VII-29 | H | H | —OCH$_2$CH$_2$— | —CH$_2$OCH$_2$— | —CH=CH— | F | —OCH$_2$CH$_2$-pyrollidin-1-yl |
| VII-30 | H | H | —CH$_2$OCH$_2$— | —CH$_2$OCH$_2$— | —CH=CH— | H | —OCH$_2$CH$_2$CH$_2$-pyrollidin-1-yl |
| VII-31 | H | H | —CH$_2$OCH$_2$— | —CH$_2$OCH$_2$— | —CH=CH— | H | 4-methy-piperazin-1-yl |
| VII-32 | H | H | —CH$_2$OCH$_2$— | —CH$_2$OCH$_2$— | —CH=CH— | —OCH$_3$ | 4-methy-piperazin-1-yl |
| VII-33 | H | H | —CH$_2$OCH$_2$— | —CH$_2$OCH$_2$— | —CH=CH— | F | —OCH$_2$CH$_2$CH$_2$-pyrollidin-1-yl |
| VII-34 | H | H | —CH$_2$OCH$_2$— | —CH$_2$OCH$_2$— | —CH=CH— | H | 4-methy-piperazin-1-yl |
| VII-35 | H | H | —CH$_2$OCH$_2$— | —CH$_2$OCH$_2$— | —CH=CH— | —OCH$_3$ | 4-methy-piperazin-1-yl |
| VII-36 | H | H | —CH$_2$OCH$_2$— | —CH$_2$OCH$_2$— | —CH=CH— | F | —OCH$_2$CH$_2$-pyrollidin-1-yl |
| VII-37 | H | CH$_3$ | —CH$_2$OCH$_2$— | —CH$_2$OCH$_2$— | —CH=CH— | H | —OCH$_2$CH$_2$-pyrollidin-1-yl |
| VII-38 | H | CH$_3$ | —CH$_2$OCH$_2$— | —CH$_2$OCH$_2$— | —CH=CH— | H | —OCH$_2$CH$_2$-pyrollidin-1-yl |
| VII-39 | H | H | —CH$_2$OCH$_2$— | —CH$_2$OCH$_2$— | —CH=CH— | H | —N(CH$_3$)CH$_2$CH$_2$Et$_2$ |
| VII-40 | H | H | —CH$_2$OCH$_2$— | —CH$_2$OCH$_2$— | —CH=CH— | —OCH$_3$ | —OCH$_2$CH$_2$-pyrollidin-1-yl |
| VII-41 | H | H | —OCH$_2$CH$_2$— | —CH$_2$OCH$_2$— | —CH=CH— | —OCH$_3$ | —N(CH$_3$)CH$_2$CH$_2$Et$_2$ |
| VII-42 | H | H | —OCH$_2$CH$_2$— | —CH$_2$OCH$_2$— | —CH=CH— | H | —OCH$_2$CH$_2$—OCH$_3$ |
| VII-43 | H | H | —OCH$_2$CH$_2$— | —CH$_2$OCH$_2$— | —CH=CH— | H | —OCH$_2$CH$_2$—SO$_2$Et |
| VII-44 | H | H | —CH$_2$OCH$_2$— | —CH$_2$OCH$_2$— | —CH=CH— | H | —OCH$_2$CH$_2$—SO$_2$Et |
| VII-46 | H | H | —CH$_2$OCH$_2$— | —CH$_2$OCH$_2$— | —CH=CH— | H | —OCH$_2$CH$_2$—OCH$_3$ |

$^A$In each of the compounds listed the geometry about the double bond may be cis or trans
$^B$The position of R$^{10}$ and R$^{11}$ may vary depending on the position of the corresponding substituent in the relevant starting material.

BIOLOGICAL TESTING

1. In Vitro Kinase Activity Assay

The recombinant enzymes (CDK2/CyclinA, FLT3, JAK2 and JAK2 V617F) were purchased from Invitrogen (Cat #PV3267, 3182, 4210 and 4347 respectively). All assays were carried out in 384-well white microtiter plates using the PKLight assay system from Cambrex (East Rutherford, N.J.). This assay platform is essentially a luminometric assay for the detection of ATP in the reaction using a luciferase-coupled reaction. For CDK2/Cyclin A assay, the reaction mixture consisted of the following components in 25 μL assay buffer (50 mM Hepes pH 7.5, 10 mM MgCl$_2$, 5 mM MnCl$_2$, 5 mM BGP, 1 mM DTT, 0.1 mM sodium orthovanadate), 1.4 μg/mL of CDK2/Cyclin A complex, 0.5 μM of RbING substrate (Invitrogen, Cat #PV2939) and 0.5 μM of ATP. The compounds were tested at 8 concentrations prepared from 4-fold serial dilution starting at 10 μM. The reaction was incubated at room temperature for 2 hr. 13 μL of PKLight ATP detection reagent was added and the reaction was incubated for 10 min. Luminescence signals were detected on a multi-label plate reader (Victor$^2$ V 1420, Perkin-Elmer). The other kinase assays were identical except for the following differences in reagents. For FLT3 assays, the reaction contained 2.0 μg/mL FLT3 enzyme, 5 μM of poly(Glu,Tyr) substrate (Sigma, Cat #P0275) and 4 μM of ATP. For JAK2 assays, the reaction contained 0.6 μg/mL of JAK2 enzyme, 2 μM of poly(Glu,Ala,Tyr) substrate (Sigma, Cat #P3899) and 0.2 μM of ATP. For JAK2 V617F mutant assays, the reaction contained 8.0 μg/mL of JAK2 mutant enzyme, 2 μM of poly(Glu,Ala,Tyr) substrate (Sigma, Cat #P3899) and 0.2 μM of ATP. The analytical software, Prism 4.0 (GraphPad Software Pte Ltd) was used to generate IC$_{50}$ values from the data. IC$_{50}$ is defined as the concentration of compound required for 50% inhibition of kinase enzyme activity. IC$_{50}$ data are shown in Table 7 below.

TABLE 7

In vitro kinase activity assay IC$_{50}$ data

| Compound No. | CDK2 | FLT3 | JAK2 | JAK2 V617F mutant |
|---|---|---|---|---|
| 6 | +++ | +++ | +++ | NT |
| 7 | + | +++ | + | NT |
| 13 | ++ | +++ | +++ | +++ |
| 14 | + | +++ | +++ | +++ |
| 15 | ++ | +++ | +++ | +++ |
| 19 | + | +++ | +++ | +++ |
| 20 | + | +++ | +++ | +++ |
| 29 | + | +++ | +++ | +++ |
| 32 | ++ | +++ | +++ | NT |

TABLE 7-continued

In vitro kinase activity assay IC$_{50}$ data

| Compound No. | CDK2 | FLT3 | JAK2 | JAK2 V617F mutant |
|---|---|---|---|---|
| 33 | + | +++ | +++ | NT |
| 36 | ++ | +++ | +++ | NT |
| 38 | + | +++ | +++ | NT |
| 40 | + | +++ | +++ | NT |
| 46 | ++ | +++ | +++ | NT |
| 48 | + | +++ | +++ | NT |
| 50 | + | +++ | +++ | NT |
| 52 | + | +++ | +++ | NT |
| 53 | ++ | +++ | +++ | NT |
| 55 | + | +++ | +++ | NT |
| 56 | ++ | +++ | +++ | NT |

NT = not tested
IC$_{50}$ ≤ 1 µM +++
1 µM < IC$_{50}$ ≤ 5 µM ++
IC$_{50}$ > 5 µM +

2. Cell Lines

The cell lines used in the studies are summarized in Table 8 below:

TABLE 8

Characteristics of human cell lines used

| Cell lines | Tumour origin | Supplier | Basic culture medium | Seeding density (per well) |
|---|---|---|---|---|
| HCT116 | Colon | ATCC | McCoy's medium | 3,000 |
| Colo205 | Colon | ATCC | RPMI 1640 | 5,000 |
| HL60 | AML | ATCC | RPMI 1640 | 8,000 |
| MV4-11 | AML | ATCC | Iscove's MEM | 6,000 |
| HEL | Erythroleukemia | ATCC | RPMI 1640 | 6,000 |
| DU145 | Prostate | ATCC | RPMI 6140 | 1,000 |
| U266 | Myeloma | DSMZ | RPMI 6140 | 10,000 |
| Karpas | B-cell Lymphoma | DSMZ | RPMI 1640 | 10,000 |

3. Cell-Based Proliferation Assay for Determination of GI$_{50}$ Values

The biological efficacy of the invention was demonstrated by the following assay. Human cancer cell lines HL60 (acute myeloid leukemia cell line), Colo205 (colon adenocarcinoma cell line), HEL92.1.7 (erythroleukemia cell line) and MV4-11 (acute myeloid leukemia cell line) were obtained from ATCC. They were cultivated in the media according to the ATCC work instructions. Colo205 cells were seeded in 96-wells plate at 5000 cells per well. HEL92.1.7 and MV4-11 cells were seeded at 6000 cells per well while HL60 cells were seeded at 8000 cells per well in 96 well plate. The plates were incubated at 37° C., 5% CO$_2$, for 24 h. Cells were treated with compounds at various concentrations for 96 h. Cell growth was then monitored using Celltiter96 Aqueous One Solution Cell Proliferation Assay from Promega (Madison Wis.). Dose response curves were plotted to determine GI$_{50}$ values for the compounds using XL-fit (ID Business Solution, Emeryville, Calif.). GI$_{50}$ is defined as the concentration of compound required for 50% inhibition of cell growth. The compounds of this invention inhibited cell proliferation as shown in Table 9 below. The data indicated that the compounds of this invention are active in the inhibition of tumour cell growth.

TABLE 9

Cell-based proliferation assay GI$_{50}$ data

| | HL60 | Colo205 | HEL92.1.7 | MV4-11 |
|---|---|---|---|---|
| 6 | ++ | ++ | NT | NT |
| 7 | +++ | + | + | + |
| 13 | +++ | ++ | ++ | +++ |
| 14 | +++ | ++ | +++ | +++ |
| 15 | +++ | ++ | ++ | +++ |
| 19 | +++ | +++ | +++ | +++ |
| 20 | ++ | + | + | +++ |
| 29 | +++ | NT | ++ | +++ |
| 32 | +++ | NT | ++ | +++ |
| 33 | ++ | NT | ++ | +++ |
| 36 | +++ | NT | ++ | +++ |
| 38 | +++ | NT | ++ | +++ |
| 40 | +++ | NT | +++ | +++ |
| 46 | +++ | NT | ++ | +++ |
| 48 | +++ | +++ | +++ | +++ |
| 50 | +++ | NT | ++ | +++ |
| 52 | +++ | NT | +++ | +++ |
| 53 | +++ | NT | ++ | +++ |
| 55 | ++ | NT | ++ | +++ |
| 56 | +++ | NT | ++ | +++ |

NT = not tested
GI$_{50}$ ≤ 1 µM +++
1 µM < GI$_{50}$ ≤ 5 µM ++
GI$_{50}$ > 5 µM +

In Vivo Antineoplastic (or Anti-Tumour) Effect:

The efficacy of the compounds of the invention can then be determined using in vivo animal xenograft studies. The animal xenograft model is one of the most commonly used in vivo cancer models.

In these studies Female athymic nude mice (Harlan), 12-14 weeks of age would be implanted subcutaneously in the flank with 5×10$^6$ cells of MV4-11 human biphenotypic B myelomonocytic leukemia cells in Matrigel (BD Biosciences, in 1:1). When the tumour reaches the size 100 mm$^3$, the xenograft nude mice would be paired-match into various treatment groups. The selected kinase inhibitors would be dissolved in appropriate vehicles and administered to xenograft nude mice intraperitoneally or orally daily for 21 days. The dosing volume will be 0.01 ml/g body weight. Tumour volume will be calculated every second day or twice-a-week of post injection using the formula: Volume (mm$^3$)= (w$^2$×l)/2, where w=width and l=length in mm of a MV4-11 tumour. Compounds of this invention that are tested would show significant reduction in tumour volume relative to controls treated with vehicle only. The result will therefore indicate that compounds of this invention are efficacious in treating a proliferative disease such as cancer.

The details of specific embodiments described in this invention are not to be construed as limitations. Various equivalents and modifications may be made without departing from the essence and scope of this invention, and it is understood that such equivalent embodiments are part of this invention.

What is claimed is:
1. A compound of formula I:

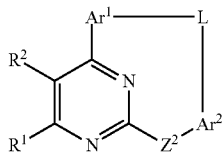

Formula (I)

wherein:
R$^1$ and R$^2$ are each independently selected from the group consisting of: H, halogen, alkyl, alkenyl, alkynyl, haloalkyl, haloalkenyl, heteroalkyl, cycloalkyl, cycloalkenyl, heterocycloalkyl, heterocycloalkenyl, aryl, heteroaryl, cycloalkylalkyl, heterocycloalkylalkyl, arylalkyl, heteroarylalkyl, arylalkenyl, cycloalkylheteroalkyl, heterocycloalkylheteroalkyl, heteroarylheteroalkyl, arylheteroalkyl, hydroxy, hydroxyalkyl, alkoxy, alkoxyalkyl, alkoxyaryl, alkenyloxy, alkynyloxy, cycloalkyloxy, heterocycloalkyloxy, aryloxy, arylalkyloxy, phenoxy, benzyloxy, heteroaryloxy, amino, alkylamino, aminoalkyl, acylamino, arylamino, sulfonylamino, sulfinylamino, —COOH, —COR$^3$, —COOR$^3$, —CONHR$^3$, —NHCOR$^3$, —NHCOOR$^3$, —NHCONHR$^3$, alkoxycarbonyl, alkylaminocarbonyl, alkylsulfonyl, alkylsulfinyl, arylsulfonyl, arylsulfinyl, aminosulfonyl, —SR$^3$, R$^4$S(O)R$^6$—, R$^4$S(O)$_2$R$^6$—, R$^4$C(O)N(R$^5$)R$^6$—, R$^4$SO$_2$N(R$^5$)R$^6$—, R$^4$N(R$^5$)C(O)R$^6$—, R$^4$N(R$^5$)SO$_2$R$^6$—, R$^4$N(R$^5$)C(O)N(R$^5$)R$^6$— and acyl, each of which may be optionally substituted;
each R$^3$, R$^4$, and R$^5$ is independently selected from the group consisting of H, alkyl, alkenyl, alkynyl, haloalkyl, heteroalkyl, cycloalkyl, heterocycloalkyl, aryl, heteroaryl, cycloalkylalkyl, heterocycloalkylalkyl, arylalkyl, heteroarylalkyl and acyl, each of which may be optionally substituted;
each R$^6$ is independently selected from the group consisting of a bond, alkyl, alkenyl, alkynyl, haloalkyl, heteroalkyl, cycloalkyl, heterocycloalkyl, aryl, heteroaryl, cycloalkylalkyl, heterocycloalkylalkyl, arylalkyl, heteroarylalkyl and acyl, each of which may be optionally substituted;
Z$^2$ is selected from the group consisting of a bond, O, S, —N(R$^7$)—, —N(R$^7$)C$_{1-2}$alkyl-, and —C$_{1-2}$alkylN(R$^7$)—;
each R$^7$ is independently selected from the group consisting of H, alkyl, alkenyl, alkynyl, haloalkyl, heteroalkyl, cycloalkyl, heterocycloalkyl, aryl, heteroaryl, cycloalkylalkyl, heterocycloalkylalkyl, arylalkyl, heteroarylalkyl and acyl, each of which may be optionally substituted;
Ar$^1$ and Ar$^2$ are independently selected from the group consisting of aryl and heteroaryl, each of which may be optionally substituted, with the proviso that Ar$^1$ and Ar$^2$ are not both phenylene;
L is a group of formula:

—X$^1$—Y—X$^2$— wherein X$^1$ is attached to Ar$^1$ and X$^2$ is attached to Ar$^2$, and wherein X$^1$, X$^2$ and Y are selected such that the group L has between 5 and 15 atoms in the normal chain,
X$^1$ and X$^2$ are each independently a heteroalkyl group containing at least one oxygen atom in the normal chain,
Y is a group of formula —CR$^a$=CR$^b$— or an optionally substituted cycloalkyl group,
wherein R$^a$ and R$^b$ are each independently selected from the group consisting of H, alkyl, alkenyl, alkynyl, haloalkyl, heteroalkyl, cycloalkyl, heterocycloalkyl, aryl, heteroaryl, cycloalkylalkyl, heterocycloalkylalkyl, arylalkyl, heteroarylalkyl and acyl, each of which may be optionally substituted, or
R$^a$ and R$^b$ are joined such that when taken together with the carbon atoms to which they are attached they form a cycloalkenyl or cycloheteroalkenyl group;
or a pharmaceutically acceptable salt, N-oxide, or ester thereof.

2. A compound according to claim 1 wherein Z$^2$ is —N(H)—.

3. A compound according to claim 1 wherein Ar$^1$ is selected from the group consisting of:

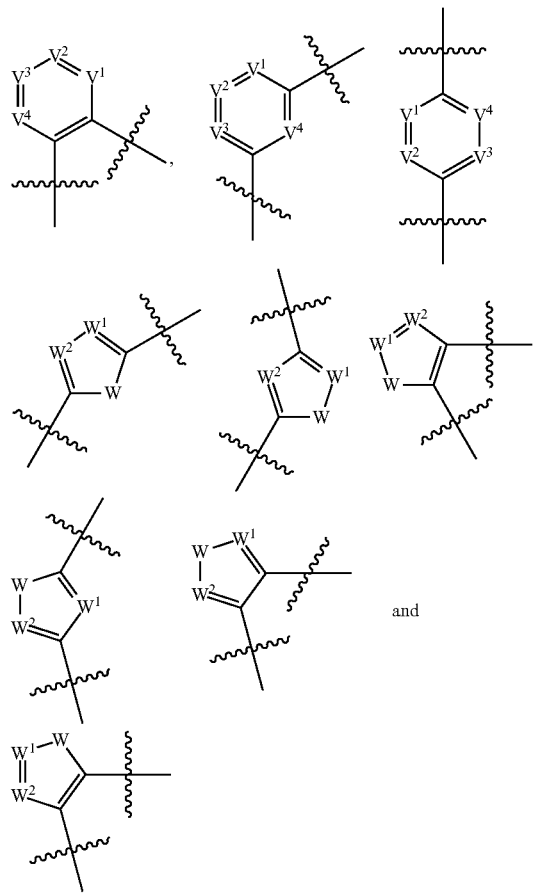

and wherein V$^1$, V$^2$, V$^3$ and V$^4$ are each independently selected from the group consisting of N, and C(R$^{10}$);
W is selected from the group consisting of O, S and N(R$^{10}$);
W$^1$ and W$^2$ are each independently selected from the group consisting of N and C(R$^{10}$);
wherein each R$^{10}$ is independently selected from the group consisting of: H, halogen, alkyl, alkenyl, alkynyl, haloalkyl, haloalkenyl, heteroalkyl, cycloalkyl, cycloalkenyl, heterocycloalkyl, heterocycloalkenyl, aryl, heteroaryl, cycloalkylalkyl, heterocycloalkylalkyl, arylalkyl, heteroarylalkyl, arylalkenyl, cycloalkylheteroalkyl, heterocycloalkylheteroalkyl, heteroarylheteroalkyl, arylheteroalkyl, hydroxy, hydroxyalkyl, alkoxy, alkoxyalkyl, alkoxyaryl, alkenyloxy, alkynyloxy, cycloalkylkoxy, heterocycloalkyloxy, aryloxy, arylalkyloxy, phenoxy, benzyloxy, heteroaryloxy, amino, alkylamino, aminoalkyl, acylamino, arylamino, sulfonylamino, sulfinylamino, —COOH, —COR$^3$, —COOR$^3$, —CONHR$^3$, —NHCOR$^3$, —NHCOOR$^3$, —NHCONHR$^3$, alkoxycarbonyl, alkylaminocarbonyl, sulfonyl, alkylsulfonyl, alkylsulfinyl, arylsulfonyl, arylsulfinyl, aminosulfonyl, —SR$^3$, R$^4$S(O)R$^6$—, R$^4$S(O)$_2$R$^6$—, R$^4$C(O)N(R$^5$)R$^6$—, R$^4$SO$_2$N(R$^5$)R$^6$—, R$^4$N(R$^5$)C(O)R$^6$—, R$^4$N(R$^5$)SO$_2$R$^6$—, R$^4$N(R$^5$)C(O)N(R$^5$)R$^6$— and acyl, each of which may be optionally substituted.

4. A compound according to claim 3 wherein Ar$^1$ is selected from the group consisting of:

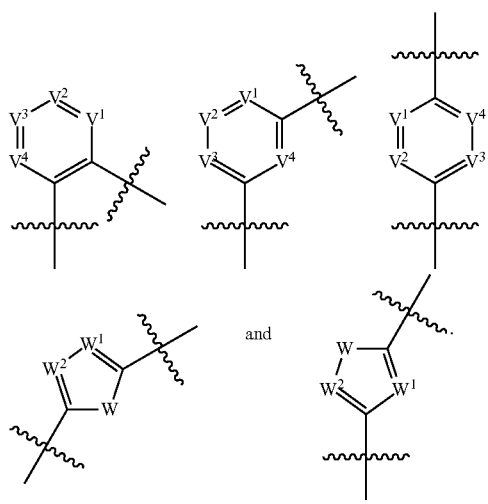

5. A compound according to claim 1 wherein Ar$^1$ is selected from the group consisting of:

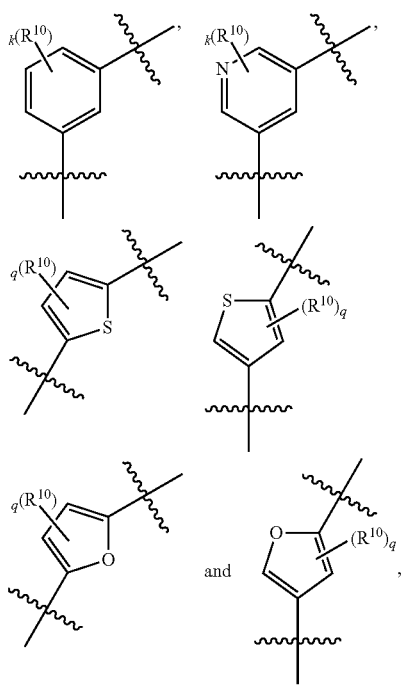

wherein each R$^{10}$ is independently selected from the group consisting of: H, halogen, alkyl, alkenyl, alkynyl, haloalkyl, haloalkenyl, heteroalkyl, cycloalkyl, cycloalkenyl, heterocycloalkyl, heterocycloalkenyl, aryl, heteroaryl, cycloalkylalkyl, heterocycloalkylalkyl, arylalkyl, heteroarylalkyl, arylalkenyl, cycloalkylheteroalkyl, heterocycloalkylheteroalkyl, heteroarylheteroalkyl, arylheteroalkyl, hydroxy, hydroxyalkyl, alkoxy, alkoxyalkyl, alkoxyaryl, alkenyloxy, alkynyloxy, cycloalkylkoxy, heterocycloalkyloxy, aryloxy, arylalkyloxy, phenoxy, benzyloxy, heteroaryloxy, amino, alkylamino, aminoalkyl, acylamino, arylamino, sulfonylamino, sulfinylamino, —COOH, —COR$^3$, —COOR$^3$, —CONHR$^3$, —NHCOR$^3$, —NHCOOR$^3$, —NHCONHR$^3$, alkoxycarbonyl, alkylaminocarbonyl, alkylsulfonyl, alkylsulfinyl, arylsulfonyl, arylsulfinyl, aminosulfonyl, —SR$^3$, R$^4$S(O)R$^6$—, R$^4$S(O)$_2$R$^6$—, R$^4$C(O)N(R$^5$)R$^6$—, R$^4$SO$_2$N(R$^5$)R$^6$—, R$^4$N(R$^5$)C(O)R$^6$—, R$^4$N(R$^5$)SO$_2$R$^6$—, R$^4$N(R$^5$)C(O)N(R$^5$)R$^6$— and acyl, each of which may be optionally substituted;

k is an integer selected from the group consisting of 0, 1, 2, 3, and 4;

n is an integer selected from the group consisting of 0, 1, 2, and 3, and q is an integer selected from the group consisting of 0, 1, and 2.

6. A compound according to claim 5 wherein Ar$^1$ is selected from the group consisting of:

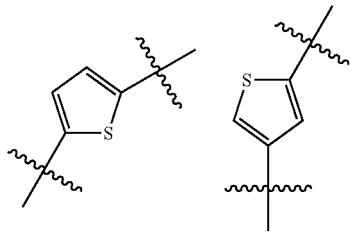

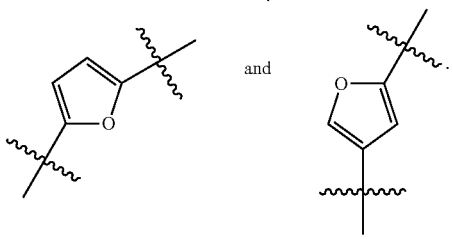

7. A compound according to claim 1 wherein Ar$^2$ is selected from the group consisting of:

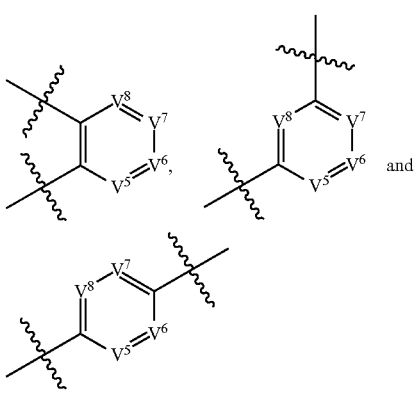

wherein V$^5$, V$^6$, V$^7$ and V$^8$ are each independently selected from the group consisting of N, and C(R$^{11}$);

wherein each R[11] is independently selected from the group consisting of: H, halogen, alkyl, alkenyl, alkynyl, haloalkyl, haloalkenyl, heteroalkyl, cycloalkyl, cycloalkenyl, heterocycloalkyl, heterocycloalkenyl, aryl, heteroaryl, cycloalkylalkyl, heterocycloalkylalkyl, arylalkyl, heteroarylalkyl, arylalkenyl, cycloalkylheteroalkyl, heterocycloalkylheteroalkyl, heteroarylheteroalkyl, arylheteroalkyl, hydroxy, hydroxyalkyl, alkoxy, alkoxyalkyl, alkoxyaryl, alkenyloxy, alkynyloxy, cycloalkylkoxy, heterocycloalkyloxy, aryloxy, arylalkyloxy, phenoxy, benzyloxy, heteroaryloxy, amino, alkylamino, aminoalkyl, acylamino, arylamino, sulfonylamino, sulfinylamino, —COOH, —COR³, —COOR³, —CONHR³, —NHCOR³, —NHCOOR³, —NHCONHR³, alkoxycarbonyl, alkylaminocarbonyl, alkylsulfonyl, alkylsulfinyl, arylsulfonyl, arylsulfinyl, aminosulfonyl, —SR³, R⁴S(O)R⁶—, R⁴S(O)₂R⁶—, R⁴C(O)N(R⁵)R⁶—, R⁴SO₂N(R⁵)R⁶—, R⁴N(R⁵)C(O)R⁶—, R⁴N(R⁵)SO₂R⁶—, R⁴N(R⁵)C(O)N(R⁵)R⁶— and acyl, each of which may be optionally substituted.

8. A compound according to claim 1 wherein Ar² is selected from the group consisting of:

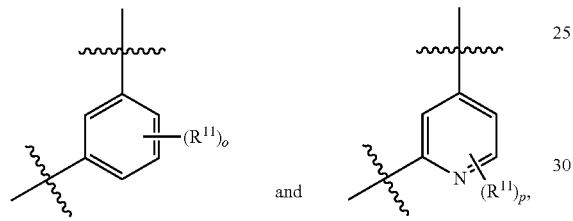

wherein each R[11] is independently selected from the group consisting of: H, halogen, alkyl, alkenyl, alkynyl, haloalkyl, haloalkenyl, heteroalkyl, cycloalkyl, cycloalkenyl, heterocycloalkyl, heterocycloalkenyl, aryl, heteroaryl, cycloalkylalkyl, heterocycloalkylalkyl, arylalkyl, heteroarylalkyl, arylalkenyl, cycloalkylheteroalkyl, heterocycloalkylheteroalkyl, heteroarylheteroalkyl, arylheteroalkyl, hydroxy, hydroxyalkyl, alkoxy, alkoxyalkyl, alkoxyaryl, alkenyloxy, alkynyloxy, cycloalkylkoxy, heterocycloalkyloxy, aryloxy, arylalkyloxy, phenoxy, benzyloxy, heteroaryloxy, amino, alkylamino, aminoalkyl, acylamino, arylamino, sulfonylamino, sulfinylamino, —COOH, —COR³, —COOR³, —CONHR³, —NHCOR³, —NHCOOR³, —NHCONHR³, alkoxycarbonyl, alkylaminocarbonyl, alkylsulfonyl, alkylsulfinyl, arylsulfonyl, arylsulfinyl, aminosulfonyl, —SR³, R⁴S(O)R⁶—, R⁴S(O)₂R⁶—, R⁴C(O)N(R⁵)R⁶—, R⁴SO₂N(R⁵)R⁶—, R⁴N(R⁵)C(O)R⁶—, R⁴N(R⁵)SO₂R⁶—, R⁴N(R⁵)C(O)N(R⁵)R⁶— and acyl, each of which may be optionally substituted;

o is an integer from 0 to 4; and
p is an integer from 0 to 3.

9. A compound according to claim 1 wherein Ar² is a group selected from the group consisting of:

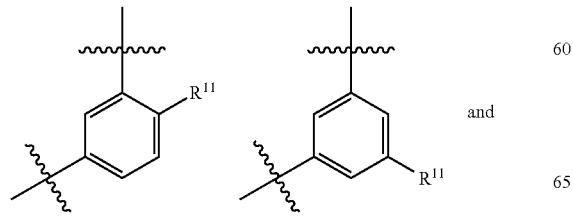

-continued

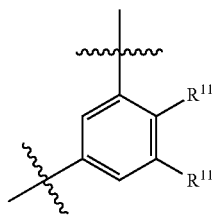

wherein each R[11] is independently selected from the group consisting of: H, halogen, alkyl, alkenyl, alkynyl, haloalkyl, haloalkenyl, heteroalkyl, cycloalkyl, cycloalkenyl, heterocycloalkyl, heterocycloalkenyl, aryl, heteroaryl, cycloalkylalkyl, heterocycloalkylalkyl, arylalkyl, heteroarylalkyl, arylalkenyl, cycloalkylheteroalkyl, heterocycloalkylheteroalkyl, heteroarylheteroalkyl, arylheteroalkyl, hydroxy, hydroxyalkyl, alkoxy, alkoxyalkyl, alkoxyaryl, alkenyloxy, alkynyloxy, cycloalkylkoxy, heterocycloalkyloxy, aryloxy, arylalkyloxy, phenoxy, benzyloxy, heteroaryloxy, amino, alkylamino, aminoalkyl, acylamino, arylamino, sulfonylamino, sulfinylamino, —COOH, —COR³, —COOR³, —CONHR³, —NHCOR³, —NHCOOR³, —NHCONHR³, alkoxycarbonyl, alkylaminocarbonyl, alkylsulfonyl, alkylsulfinyl, arylsulfonyl, arylsulfinyl, aminosulfonyl, —SR³, R⁴S(O)R⁶—, R⁴S(O)₂R⁶—, R⁴C(O)N(R⁵)R⁶—, R⁴SO₂N(R⁵)R⁶—, R⁴N(R⁵)C(O)R⁶—, R⁴N(R⁵)SO₂R⁶—, R⁴N(R⁵)C(O)N(R⁵)R⁶— and acyl, each of which may be optionally substituted.

10. A compound according to claim 1 wherein the compound is selected from the group consisting of:

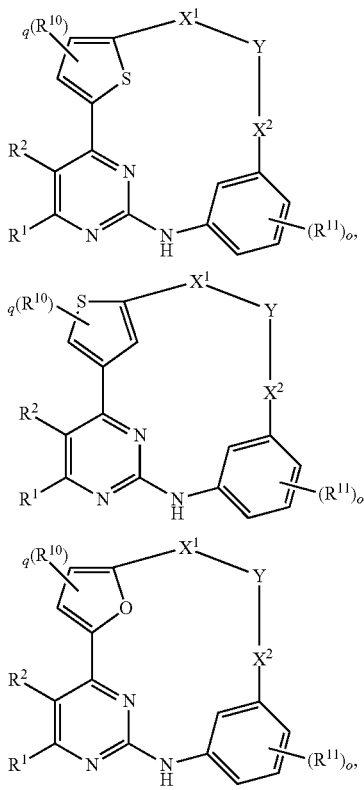

-continued

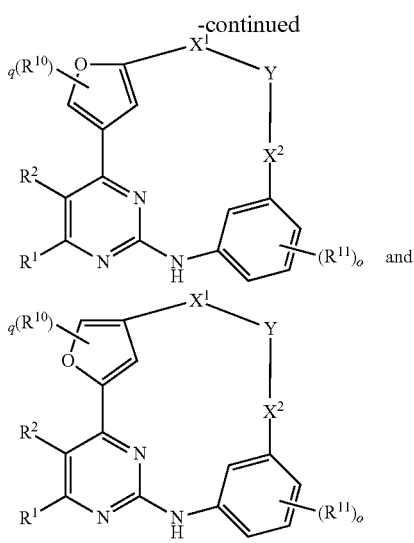

wherein each R¹⁰ is independently selected from the group consisting of: H, halogen, alkyl, alkenyl, alkynyl, haloalkyl, haloalkenyl, heteroalkyl, cycloalkyl, cycloalkenyl, heterocycloalkyl, heterocycloalkenyl, aryl, heteroaryl, cycloalkylalkyl, heterocycloalkylalkyl, arylalkyl, heteroarylalkyl, arylalkenyl, cycloalkylheteroalkyl, heterocycloalkylheteroalkyl, heteroarylheteroalkyl, arylheteroalkyl, hydroxy, hydroxyalkyl, alkoxy, alkoxyalkyl, alkoxyaryl, alkenyloxy, alkynyloxy, cycloalkylkoxy, heterocycloalkyloxy, aryloxy, arylalkyloxy, phenoxy, benzyloxy, heteroaryloxy, amino, alkylamino, aminoalkyl, acylamino, arylamino, sulfonylamino, sulfinylamino, —COOH, —COR³, —COOR³, —CONHR³, —NHCOR³, —NHCOOR³, —NHCONHR³, alkoxycarbonyl, alkylaminocarbonyl, alkylsulfonyl, alkylsulfinyl, arylsulfonyl, arylsulfinyl, aminosulfonyl, —SR³, R⁴S(O)R⁶—, R⁴S(O)₂R⁶—, R⁴C(O)N(R⁵)R⁶—, R⁴SO₂N(R⁵)R⁶—, R⁴N(R⁵)C(O)R⁶—, R⁴N(R⁵)SO₂R⁶—, R⁴N(R⁵)C(O)N(R⁵)R⁶— and acyl, each of which may be optionally substituted;

each R¹¹ is independently selected from the group consisting of: H, halogen, alkyl, alkenyl, alkynyl, haloalkyl, haloalkenyl, heteroalkyl, cycloalkyl, cycloalkenyl, heterocycloalkyl, heterocycloalkenyl, aryl, heteroaryl, cycloalkylalkyl, heterocycloalkylalkyl, arylalkyl, heteroarylalkyl, arylalkenyl, cycloalkylheteroalkyl, heterocycloalkylheteroalkyl, heteroarylheteroalkyl, arylheteroalkyl, hydroxy, hydroxyalkyl, alkoxy, alkoxyalkyl, alkoxyaryl, alkenyloxy, alkynyloxy, cycloalkylkoxy, heterocycloalkyloxy, aryloxy, arylalkyloxy, phenoxy, benzyloxy, heteroaryloxy, amino, alkylamino, aminoalkyl, acylamino, arylamino, sulfonylamino, sulfinylamino, —COOH, —COR³, —COOR³, —CONHR³, —NHCOR³, —NHCOOR³, —NHCONHR³, alkoxycarbonyl, alkylaminocarbonyl, alkylsulfonyl, alkylsulfinyl, arylsulfonyl, arylsulfinyl, aminosulfonyl, —SR³, R⁴S(O)R⁶—, R⁴S(O)₂R⁶—, R⁴C(O)N(R⁵)R⁶—, R⁴SO₂N(R⁵)R⁶—, R⁴N(R⁵)C(O)R⁶—, R⁴N(R⁵)SO₂R⁶—, R⁴N(R⁵)C(O)N(R⁵)R⁶— and acyl, each of which may be optionally substituted;

o is an integer from 0 to 4; and q is an integer from 0 to 2;

or a pharmaceutically acceptable salt thereof.

11. A compound according to claim 1 wherein $X^1$ and $X^2$ are each independently selected from the group consisting of:
   (a) —OC$_{1-5}$alkyl-,
   (b) —C$_{1-5}$alkylO—, and
   (c) —C$_{1-5}$alkylOC$_{1-5}$alkyl.

12. A compound according to claim 1 wherein $X^1$ is selected from the group consisting of:
   (a) —OCH$_2$—
   (b) —CH$_2$O—,
   (c) —OCH$_2$CH$_2$—,
   (d) —CH$_2$CH$_2$O—,
   (e) —CH$_2$OCH$_2$—, and
   (f) —CH$_2$CH$_2$OCH$_2$—.

13. A compound according to claim 1 wherein $X^2$ is selected from the group consisting of:
   (a) —OCH$_2$
   (b) —CH$_2$O—,
   (c) —OCH$_2$CH$_2$—,
   (d) —CH$_2$CH$_2$O—,
   (e) —CH$_2$OCH$_2$—, and
   (f) —CH$_2$CH$_2$OCH$_2$—.

14. A compound according to claim 1 selected from the group consisting of:

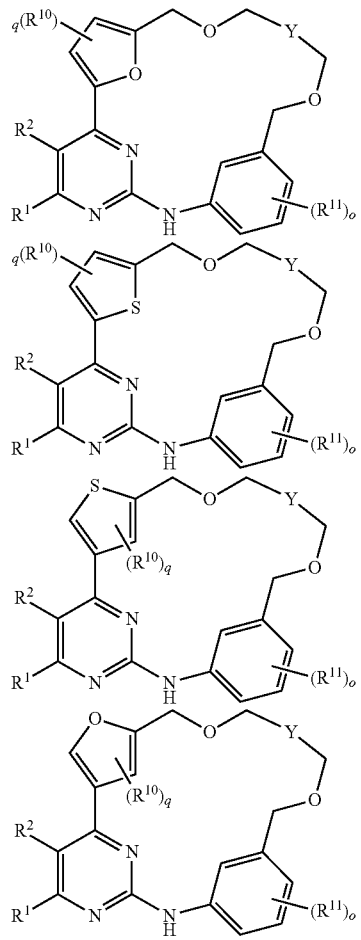

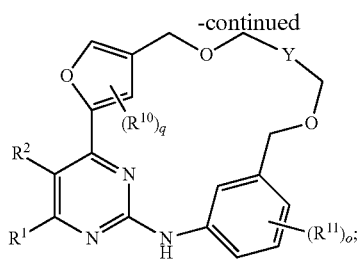

wherein each $R^{10}$ is independently selected from the group consisting of: H, halogen, alkyl, alkenyl, alkynyl, haloalkyl, haloalkenyl, heteroalkyl, cycloalkyl, cycloalkenyl, heterocycloalkyl, heterocycloalkenyl, aryl, heteroaryl, cycloalkylalkyl, heterocycloalkylalkyl, arylalkyl, heteroarylalkyl, arylalkenyl, cycloalkylheteroalkyl, heterocycloalkylheteroalkyl, heteroarylheteroalkyl, arylheteroalkyl, hydroxy, hydroxyalkyl, alkoxy, alkoxyalkyl, alkoxyaryl, alkenyloxy, alkynyloxy, cycloalkyloxy, heterocycloalkyloxy, aryloxy, arylalkyloxy, phenoxy, benzyloxy, heteroaryloxy, amino, alkylamino, aminoalkyl, acylamino, arylamino, sulfonylamino, sulfinylamino, —COOH, —COR$^3$, —COOR$^3$, —CONHR$^3$, —NHCOR$^3$, —NHCOOR$^3$, —NHCONHR$^3$, alkoxycarbonyl, alkylaminocarbonyl, alkylsulfonyl, alkylsulfinyl, arylsulfonyl, arylsulfinyl, aminosulfonyl, —SR$^3$, R$^4$S(O)R$^6$—, R$^4$S(O)$_2$R$^6$—, R$^4$C(O)N(R$^5$)R$^6$—, R$^4$SO$_2$N(R$^5$)R$^6$—, R$^4$N(R$^5$)C(O)R$^6$—, R$^4$N(R$^5$)SO$_7$R$^6$—, R$^4$N(R$^5$)C(O)N(R$^5$)R$^6$— and acyl, each of which may be optionally substituted;

each $R^{11}$ is independently selected from the group consisting of: H, halogen, alkyl, alkenyl, alkynyl, haloalkyl, haloalkenyl, heteroalkyl, cycloalkyl, cycloalkenyl, heterocycloalkyl, heterocycloalkenyl, aryl, heteroaryl, cycloalkylalkyl, heterocycloalkylalkyl, arylalkyl, heteroarylalkyl, arylalkenyl, cycloalkylheteroalkyl, heterocycloalkylheteroalkyl, heteroarylheteroalkyl, arylheteroalkyl, hydroxy, hydroxyalkyl, alkoxy, alkoxyalkyl, alkoxyaryl, alkenyloxy, alkynyloxy, cycloalkyloxy, heterocycloalkyloxy, aryloxy, arylalkyloxy, phenoxy, benzyloxy, heteroaryloxy, amino, alkylamino, aminoalkyl, acylamino, arylamino, sulfonylamino, sulfinylamino, —COOH, —COR$^3$, —COOR$^3$, —CONHR$^3$, —NHCOR$^3$, —NHCOOR$^3$, —NHCONHR$^3$, alkoxycarbonyl, alkylaminocarbonyl, alkylsulfonyl, alkylsulfinyl, arylsulfonyl, arylsulfinyl, aminosulfonyl, —SR$^3$, R$^4$S(O)R$^6$—, R$^4$S(O)$_7$R$^6$—, R$^4$C(O)N(R$^5$)R$^6$—, R$^4$SO$_2$N(R$^5$)R$^6$—, R$^4$N(R$^5$)C(O)R$^6$—, R$^4$N(R$^5$)SO$_2$R$^6$—, R$^4$N(R$^5$)C(O)N(R$^5$)R$^6$— and acyl, each of which may be optionally substituted;

o is an integer from 0 to 4; and q is an integer from 0 to 2;

or a pharmaceutically acceptable salt thereof.

15. A compound according to claim 1 wherein $R^1$ and $R^2$ are independently selected from the group consisting of H and methyl.

16. A compound according to claim 14 wherein $R^{10}$ is selected from the group consisting of H, halogen, amino, alkyl, haloalkyl, haloalkenyl, heterocycloalkyl, aryl, cycloalkylalkyl, heterocycloalkylalkyl, arylalkyl, heteroarylalkyl, cycloalkylheteroalkyl, heterocycloalkylheteroalkyl, heteroarylheteroalkyl, arylheteroalkyl, hydroxy, hydroxyalkyl, alkoxy, and alkoxyalkyl, each of which may be optionally substituted.

17. A compound according to claim 14 wherein $R^{10}$ is selected from the group consisting of H, hydroxyl, methoxy, fluoro, methyl, ethyl, propyl, butyl, pentyl, hexyl, phenyl, and 2-morpholino-ethoxy, each of which may be optionally substituted.

18. A compound according to claim 14 wherein each $R^{11}$ is independently selected from the group consisting of H, alkoxy, heteroalkyl, heterocycloalkyl, heterocycloalkylheteroalkyl, heteroarylheteroalkyl, and arylsulfonyloxy, each of which may be optionally substituted.

19. A compound according to claim 14 wherein each $R^{11}$ is independently selected from the group consisting of:

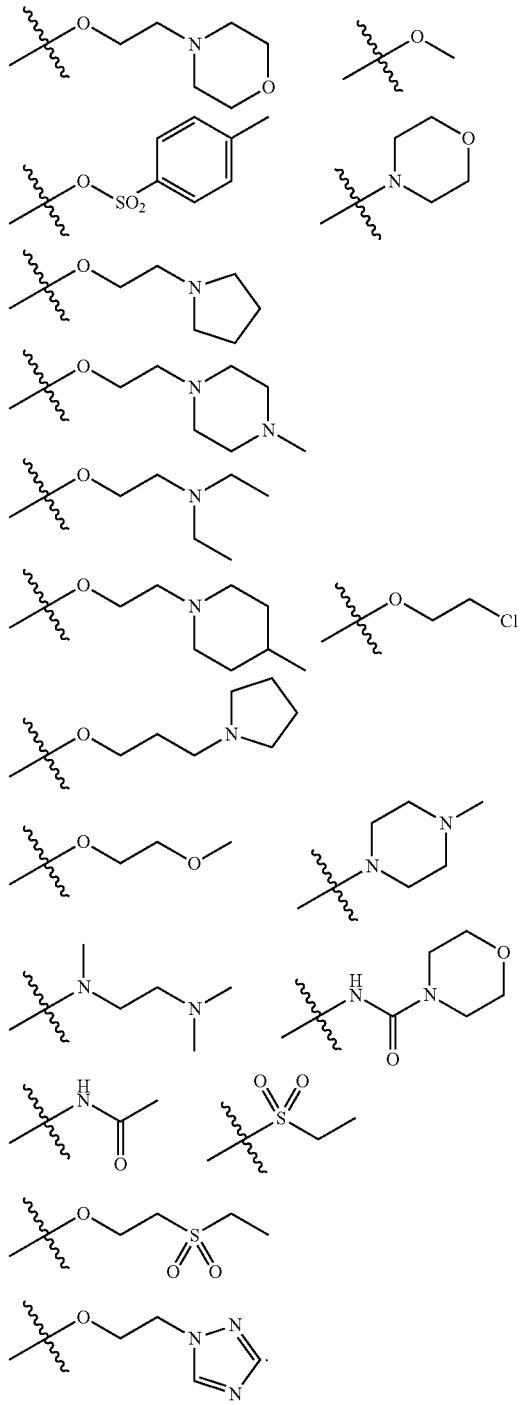

20. A compound according to claim 1 wherein Y is selected from the group consisting of:

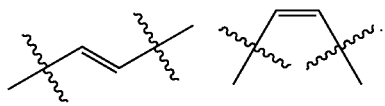

21. A compound according to claim 1 wherein the optional substituent is selected from the group consisting of: halogen, =O, =S, —CN, —NO₂, —CF₃, —OCF₃, alkyl, alkenyl, alkynyl, haloalkyl, haloalkenyl, haloalkynyl, heteroalkyl, cycloalkyl, cycloalkenyl, heterocycloalkyl, heterocycloalkenyl, aryl, heteroaryl, hydroxy, hydroxyalkyl, alkoxy, alkoxyalkyl, alkoxyaryl, alkoxyheteroaryl, alkenyloxy, alkynyloxy, cycloalkyloxy, cycloalkenyloxy, heterocycloalkyloxy, heterocycloalkenyloxy, aryloxy, heteroaryloxy, arylalkyl, heteroarylalkyl, arylalkyloxy, -amino, alkylamino, acylamino, aminoalkyl, arylamino, alkylsulfonyl, arylsulfonyl, aminosulfonyl, aminoalkyl, alkoxyalkyl, —COOH, —COR⁵, —C(O)OR⁵, —SH, —SR⁵, —OR⁶ and acyl.

22. A compound according to claim 1 selected from the group consisting of:

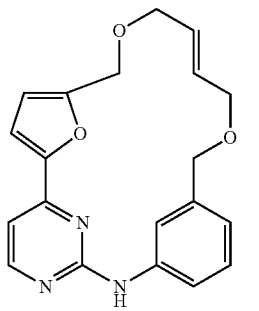

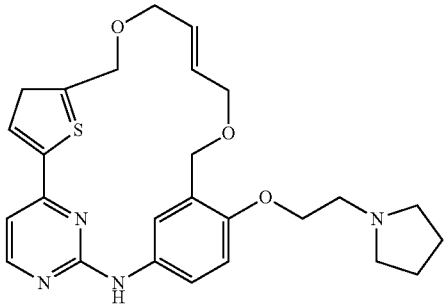

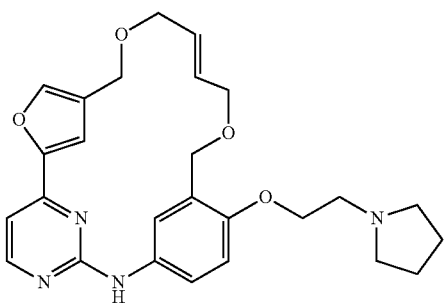

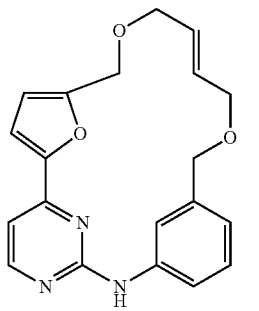

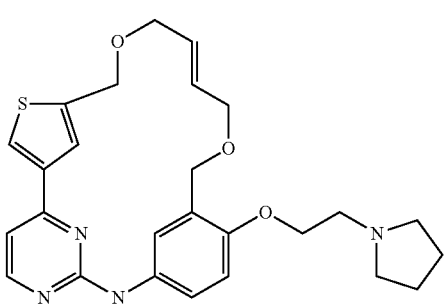

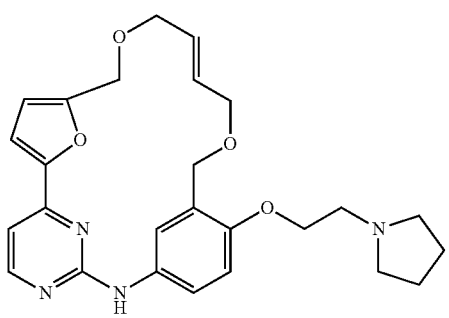

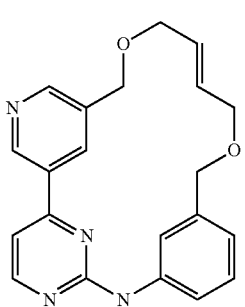

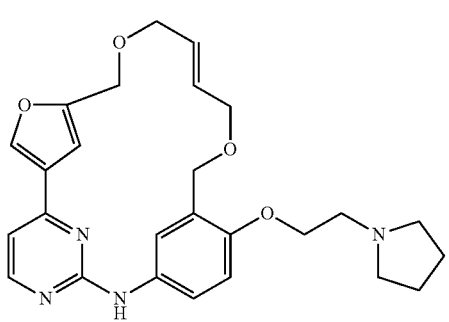

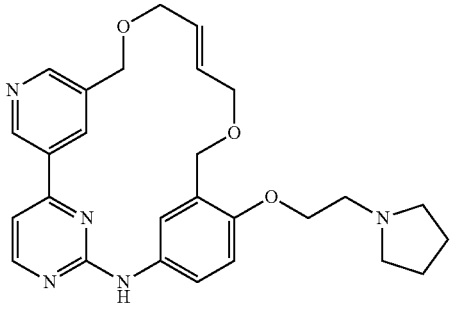

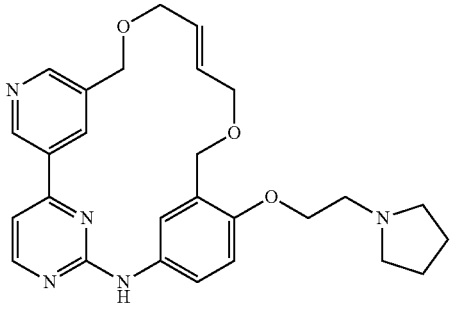

or a pharmaceutically acceptable salt or ester thereof.

23. A pharmaceutical composition including comprising a compound according to claim 1 and a pharmaceutically acceptable diluent, excipient or carrier.

24. A method of synthesis of a compound of formula I as defined in claim 1 the method including the steps of:

(a) providing a compound of the formula

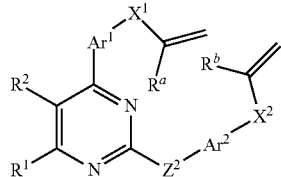

(b) subjecting the compound to ring closing metathesis;

(c) optionally reacting the double bond thus formed to form a cycloalkyl group.

25. A method according to claim 24 wherein step (b) involves treating the trifluoroacetic acid (TFA) or hydrochloric acid (HCl) salt of the compound with 5-10 mole % of Grubbs $2^{nd}$ generation catalyst in dichloromethane at 40° C.

26. A method according to claim 24 or 25 wherein step (c) includes treating the metathesis product with a freshly prepared ethereal solution of diazomethane ($CH_2N_2$) in dichloromethane/dioxane at 0° C.

27. A compound according to claim 22 of the formula:

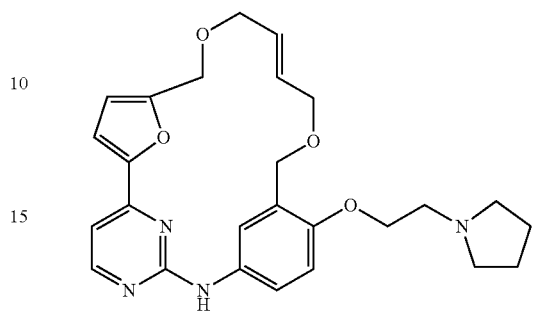

or a pharmaceutically acceptable salt or ester thereof.

28. A pharmaceutical composition comprising a compound according to claim 27 and a pharmaceutically acceptable diluent, excipient or carrier.

* * * * *